US008679822B2

(12) United States Patent
Caimi et al.

(10) Patent No.: US 8,679,822 B2
(45) Date of Patent: Mar. 25, 2014

(54) XYLOSE UTILIZATION IN RECOMBINANT ZYMOMONAS

(75) Inventors: Perry G. Caimi, Kennett Square, PA (US); Laura McCole, East Fallowfield, PA (US); Luan Tao, Wallingford, PA (US); Jean-Francois Tomb, Wilmington, DE (US); Paul V. Viitanen, West Chester, PA (US)

(73) Assignee: E I du Pont de Nemours and Company, Wilmington, DE (US)

( * ) Notice: Subject to any disclaimer, the term of this patent is extended or adjusted under 35 U.S.C. 154(b) by 51 days.

(21) Appl. No.: 13/161,734

(22) Filed: Jun. 16, 2011

(65) Prior Publication Data

US 2012/0156746 A1 Jun. 21, 2012

Related U.S. Application Data

(60) Provisional application No. 61/359,445, filed on Jun. 29, 2010.

(51) Int. Cl.

| | |
|---|---|
| ***C12N 1/20*** | (2006.01) |
| ***C12N 9/24*** | (2006.01) |
| ***C12N 9/90*** | (2006.01) |
| ***C12N 15/00*** | (2006.01) |
| ***C12N 15/74*** | (2006.01) |
| ***C12P 21/06*** | (2006.01) |
| ***C07H 21/02*** | (2006.01) |
| ***C07H 21/04*** | (2006.01) |

(52) U.S. Cl.

USPC ....... 435/252.3; 435/200; 435/233; 435/69.1; 435/161; 435/471; 435/476; 435/320.1; 536/23.1; 536/23.2; 536/23.4; 536/23.7

(58) Field of Classification Search

None

See application file for complete search history.

(56) References Cited

U.S. PATENT DOCUMENTS

| | | | | |
|---|---|---|---|---|
| 5,514,583 A | | 5/1996 | Picataggio et al. | |
| 5,712,133 A | | 1/1998 | Picataggio et al. | |
| 6,566,107 B1 | | 5/2003 | Zhang | |
| 7,223,575 B2 | | 5/2007 | Zhang et al. | |
| 7,741,084 B2 | | 6/2010 | Viitanen et al. | |
| 7,741,119 B2 | | 6/2010 | Viitanen et al. | |
| 7,803,623 B2 | | 9/2010 | Caimi et al. | |
| 7,897,396 B2 | | 3/2011 | Caimi et al. | |
| 7,989,206 B2 | | 8/2011 | Viitanen et al. | |
| 7,998,722 B2 | | 8/2011 | Viitanen et al. | |
| 2008/0261287 A1 | * | 10/2008 | Winkler et al. | 435/161 |
| 2011/0014670 A1 | | 1/2011 | Caimi et al. | |
| 2011/0143408 A1 | | 6/2011 | Yang | |

OTHER PUBLICATIONS

Karhumaa, Kaisa et al., Investigation of limiting metabolic steps in the utilization of xylose by recombinant *Saccharomyces cervisiae* using metablic engineering, Yeast, 2005, pp. 359-368, vol. 22.

International Search Report dated Oct. 21, 2011, International Application No. PCT/US2011/042122.

Feldmann, Sigrun D. et al., Pentose metabolism in *Zymomonas mobilis* wild-type and recombinant strains, Applied Microbiology and Biotechnology, 1992, pp. 354-361, vol. 38, Springer-Verlag.

Yanase, Hideshi et al., Genetic Engineering of *Zymobacter palmae* for Production of Ethanol from Xylose, Applied and Environmental Microbiology, Apr. 2007, pp. 2592-2599, vol. 73, No. 8, American Society for Microbiology.

Zhang, Min et al., Metabolic Engineering of a Pentose Metabolism Pathway in Ethanologenic *Zymomonas mobilis,* Science, Jan. 13, 1995, pp. 240-243, vol. 267.

Kahsay, Robel et al., U.S. Appl. No. 13/161,749, filed Jun. 16, 2011.

* cited by examiner

*Primary Examiner* — Robert Mondesi
*Assistant Examiner* — Iqbal H Chowdhury

(57) ABSTRACT

Xylose-utilizing *Zymomonas* strains studied were found to accumulate ribulose when grown in xylose-containing media. Engineering these strains to increase ribose-5-phosphate isomerase activity led to reduced ribulose accumulation, improved growth, improved xylose utilization, and increased ethanol production.

12 Claims, 7 Drawing Sheets

XYLOSE UTILIZATION IN RECOMBINANT ZYMOMONAS

This application claims the benefit of U.S. Provisional Application 61/359,445, filed Jun. 29, 2010.

STATEMENT OF GOVERNMENT RIGHTS

This invention was made with United States government support under Contract Nos. DE-FC36-07GO17056 awarded by the Department of Energy. The government has certain rights in this invention.

FIELD OF THE INVENTION

The invention relates to the fields of microbiology and genetic engineering. More specifically, increasing ribose-5-phosphate isomerase activity in xylose utilizing *Z. mobilis* improved xylose utilization by the microorganism.

BACKGROUND OF THE INVENTION

Production of ethanol by microorganisms provides an alternative energy source to fossil fuels and is therefore an important area of current research. It is desirable that microorganisms producing ethanol, as well as other useful products, be capable of using xylose as a carbon source since xylose is the major pentose in hydrolyzed lignocellulosic biomass. Biomass can provide an abundantly available, low cost carbon substrate. *Zymomonas mobilis* and other bacterial ethanologens which do not naturally utilize xylose have been genetically engineered for xylose utilization by introduction of genes encoding 1) xylose isomerase, which catalyses the conversion of xylose to xylulose; 2) xylulokinase, which phosphorylates xylulose to form xylulose 5-phosphate; 3) transketolase; and 4) transaldolase.

There has been success in engineering *Z. mobilis* strains for xylose metabolism (U.S. Pat. No. 5,514,583, U.S. Pat. No. 5,712,133, U.S. Pat. No. 6,566,107, WO 95/28476, Feldmann et al. (1992) *Appl Microbiol Biotechnol* 38: 354-361, Zhang et al. (1995) Science 267:240-243), as well as a *Zymobacter palmae* strain (Yanase et al. (2007) *Appl. Environ. Mirobiol.* 73:2592-2599). However, typically the engineered strains do not grow and produce ethanol as well on xylose as on glucose. Strains engineered for xylose utilization have been adapted by serial passage on xylose medium, resulting in strains with improved xylose utilization as described in U.S. Pat. No. 7,223,575 and commonly owned and co-pending U.S. Pat. No. 7,741,119. Disclosed in commonly owned and co-pending US Patent App. No. US 2009-0246846 A1 is the finding that an adapted strain with higher xylose utilization has increased xylose isomerase activity, and engineering for improved xylose utilization by expression of xylose isomerase from a mutated, highly active *Zymomonas mobilis* glyceraldehyde-3-phosphate dehydrogenase gene promoter (Pgap). However xylose utilization is still not comparable to glucose utilization.

There remains a need for strains of *Zymomonas*, and other bacterial ethanolagens, which have further improvement in xylose utilization.

SUMMARY OF THE INVENTION

The invention provides ethanol producing, recombinant xylose-utilizing *Zymomonas* or *Zymobacter* cells that are engineered to have increased ribose-5-phosphate isomerase (RPI) activity. It has been discovered that, in strains where xylose isomerase activity is high, the carbon flux to RPI is also high and results in the generation of the undesirable by products ribulose-5-phosphate and/or ribulose (catalyzed by cellular phosphotases), which accumulate in the medium. Generation of these by-products siphons off carbon that could be used in the production of ethanol. Applicants' solution to this newly discovered problem is to increase the activity of RPI to direct more carbon to the desired products of the xylose metabolic pathway (fructose-6 phosphate and glyceraldyhyde-6 phosphate) which are used in the generation of ethanol. Thus, in xylose-utilizing *Zymomonas* or *Zymobacter* strains that accumulate ribulose-5-phosphate and/or ribulose when grown in xylose containing medium, an increase in RPI activity improves cell growth, xylose utilization, and ethanol production.

Accordingly, the invention provides a recombinant bacterial host cell comprising:

a) a xylose metabolic pathway comprising at least one gene encoding a polypeptide having xylose isomerase activity;

b) at least one gene encoding a polypeptide having ribose-5-phosphate isomerase activity; and c) at least one genetic modification which increases ribose-5-phosphate isomerase activity in the host cell as compared with ribose-5-phosphate isomerase activity in the host cell lacking said genetic modification;

wherein, the bacterial host cell utilizes xylose to produce ethanol; and wherein the bacterial host cell is selected from the group consisting of *Zymomonas* and *Zymobacter*.

The ribose-5-phosphate isomerase of the invention may be of the "A" type or the "B" type as described herein. Preferred "A" type ribose-5-phosphate isomerases are those that: i) give an E-value score of 0.1 or less when queried using a Profile Hidden Markov Model prepared using SEQ ID NOs: 83, 84, 85, 86, 87, 88, 89, 90, 91, 92, 93, 94, 95, 96, and 97; the query being carried out using the hmmsearch algorithm wherein the Z parameter is set to 1 billion, and ii) have aspartic acid and glutamic acid at positions corresponding to 107 and 129, respectively, in the *Saccharomyces cerevisiae* RPI-A protein of SEQ ID NO:97.

Similarly, preferred "B" type ribose-5-phosphate isomerases are those that i) give an E-value score of 0.1 or less when queried using a Profile Hidden Markov Model prepared using SEQ ID NOs:1213, 1214, 1215, 1216, and 1217; the query being carried out using the hmmsearch algorithm wherein the Z parameter is set to 1 billion;

ii) either have cysteine and threonine at positions corresponding to 66 and 68, respectively, in the *E. coli* RPI-B protein of SEQ ID NO:1216 or have serine and glutamic acid at positions corresponding to 68 and 72, respectively, in the *M. tuberculosis* RPI-B protein of SEQ ID NO:1213, and iii) have asparagine, glycine, aspartic acid, serine, or glutamic acid but not leucine at the position corresponding to 100 in the *E. coli* RPI-B protein of SEQ ID NO:1216.

Preferred xylose isomerases of the invention are those that have an E-value score of less than or equal to $3\times10^{-10}$ when queried using a Profile HMM prepared using SEQ ID NOs: 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, and 81, and having four catalytic site residues: histine 54, aspartic acid 57, glutamic acid 181, and lysine 183, with the position numbers in reference to the *Streptomyces albus* xylose isomerase sequence of SEQ ID NO:61.

Additionally the invention provides a method for making a recombinant bacterial host cell for the production of ethanol comprising:

a) providing a *Zymomonas* or *Zymobacter* bacterial host cell comprising a xylose metabolic pathway wherein the bacterial host cell produces ethanol in the presence of xylose and accumulates ribulose-5-phosphate, ribulose, or both ribulose-5-phosphate and ribulose in a medium when grown in a medium comprising xylose; and b) genetically modifying the bacterial host cell of (a) wherein the genetic modification increases ribose-5-phosphate isomerase activity in the host cell as compared with ribose-5-phosphate isomerase activity in the host cell lacking said genetic modification;

wherein ribulose-5-phosphate, ribulose, or both ribulose-5-phosphate and ribulose no longer accumulate in the medium.

In another embodiment the invention provides a process for producing ethanol comprising:

a) providing a ethanol producing recombinant bacterial host cell of the invention; and b) culturing the host of (a) in a medium comprising xylose whereby xylose is converted to ethanol.

BRIEF DESCRIPTION OF THE BIOLOGICAL DEPOSITS, FIGURES AND SEQUENCE DESCRIPTIONS

Applicants have made the following biological deposits under the terms of the Budapest Treaty on the International Recognition of the Deposit of Microorganisms for the Purposes of Patent Procedure:

Information on Deposited Strains

| Depositor Identification Reference | International Depository Designation | Date of Deposit |
|---|---|---|
| *Zymomonas* ZW658 | ATCC No PTA-7858 | Sep. 12, 2006 |

Figure 6:
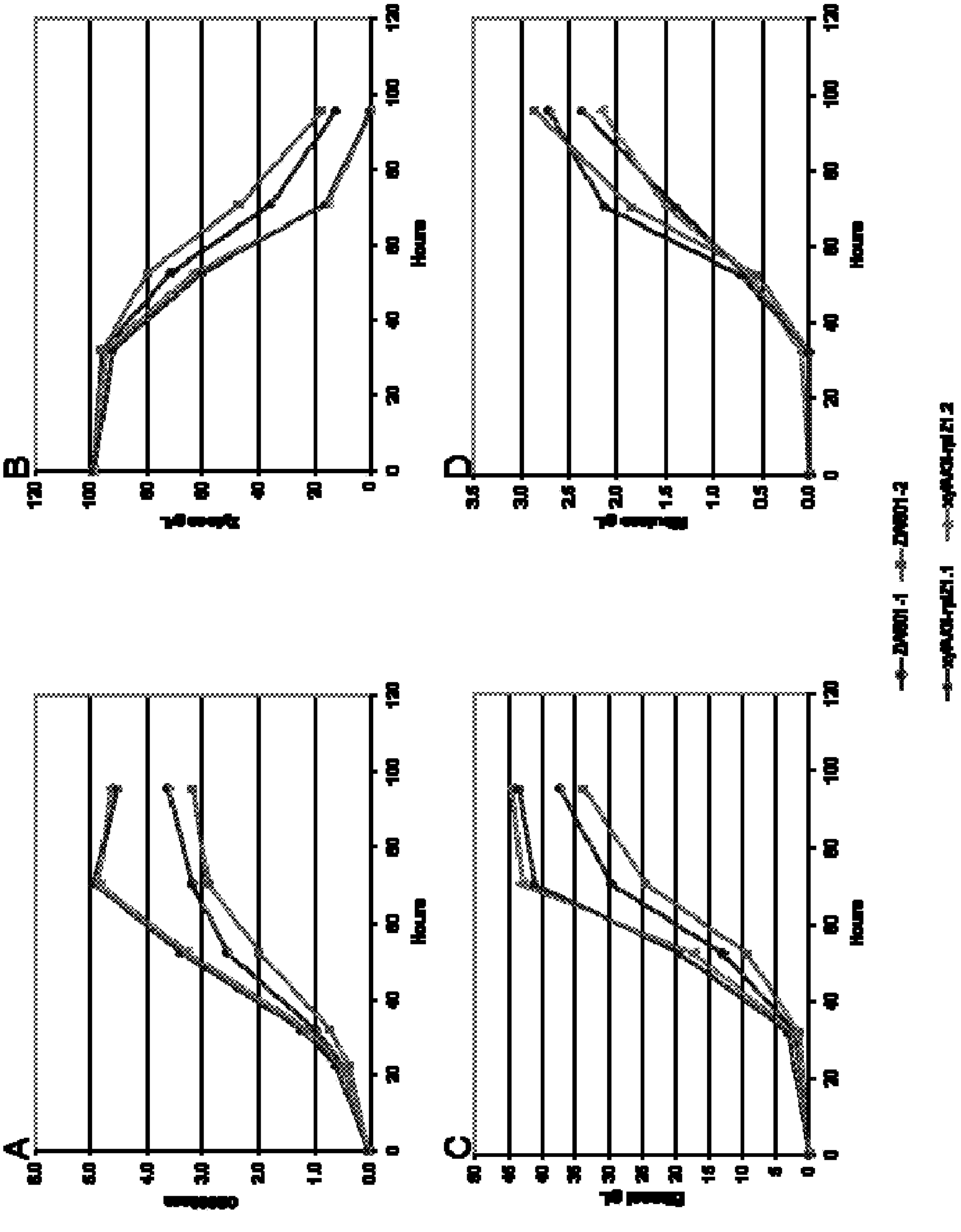

FIG. 6 shows graphs of growth (A), xylose utilization (B), ethanol production (C), and ribulose accumulation in media (D) of cultures of ZW801-4 control strains (ZW801-1 and ZW801-2) and ZW801-4 strains containing a plasmid containing a chimeric gene with an *A. missouriensis* GI promoter and *Z. mobilis* RPI-A coding region and a plasmid containing a chimeric gene with *Z. mobilis* GAP promoter and *E. coli* xylA coding region (xylA/G1-rpiZ1.1 and xylA/G1-rpiZ1.2).

Figure 7:
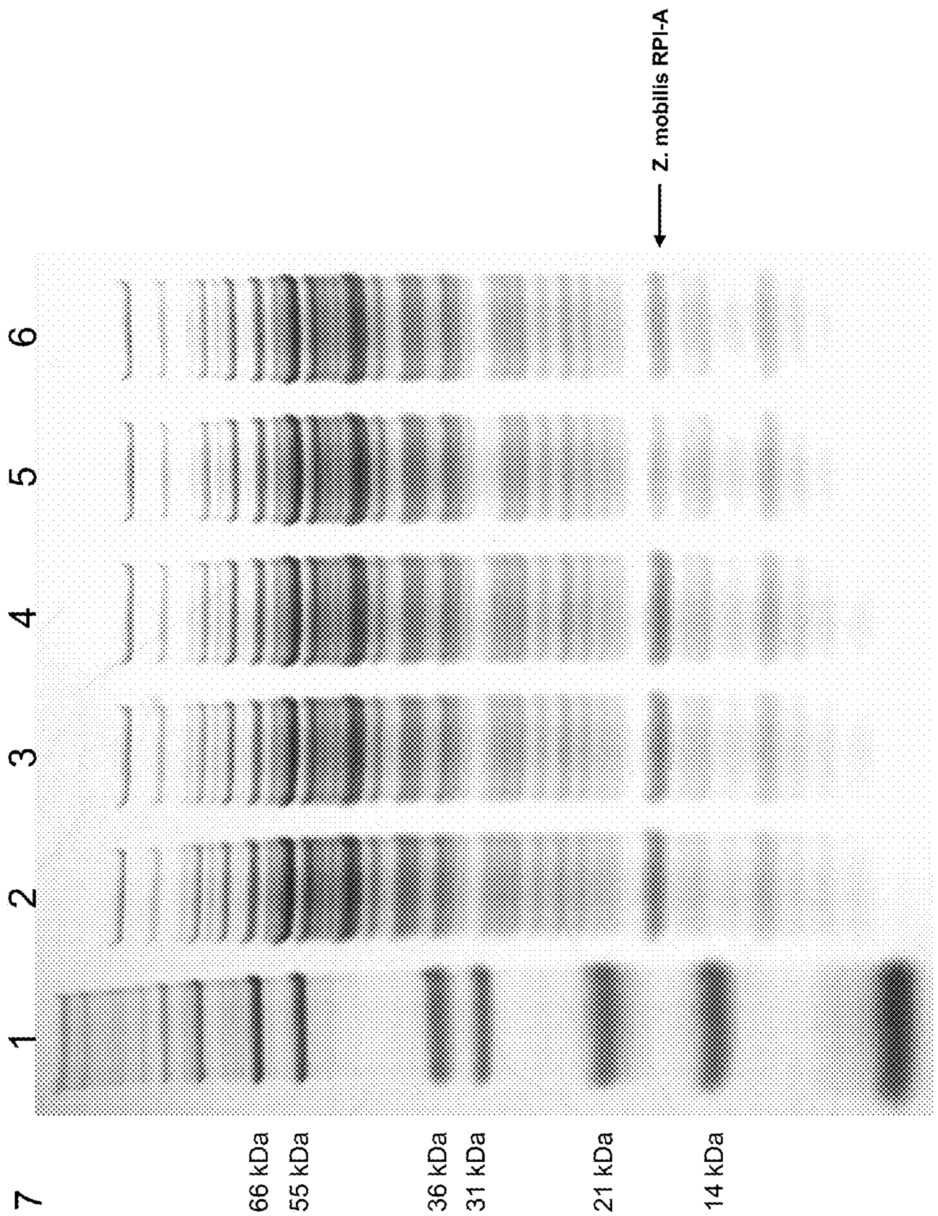

FIG. 7 shows a stained gel of markers (lane 1) and total protein extracts of cells expressing RPI-A with an ATG start codon in ZW801 GAP-rpi-1, ZW801 GAP-rpi-3 and ZW801 GAP-rpi-4 (lanes 2, 3, and 4, respectively) and controls expressing RPI-A with the native GTG start codon (lanes 5 and 6), with the position of the *Z. mobilis* RPI-A protein marked by an arrow.

Table 3 is a table of the Profile HMM for xylose isomerases. Table 3 is submitted herewith electronically and is incorporated herein by reference.

Table 4 is a table of the Profile HMM for RPI-A proteins. Table 4 is submitted herewith electronically and is incorporated herein by reference.

Table 5 is a table of the Profile HMM for RPI-B proteins. Table 5 is submitted herewith electronically and is incorporated herein by reference.

The following sequences conform with 37 C.F.R. 1.821-1.825 ("Requirements for patent applications Containing Nucleotide Sequences and/or Amino Acid Sequence Disclosures—the Sequence Rules") and consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

SEQ ID NOs:1-13 are oligonucleotide primers.

SEQ ID NO:14 is the nucleotide sequence of the promoter from the glucose isomerase gene of *Actinoplanes missouriensis.*

SEQ ID NO:15 is the nucleotide sequence of the pZB188/aadA plasmid.

SEQ ID NO:16 is the nucleotide sequence of the pZB-GI-RPI plasmid.

SEQ ID NO:17 is the nucleotide sequence of the glyceraldehyde-3-phosphate dehydrogenase (GAP) promoter from *Z. mobilis* strain ZW1 (ZW4).

SEQ ID NO:18 is the nucletotide sequence of the xylose isomerase expression cassette PgapXylA.

TABLE 1

SEQ ID numbers of xylose isomerase proteins and their coding regions

| Organism | SEQ ID NO: Protein | SEQ ID NO: Coding region |
|---|---|---|
| *Escherichia coli* K12 | 19 | 20 |
| *Lactobacillus brevis* ATCC 367 | 21 | 22 |
| *Thermoanaerobacterium* | 23 | 24 |
| *Clostridium thermosulfurogenes* | 25 | 26 |
| *Actinoplanes Missouriensis* | 27 | 28 |
| *Arthrobacter* Strain B3728 | 29 | 30 |
| *Baccillus licheniformis* ATCC 14580 | 31 | 32 |
| *Geobacillus stearothermophilus* | 33 | 34 |
| *Bacillus coagulans* 36D1 | 35 | 36 |
| *Bacillus subtilis* subsp. *subtilis* str. 168 | 37 | 38 |
| *Bacteroides vulgatus* ATCC 8482 | 39 | 40 |
| *Bifidobacterium adolescentis* ATCC 15703 | 41 | 42 |
| *Erwinia carotovora* subsp. *atroseptica* SCRI1043 | 43 | 44 |
| *Hordeum vulgare* subsp. *vulgare* | 45 | 46 |
| *Klebsiella pneumoniae* subsp. *pneumoniae* MGH 78578 | 47 | 48 |
| *Lactococcus lactis* subsp. *lactis* | 49 | 50 |

TABLE 1-continued

SEQ ID numbers of xylose isomerase proteins and their coding regions

| Organism | SEQ ID NO: Protein | SEQ ID NO: Coding region |
|---|---|---|
| *Lactobacillus reuteri* 100-23 | 51 | 52 |
| *Leuconostoc mesenteroides* subsp. *mesenteroides* ATCC 8293 | 53 | 54 |
| *Thermoanaerobacterium Thermosulfurisgenes* | 55 | 56 |
| *Thermotoga Neapolitana* | 57 | 58 |
| *Streptomyces Rubiginosus* | 59 | 60 |
| *Streptomyces albus* | 61 | 62[1] |
| *Thermus thermophilus* | 63 | 64 |
| *Streptomyces diastaticus* | 65 | 66 |
| *Streptomyces coelicolor* A3(2) | 67 | 68 |
| *Thermus Caldophilus* | 69 | 70[2] |
| *Xanthomonas campestris* pv. *vesicatoria* str. 85-10 | 71 | 72 |
| *Thermus aquaticus* | 73 | 74[3] |
| *Tetragenococcus halophilus* | 75 | 76 |
| *Staphylococcus xylosus* | 77 | 78 |
| *Mycobacterium smegmatis* str. MC2 155 | 79 | 80 |
| *Piromyces* sp. E2 | 81 | 82 |

[1]This coding sequence is designed, based on the *Streptomyces rubiginosus* coding sequence, to encode the *Streptomyces albus* protein (which has three amino acid differences with the *Streptomyces rubiginosus* protein.

[2]This coding sequence is designed, based on a *Thermus thermophilus* coding sequence, to encode the *Thermus Caldophilus* protein (which has 21 amino acid differences with the *Streptomyces rubiginosus* protein.

[3]This coding sequence is from *Thermus thermophilus* and translates to the *Thermus aquaticus* protein, although the *Thermus aquaticus* coding sequence may have differences due to codon degeneracy.

TABLE 2

SEQ ID numbers of ribose-5-phosphate isomerase proteins used as seed sequences for RPI-A structure analysis and their coding regions

| Organism | SEQ ID NO: protein | SEQ ID NO: coding region |
|---|---|---|
| *Escherichia coli* str. K-12 substr. DH10B | 83 | 2108 |
| *Enterobacter cloacae* | 84 | 2109 |
| *Vibrio vulnificus* | 85 | 2110 |
| *Thermus thermophilus* HB8 | 86 | 2111 |
| *Chlamydomonas reinhardtii* | 87 | 2112 |
| *Spinacia oleracea* | 88 | 2113 |
| *Arabidopsis thaliana* | 89 | 2114 |
| *Arabidopsis thaliana* | 90 | 2115 |
| *Plasmodium falciparum* 3D7 | 91 | 2116 |
| *Pyrococcus horikosshii* OT3 | 92 | 2117 |
| *Methanocaldococcus jannaschii* DSM 2661 | 93 | 2118 |
| *Fibrobacter succinogenes* subsp. *succinogenes* S85 | 94 | 2119 |
| *Homo sapiens* | 95 | 2120 |
| *Caenorthabditis elegans* | 96 | 2121 |
| *Saccharomyces cerevisiae* | 97 | 2122 |

SEQ ID NOs:98-1212 are RPI-A ribose-5-phosphate isomerase proteins.

SEQ ID NOs:2123-3237 are sequences encoding RPI-A ribose-5-phosphate isomerase proteins.

TABLE 3

SEQ ID numbers of ribose-5-phosphate isomerase proteins used as seed sequences for RPI-B structure analysis and their coding regions

| Organism | SEQ ID NO: protein | SEQ ID NO: coding region |
|---|---|---|
| *Mycobacterium tuberculosis* CDC1551 | 1213 | 3238 |
| *Thermotoga maritima* MSB8 | 1214 | 3239 |
| *Clostridium thermocellum* ATCC 27405 | 1215 | 3240 |
| *Escherichia coli* str. K-12 substr. MG1655 | 1216 | 3241 |
| *Trypanosoma cruzi* strain *CL Brener* | 1217 | 3242 |

SEQ ID NOs:1218-2107 are RPI-B ribose-5-phosphate isomerase proteins.

SEQ ID NOs:3243-4132 are sequences encoding RPI-B ribose-5-phosphate isomerase proteins.

DETAILED DESCRIPTION

Disclosed herein are xylose-utilizing *Zymomonas* or *Zymobacter* strains that are genetically modified to have increased expression of ribose-5-phosphate isomerase (RPI) activity, as compared to strains without the genetic modification. When ribulose is produced as a side product in xylose utilization, the increased RPI activity provides improved xylose utilization, which is desired for growth in media containing xylose including saccharified biomass, leading to increased ethanol production. Ethanol is an important compound for use in replacing fossil fuels and saccharified biomass provides a renewable carbon source for ethanol production by fermentation.

The following definitions may be used for the interpretation of the claims and specification:

As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but may include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

The term "invention" or "present invention" as used herein is a non-limiting term and is not intended to refer to any single embodiment of the particular invention but encompasses all possible embodiments as described in the specification and the claims.

As used herein, the term "about" modifying the quantity of an ingredient or reactant of the invention employed refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term "about" also encompasses amounts that differ due to different equilibrium conditions for a composition resulting from a particular initial mixture. Whether or not modified by the term "about", the claims include equivalents to the quantities. In one embodiment, the term "about" means within 10% of the reported numerical value, preferably within 5% of the reported numerical value.

The term "carbon substrate" or "fermentable carbon substrate" refers to a carbon source capable of being metabolized by host organisms of the present invention and particularly carbon sources selected from the group consisting of monosaccharides, oligosaccharides, and polysaccharides.

"Gene" refers to a nucleic acid fragment that expresses a specific protein or functional RNA molecule, which may optionally include regulatory sequences preceding (5' non-coding sequences) and following (3' non-coding sequences) the coding sequence. "Native gene" or "wild type gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes.

The term "genetic construct" refers to a nucleic acid fragment that encodes for expression of one or more specific proteins or functional RNA molecules. In a gene construct the gene may be native, chimeric, or foreign in nature. Typically a genetic construct will comprise a "coding sequence". A "coding sequence" refers to a DNA sequence that encodes a specific amino acid sequence.

"Promoter" or "Initiation control regions" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters which cause a gene to be expressed in most cell types at most times are commonly referred to as "constitutive promoters".

The term "genetic modification" refers, non-inclusively, to any modification, mutation, base deletion, base addition, codon modification, gene over-expression, gene suppression, promoter modification or substitution, gene addition (either single or multicopy), antisense expression or suppression, or any other change to the genetic elements of a host cell or bacterial strain, whether they produce a change in phenotype or not.

The term "recombinant bacterial host cell" refers to a bacterial cell that comprises at least one heterologus gene or genetic construct or nucleic acid fragment.

The term "expression", as used herein, refers to the transcription and stable accumulation of coding (mRNA) or functional RNA derived from a gene. Expression may also refer to translation of mRNA into a protein. "Antisense inhibition" refers to the production of antisense RNA transcripts capable of suppressing the expression of the target protein. "Over-expression" refers to the production of a gene product in transgenic organisms that exceeds levels of production in normal or non-transformed organisms. "Co-suppression" refers to the production of sense RNA transcripts or fragments capable of suppressing the expression of identical or substantially similar foreign or endogenous genes (U.S. Pat. No. 5,231,020). The term "transformation" as used herein, refers to the transfer of a nucleic acid fragment into a host organism, resulting in genetically stable inheritance. The transferred nucleic acid may be in the form of a plasmid maintained in the host cell, or some transferred nucleic acid may be integrated into the genome of the host cell. Host organisms containing the transformed nucleic acid fragments are referred to as "transgenic" or "recombinant" or "transformed" organisms.

The terms "plasmid" and "vector" as used herein, refer to an extra chromosomal element often carrying genes which are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "selectable marker" means an identifying factor, usually an antibiotic or chemical resistance gene, that is able to be selected for based upon the marker gene's effect, i.e., resistance to an antibiotic, wherein the effect is used to track the inheritance of a nucleic acid of interest and/or to identify a cell or organism that has inherited the nucleic acid of interest.

As used herein the term "codon degeneracy" refers to the nature in the genetic code permitting variation of the nucleotide sequence without affecting the amino acid sequence of an encoded protein. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

The term "codon-optimized" as it refers to genes or coding regions of nucleic acid molecules for transformation of various hosts, refers to the alteration of codons in the gene or coding regions of the nucleic acid molecules to reflect the typical codon usage of the host organism without altering the protein encoded by the DNA.

The term "lignocellulosic" refers to a composition comprising both lignin and cellulose. Lignocellulosic material may also comprise hemicellulose.

The term "cellulosic" refers to a composition comprising cellulose and additional components, including hemicellulose.

The term "saccharification" refers to the production of fermentable sugars from polysaccharides.

The term "pretreated biomass" means biomass that has been subjected to physical, chemical and/or thermal pretreatment to increase accessibility of polysaccharides in the biomass prior to saccharification.

"Biomass" refers to any cellulosic or lignocellulosic material and includes materials comprising cellulose, and optionally further comprising hemicellulose, lignin, starch, oligosaccharides and/or monosaccharides. Biomass may also comprise additional components, such as protein and/or lipid. Biomass may be derived from a single source, or biomass can comprise a mixture derived from more than one source; for example, biomass could comprise a mixture of corn cobs and corn stover, or a mixture of grass and leaves. Biomass includes, but is not limited to, bioenergy crops, agricultural residues, municipal solid waste, industrial solid waste, sludge from paper manufacture, yard waste, wood and forestry waste. Examples of biomass include, but are not limited to, corn cobs, crop residues such as corn husks, corn stover, grasses, wheat straw, barley straw, hay, rice straw, switchgrass, waste paper, sugar cane bagasse, sorghum, soy, components obtained from milling of grains, trees, branches, roots, leaves, wood chips, sawdust, shrubs and bushes, vegetables, fruits, flowers and animal manure.

"Biomass hydrolysate" refers to the product resulting from saccharification of biomass. The biomass may also be pretreated or pre-processed prior to saccharification.

The term "xylose metabolic pathway" or "xylose utilization pathway" refers to a series of enzymes (encoded by genes) that metabolize xylose through to fructose-6-phosphate and/or glyceraldehyde-6-phosphate and include 1) xylose isomerase, which catalyses the conversion of xylose to xylulose; 2) xylulokinase, which phosphorylates xylulose to form xylulose 5-phosphate; 3) transketolase; and 4) transaldolase.

The term "xylose isomerase" refers to an enzyme that catalyzes the interconversion of D-xylose and D-xylulose. Xylose isomerases (XI) belong to the group of enzymes classified as EC 5.3.1.5.

The term "ribose-5-phosphate isomerase" or "RPI" refers to an enzyme that catalyzes the interconversion of ribulose-5-phosphate and ribose-5-phosphate. Ribose-5-phosphate isomerases belong to the group of enzymes classified as EC 5.3.1.6.

The term "E-value", as known in the art of bioinformatics, is "Expect-value" which provides the probability that a match will occur by chance. It provides the statistical significance of the match to a sequence. The lower the E-value, the more significant the hit.

The term "*Z. mobilis* RPI-A" refers to the *Z. mobilis* RPI which has been labeled in the art as RPI-A. However, the *Z. mobilis* RPI protein has closer sequence identity to the *E. coli* RPI-B protein (36%) than to the *E. coli* RPI-A protein (20%) and further analysis of RPIs described herein places the *Z. mobilis* RPI in the RPI-B group. However, herein the *Z. mobilis* RPI is called RPI-A to be consistent with its publicly known name.

The term "heterologous" means not naturally found in the location of interest. For example, a heterologous gene refers to a gene that is not naturally found in the host organism, but that is introduced into the host organism by gene transfer. For example, a heterologous nucleic acid molecule that is present in a chimeric gene is a nucleic acid molecule that is not naturally found associated with the other segments of the chimeric gene, such as the nucleic acid molecules having the coding region and promoter segments not naturally being associated with each other.

As used herein, an "isolated nucleic acid molecule" is a polymer of RNA or DNA that is single- or double-stranded, optionally containing synthetic, non-natural or altered nucleotide bases. An isolated nucleic acid molecule in the form of a polymer of DNA may be comprised of one or more segments of cDNA, genomic DNA or synthetic DNA.

A nucleic acid fragment is "hybridizable" to another nucleic acid fragment, such as a cDNA, genomic DNA, or RNA molecule, when a single-stranded form of the nucleic acid fragment can anneal to the other nucleic acid fragment under the appropriate conditions of temperature and solution ionic strength. Hybridization and washing conditions are well known and exemplified in Sambrook, J., Fritsch, E. F. and Maniatis, T. *Molecular Cloning: A Laboratory Manual,* 2$^{nd}$ ed., Cold Spring Harbor Laboratory: Cold Spring Harbor, N.Y. (1989), particularly Chapter 11 and Table 11.1 therein (entirely incorporated herein by reference). The conditions of temperature and ionic strength determine the "stringency" of the hybridization. Stringency conditions can be adjusted to screen for moderately similar fragments (such as homologous sequences from distantly related organisms), to highly similar fragments (such as genes that duplicate functional enzymes from closely related organisms). Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C. An additional set of stringent conditions include hybridization at 0.1×SSC, 0.1% SDS, 65° C. and washes with 2×SSC, 0.1% SDS followed by 0.1×SSC, 0.1% SDS, for example.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Sambrook et al., supra, 9.50-9.51). For hybridizations with shorter nucleic acids, i.e., oligonucleotides, the position of mismatches becomes more important, and the length of the oligonucleotide determines its specificity (see Sambrook et al., supra, 11.7-11.8). In one embodiment the length for a hybridizable nucleic acid is at least about 10 nucleotides. Preferably a minimum length for a hybridizable nucleic acid is at least about 15 nucleotides; more preferably at least about 20 nucleotides; and most preferably the length is at least about 30 nucleotides. Furthermore, the skilled artisan will recognize that the temperature and wash solution salt concentration may be adjusted as necessary according to factors such as length of the probe. The term "complementary" is used to describe the relationship between nucleotide bases that are capable of hybridizing to one another. For example, with respect to DNA, adenosine is complementary to thymine and cytosine is complementary to guanine.

The term "homologous" refers to nucleic acid fragments wherein changes in one or more nucleotide bases do not affect the ability of the nucleic acid fragment to mediate gene expression or produce a certain phenotype. The term also refers to modifications of the nucleic acid fragments of the instant invention such as deletion or insertion of one or more nucleotides that do not substantially alter the functional properties of the resulting nucleic acid fragment relative to the initial, unmodified fragment. It is therefore understood, as those skilled in the art will appreciate, that the invention encompasses more than the specific exemplary sequences.

Moreover, the skilled artisan recognizes that homologous nucleic acid sequences encompassed by this invention are also defined by their ability to hybridize, under moderately stringent conditions (e.g., 0.5×SSC, 0.1% SDS, 60° C.) with the sequences exemplified herein, or to any portion of the nucleotide sequences disclosed herein and which are functionally equivalent to any of the nucleic acid sequences disclosed herein.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: 1.) *Computational Molecular Biology* (Lesk, A. M., Ed.) Oxford University: NY (1988); 2.) *Biocomputing: Informatics and Genome Projects* (Smith, D. W., Ed.) Academic: NY (1993); 3.) *Computer Analysis of Sequence Data, Part I* (Griffin, A. M., and Griffin, H. G., Eds.) Humania: NJ (1994); 4.) *Sequence Analysis in Molecular Biology* (von Heinje, G., Ed.) Academic (1987); and 5.) *Sequence Analysis Primer* (Gribskov, M. and Devereux, J., Eds.) Stockton: NY (1991).

Preferred methods to determine identity are designed to give the best match between the sequences tested. Methods to determine identity and similarity are codified in publicly available computer programs. Sequence alignments and percent identity calculations may be performed using the MegAlign™ program of the LASERGENE bioinformatics computing suite (DNASTAR Inc., Madison, Wis.). Multiple alignment of the sequences is performed using the "Clustal method of alignment" which encompasses several varieties of the algorithm including the "Clustal V method of alignment" corresponding to the alignment method labeled Clustal V (described by Higgins and Sharp, *CABIOS.* 5:151-153 (1989); Higgins, D. G. et al., *Comput. Appl. Biosci.,* 8:189-191 (1992)) and found in the MegAlign™ program of the LASERGENE bioinformatics computing suite (DNASTAR Inc.). For multiple alignments, the default values correspond to GAP PENALTY=10 and GAP LENGTH PENALTY=10. Default parameters for pairwise alignments and calculation of percent identity of protein sequences using the Clustal method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences using the Clustal V program, it is possible to obtain a "percent identity" by viewing the "sequence distances" table in the same program. Additionally the "Clustal W method of alignment" is available and corresponds to the alignment method labeled Clustal W (described by Higgins and Sharp, *CABIOS.* 5:151-153 (1989); Higgins, D. G. et al., *Comput. Appl. Biosci.* 8:189-191 (1992)) and found in the MegAlign™ v6.1 program of the LASERGENE bioinformatics computing suite (DNASTAR Inc.). Default parameters for multiple alignment (GAP PENALTY=10, GAP LENGTH PENALTY=0.2, Delay Divergen Seqs(%)=30, DNA Transition Weight=0.5, Protein Weight Matrix=Gonnet Series, DNA Weight Matrix=IUB). After alignment of the sequences using the Clustal W program, it is possible to obtain a "percent identity" by viewing the "sequence distances" table in the same program.

It is well understood by one skilled in the art that many levels of sequence identity are useful in identifying polypeptides, from other species, wherein such polypeptides have the same or similar function or activity. Useful examples of percent identities include, but are not limited to: 25%, 30%, 35%, 40%, 45%, 50%, 55%, 60%, 65%, 70%, 75%, 80%, 85%, 90%, or 95%, or any integer percentage from 25% to 100% may be useful in describing the present invention, such as 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%. Suitable nucleic acid fragments not only have the above homologies but typically encode a polypeptide having at least 50 amino acids, preferably at least 100 amino acids, and more preferably at least 150 amino acids.

The term "sequence analysis software" refers to any computer algorithm or software program that is useful for the analysis of nucleotide or amino acid sequences. "Sequence analysis software" may be commercially available or independently developed. Typical sequence analysis software will include, but is not limited to: 1.) the GCG suite of programs (Wisconsin Package Version 9.0, Genetics Computer Group (GCG), Madison, Wis.); 2.) BLASTP, BLASTN, BLASTX (Altschul et al., J. Mol. Biol., 215:403-410 (1990)); 3.) DNASTAR (DNASTAR, Inc. Madison, Wis.); 4.) Sequencher (Gene Codes Corporation, Ann Arbor, Mich.); and 5.) the FASTA program incorporating the Smith-Waterman algorithm (W. R. Pearson, Comput. Methods Genome Res., [Proc. Int. Symp.] (1994), Meeting Date 1992, 111-20. Editor(s): Suhai, Sandor. Plenum: New York, N.Y.). Within the context of this application it will be understood that where sequence analysis software is used for analysis, that the results of the analysis will be based on the "default values" of the program referenced, unless otherwise specified. As used herein "default values" will mean any set of values or parameters that originally load with the software when first initialized.

Standard recombinant DNA and molecular cloning techniques used here are well known in the art and are described by Sambrook, J., Fritsch, E. F. and Maniatis, *T. Molecular Cloning: A Laboratory Manual,* $2^{nd}$ ed.; Cold Spring Harbor Laboratory: Cold Spring Harbor, N.Y., 1989 (hereinafter "Maniatis"); and by Silhavy, T. J., Bennan, M. L. and Enquist, L. W. *Experiments with Gene Fusions*; Cold Spring Harbor Laboratory: Cold Spring Harbor, N.Y., 1984; and by Ausubel, F. M. et al., In *Current Protocols in Molecular Biology*, published by Greene Publishing and Wiley-Interscience, 1987.

The present invention relates to engineered strains of xylose-utilizing *Zymomonas* or *Zymobacter* that have improved xylose utilization when fermented in xylose containing media. A challenge for improving ethanol production by fermentation of a biocatalyst in media that includes biomass hydrolysate, produced typically by pretreatment and saccharification of biomass, is obtaining optimal utilization of xylose. Xylose is one of the predominant pentose sugars in hydrolyzed lignocellulosic materials, the other being arabinose. Applicants have discovered that increased expression ribose-5-phosphate isomerase in xylose-utilizing strains leads to increased efficiency in xylose utilization, and thus to higher ethanol yields when fermentation is in xylose containing media.

Discovery of Inefficiency in Xylose Utilization

Figure 1:
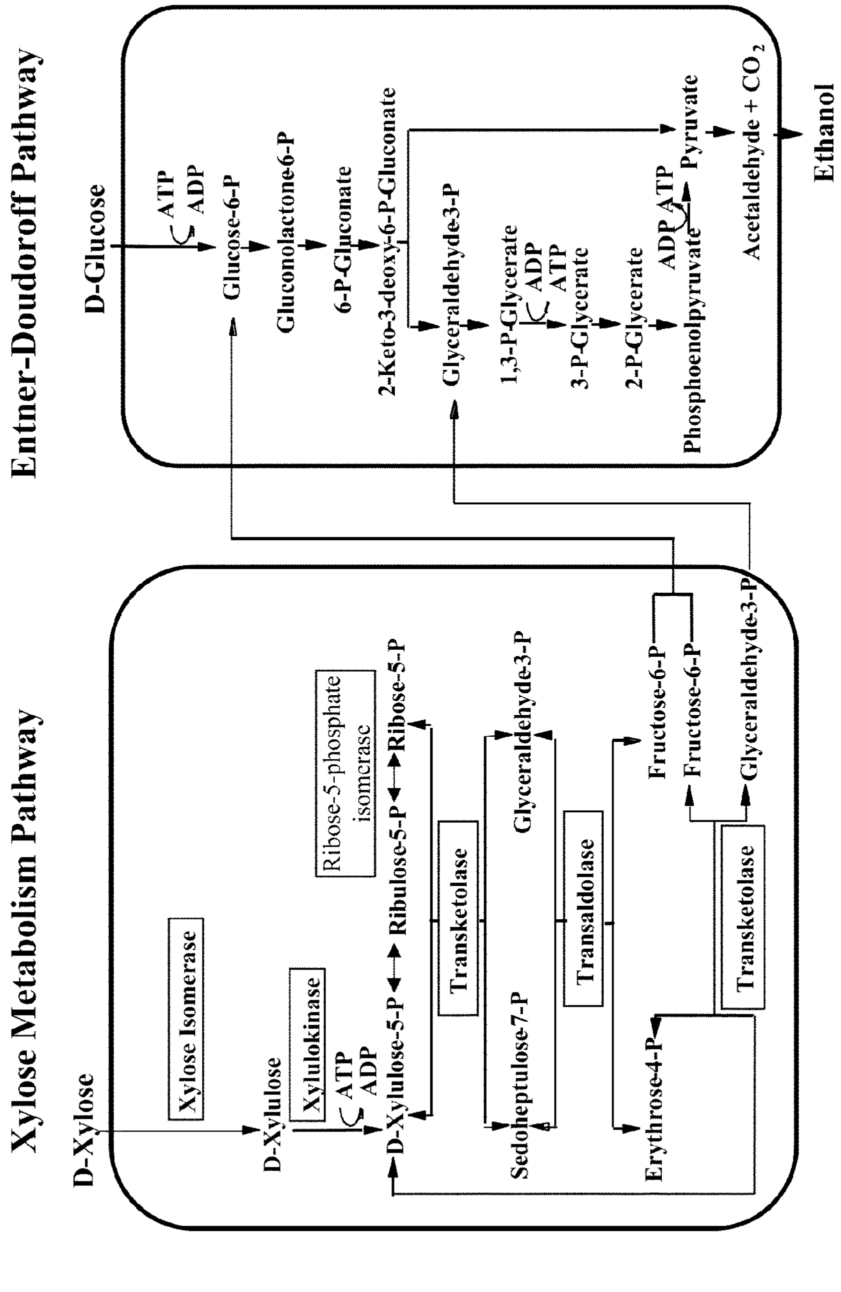
FIG. 1 shows a diagram of the xylose metabolism and ethanol fermentation pathways in *Zymomonas* engineered for xylose utilization.

Engineering of ethanologens for xylose utilization typically includes expression of four proteins: xylose isomerase, xylulokinase, transketolase, and transaldolase. These enzymes provide a xylose utilization pathway that feeds into ethanol production as shown in FIG. 1. However, utilization of xylose by *Zymomonas* strains engineered to metabolize xylose is typically not efficient.

Applicants have discovered a potential cause of inefficiency in xylose utilization: a xylose utilization pathway metabolite which could be used to produce ethanol is diverted to a by-product. Specifically, Applicants have discovered that with xylose-utilizing *Zymomonas* strains that are able to grow on xylose as the sole carbon source, ribulose (D-ribulose) accumulates in the medium when they are grown in medium containing only xylose as the carbon source. The ribulose accumulated in the medium may account for about 8% of total xylose consumed. This ribulose accumulation does not occur when the same xylose-utilizing *Zymomonas* is grown in medium containing glucose and no xylose.

Ribulose may be produced by conversion of ribulose-5-phosphate to ribulose by a phosphatase. If ribulose-5-phosphate accumulates in a cell it may provide a substrate for cellular phosphatases. The conversion of ribulose-5-phosphate to ribulose and accumulation of ribulose in the medium indicates an enzymatic deficiency in the pathway responsible for metabolizing xylose to ethanol. Conditions under which the initial step in metabolism of xylose, catalyzed by xylose isomerase, has been increased may act to intensify this deficiency leading to even higher levels of ribulose-5-phosphate and ribulose accumulation. In addition, ribulose-5-phosphate accumulation may be so great that it becomes bacteriostatic or even lethal, as it is known that sugar phosphate accumulation in bacteria cells is detrimental to their metabolism and viability. Therefore by the discovery of ribulose in the medium and Applicants' recognition of the potential implications of this finding, Applicants have identified a problem to be solved which may impact xylose utilization. Reducing production of ribulose and improving ribulose-5-phosphate utilization in xylose metabolism and ethanol production pathways as shown in FIG. 1 may improve production of ethanol from xylose.

Increasing Ribose-5-Phosphate Isomerase Activity

Applicants have discovered that increasing expression of ribose-5-phosphate isomerase (RPI) in xylose utilizing *Z. mobilis* that accumulates ribulose when grown in xylose containing medium leads to reduced accumulation of ribulose. Reduced accumulation of ribulose may be related to reduced accumulation of ribulose-5-phosphate as described above. Strains with increased RPI expression showed improved growth, increased xylose utilization, and increased ethanol production when grown in medium containing xylose as compared to the same strains lacking increased RPI expression. RPI catalyzes the interconversion of ribulose-5-phosphate and ribose-5-phosphate (see FIG. 1).

Increasing expression of the *Z. mobilis* RPI-A enzyme (which actually is an RPI-B as determined herein and described below) in a xylose utilizing *Z. mobilis* strain that produces ribulose when grown in xylose containing medium led to almost 50% reduction in ribulose accumulation in the medium as compared to the same strain without increased RPI expression. In addition, the strains with increased RPI expression showed increased cell mass yield, increased xylose consumption, and increased ethanol titer indicating increased conversion of xylose to ethanol. Increased expression of the *E. coli* RPI-A enzyme in the same ribulose producing *Z. molibilis* strain also led to production of increased cell mass. Increase in cell mass, xylose consumption, and ethanol yield will vary depending on factors such as the starting xylose-utilizing strain, media composition, and expression level of RPI. Increased cell mass may be about 15% or greater after 60 hours of growth in medium containing 100 g/L xylose as the sole sugar, and increase in ethanol production may be at least about 5%, using the present strains in conditions described in Examples herein.

Increased RPI expression may be accomplished using any protein or polypeptide with ribose-5-phosphate isomerase activity in *Zymomonas*. There are two groups of ribose-5-phosphate isomerase enzymes that are called RPI-A and RPI-B. The RPI-B enzymes belong to the RpiB/LacA/LacB family of sugar-phosphate isomerases. *E. coli* has two RPI proteins, one is an RPI-A and one is an RPI-B. *Z. mobilis* has a single RPI protein that is annotated as RPI-A. However, the *Z. mobilis* RPI protein has closer sequence identity to the *E. coli* RPI-B protein (36%) than to the *E. coli* RPI-A protein (20%). Further analysis of RPIs described below places the *Z. mobilis* RPI in the RPI-B group. However, herein the *Z. mobilis* RPI is called RPI-A to be consistent with its publicly known name.

The sequences of RPI proteins that may be used in the present microorganisms are very diverse as exemplified by the *Z. mobilis* and *E. coli* RPI proteins. RPI proteins that may be used in the present microorganisms may be identified using bioinformatics analysis. A structure/function bioinformatics approach used herein in Example 8 is analysis based on Profile Hidden Markov Modeling, active site residue identification, and additional identifying amino acid screening.

Profile Hidden Markov Models (HMM) were constructed using the hmmsearch algorithm of the HMMER software package (Janelia Farm Research Campus, Ashburn, Va.). The theory behind Profile HMMs is described in Durbin et al. ((1998) *Biological sequence analysis: probabilistic models of proteins and nucleic acids*, Cambridge University Press) and Krogh et al. ((1994) J. Mol. Biol. 235:1501-1531), which characterizes a set of proteins based on the probability of each amino acid occurring at each position in the alignment of the proteins of the set.

Proteins with functional identification as referenced in the BRENDA (Cologne University BioInformatics Center) and PubMed (US National Library of Medicine, National Institutes of Health) databases, 15 for RPI-A (Table 2; SEQ ID NOs:83, 84, 85, 86, 87, 88, 89, 90, 91, 92, 93, 94, 95, 96, and 97) and 5 for RPI-B (Table 3; SEQ ID NOs:1213, 1214, 1215, 1216, and 1217), were used as seed sequences to prepare Profile HMMs for RPI-A and RPI-B. BRENDA is a human-curated database that contains detailed information about enzyme kinetic, physical, and biochemical properties extracted from the experimental literature and with links to the relevant databases. Using each set of seed sequences a multiple sequence alignment (MSA) was built using ClustalW with default parameters. The MSA results were used as input data to prepare the Profile HMMs that are given in Tables 4 and 5 for ribose-5-phosphate isomerase A proteins and ribose-5-phosphate isomerase B proteins, respectively. In the tables, the amino acids are represented by the one letter code. The first line for each position reports the match emission scores: probability for each amino acid to be in that state (highest score is highlighted). The second line reports the insert emission scores, and the third line reports on state transition scores: M→M, M→I, M→D; I→M, I→I; D→M, D→D; B→M; M→E.

In addition to the Profile HMMs, active site residues known for RPI-A and RPI-B enzymes (Roos et al. (2004) J. Mol. Biol. 335:799-809; Graile et al. (2005) Biochimie 87:763-769), and an amino acid that distinguishes LacB, were used to identify RPI-A and RPI-B proteins that may be used in the present microorganisms. RPI-A proteins that may be used are proteins that i) give an E-value score of 0.1 or less when queried using a Profile Hidden Markov Model prepared using SEQ ID NOs:83, 84, 85, 86, 87, 88, 89, 90, 91, 92, 93, 94, 95, 96, and 97; the query being carried out using the hmmsearch algorithm wherein the Z parameter is set to 1 billion, and ii) have aspartic acid and glutamic acid at positions corresponding to 107 and 129, respectively, in the *Saccharomyces cerevisiae* RPI-A protein (SEQ ID NO:97). RPI-B proteins that may be used are proteins that i) give an E-value score of 0.1 or less when queried using a Profile Hidden Markov Model prepared using SEQ ID NOs:1213, 1214, 1215, 1216, and 1217; the query being carried out using the hmmsearch algorithm wherein the Z parameter is set to 1 billion, ii) either have cysteine and threonine at positions corresponding to 66 and 68, respectively, in the *E. coli* RPI-B protein (SEQ ID NO:1216) or have serine and glutamic acid at positions corresponding to 68 and 72, respectively, in the *M. tuberculosis* RPI-B protein (SEQ ID NO:1213), and iii) have asparagine, glycine, aspartic acid, serine, or glutamic acid but not leucine at the position corresponding to 100 in the *E. coli* RPI-B protein (SEQ ID NO:1216).

Examples of RPI-A and RPI-B proteins that fit the above criteria and that may be used in the present microorganisms are for RPI-A: SEQ ID NOs:83 through 1212, and for RPI-B:SEQ ID NOs:1213 through 2107. These proteins, as well as any protein with at least about 80-85%, 85%-90%, 90%-95%, or at least about 96%, 97%, 98%, or 99% sequence identity to any of these sequences and having ribose-5-phosphate isomerase activity, may be used in the present cells. Examples of sequences encoding RPI-A proteins include SEQ ID NOs: 2108 through 3237. Examples of sequences encoding RPI-B proteins include SEQ ID NOs:3238 through 4132. Additional RPIs may be readily identified in the literature and in bioinformatics databases as is well known to the skilled person and as described above. Identification of protein and/or coding sequences using bioinformatics is typically through BLAST (described above) searching of publicly available databases with RPI amino acid sequences or encoding sequences, such as those provided herein. Identities are based on the Clustal W method of alignment using the default parameters of GAP PENALTY=10, GAP LENGTH PENALTY=0.1, and Gonnet 250 series of protein weight matrix.

Additionally, the sequences described herein or those recited in the art may be used to identify other homologs in nature. For example each of the RPI encoding nucleic acid fragments described herein may be used to isolate DNA sequences encoding homologous proteins. Isolation of homologous sequences using sequence-dependent protocols is well known in the art. Examples of sequence-dependent protocols include, but are not limited to: 1) methods of nucleic acid hybridization; 2) methods of DNA and RNA amplification, as exemplified by various uses of nucleic acid amplification technologies [e.g., polymerase chain reaction (PCR), Mullis et al., U.S. Pat. No. 4,683,202; ligase chain reaction (LCR), Tabor, S. et al., *Proc. Acad. Sci. USA* 82:1074 (1985); or strand displacement amplification (SDA), Walker, et al., *Proc. Natl. Acad. Sci.* U.S.A., 89:392 (1992)]; and 3) methods of library construction and screening by complementation.

Xylose-Utilizing Host Strain

Expression of RPI may be increased in any strain of *Zymomonas* or other bacterial ethanolagen, such as *Zymobacter*, that is able to utilize xylose as a carbon source. *Zymobacter palmae* is an ethanol-producing bacterium that has been engineered for xylose utilization by expressing genes for xylose utilization as described below for *Zymomonas*, using *Z. mobilis* glyceraldehyde-3-phosphate dehydrogenase and enolase promoters (Yanase et al. *Applied and Environmental Microbiology* (2007) 73:2592-2599). In addition, the ethanologen accumulates ribulose-5-phosphate or ribulose when grown in medium containing xylose when RPI expression is not increased.

Strains of *Zymomonas*, such as *Z. mobilis* have been engineered for xylose fermentation to ethanol. Typically four genes have been introduced into *Z. mobilis* for expression of four enzymes involved in xylose metabolism (FIG. 1) as described in U.S. Pat. No. 5,514,583, U.S. Pat. No. 5,712,133, U.S. Pat. No. 6,566,107, WO 95/28476, Feldmann et al. ((1992) Appl Microbiol Biotechnol 38: 354-361), and Zhang et al. ((1995) Science 267:240-243). These include genes encoding xylose isomerase which catalyzes the conversion of xylose to xylulose, and xylulokinase which phosphorylates xylulose to form xylulose 5-phosphate. Additionally expressed are transketolase and transaldolase, two enzymes of the pentose phosphate pathway that convert xylulose 5-phosphate to intermediates that couple pentose metabolism to the glycolytic Entner-Douderoff pathway permitting the metabolism of xylose to ethanol (see FIG. 1). DNA sequences encoding these enzymes may be obtained from any of numerous microorganisms that are able to metabolize xylose, such as enteric bacteria, and some yeasts and fungi. Sources for the coding regions may include *Xanthomonas, Klebsiella, Escherichia, Rhodobacter, Flavobacterium, Acetobacter, Gluconobacter, Rhizobium, Agrobacterium, Salmonella, Pseudomonads*, and *Zymomonas*. The coding regions of *E. coli* are typically used.

Endogenous genes may provide part of a xylose fermentation pathway, or may be altered by any known genetic manipulation technique to provide a protein with enzyme activity useful for xylose metabolism. For example, the endogenous transketolase may complement other introduced enzyme activities in creating a xylose utilization pathway.

*Zymomonas* or *Zymobacter* strains that are additionally engineered to utilize other sugars that, like xylose, are not natural substrates, may also be used in the present process. An example is a strain of *Z. mobilis* engineered for arabinose utilization as described in U.S. Pat. No. 5,843,760, which is herein incorporated by reference. Strains may be modified in other additional ways to improve xylose utilization and ethanol production.

Increased Expression of RPI

In the present microorganism, a genetic modification is made which increases ribose-5-phosphate isomerase activity as compared to ribose-5-phosphate isomerase activity in the microorganism lacking the genetic modification. Increased expression of RPI activity may be obtained by expressing a DNA molecule encoding a protein having ribose-5-phosphate isomerase activity that is active in the host microorganism. Useful proteins with ribose-5-phosphate isomerase activity including ribose-5-phosphate isomerase A and ribose-5-phosphate isomerase B proteins are described above.

Any method for increasing activity of an enzyme in a microorganism may be used to increase RPI activity. Such methods are well known to one skilled in the art and include increasing the encoding gene copy number and/or expression from a gene containing a high expression promoter. The present strains may be engineered for increased expression of an endogenous RPI coding region, and/or expression of an introduced heterologous RPI coding region to give increased enzyme activity. In addition, RPI activity may be increased by mutation and screening of expressed mutated genes to identify microorganisms with increased activity.

Typically, increased expression of RPI is achieved by transforming with a DNA molecule encoding RPI that is operably linked to a promoter in a chimeric gene or operon. Coding sequences for RPIs that may be used include any sequences encoding the RPI-A and RPI-B proteins described above. Examples of these coding sequences include for RPI-A: SEQ ID NOs:2108 through 3237, and for RPI-B: SEQ ID NOs:3238 through 4132.

When using a heterologous coding region, the sequence may be codon-optimized for maximal expression in the target host cell, as well known to one skilled in the art. If the native start codon is GTG, it may be changed to ATG for increased protein expression. Methods for gene expression in bacteria are well known in the art. Expression of genes in bacteria typically requires a promoter, operably linked to a coding region of interest, and a transcriptional terminator. Promoters that may be used are promoters that are expressed in *Zymomonas* or *Zymobacter* cells such as the promoters of *Z. mobilis* glyceraldehyde-3-phosphate dehydrogenase (GAP promoter; $P_{gap}$) gene, of *Z. mobilis* enolase (ENO promoter; Peno) gene, and of the *Actinoplanes missouriensis* xylose isomerase encoding gene (GI promoter, Pgi). Particularly high expression promoters that may be used are the $P_{gap}$ promoters with mutations causing high expression as disclosed in US Patent Publication #2009-0246876 A1. The $P_{gap}$ promoters therein have a base substitution in a position selected from the group consisting of position −190, position −89, or both position −190 and −89; wherein the position numbers are with respect to the natural ATG translation initiation codon for glyceraldehyde-3-phosphate dehydrogenase in the CP4 and ZM4 strains of *Z. mobilis*. Specifically, the base substitution is at position −190, a T replacing G; and at position −89, a T replacing C. These positions are 116 and 217, respectively, in SEQ ID NO:17.

A chimeric gene or operon for RPI expression is typically constructed in or transferred to a vector for further manipulations. Vectors are well known in the art. Certain vectors are capable of replicating in a broad range of host bacteria and can be transferred by conjugation. The complete and annotated sequence of pRK404 and three related vectors: pRK437, pRK442, and pRK442(H) are available. These derivatives have proven to be valuable tools for genetic manipulation in gram-negative bacteria (Scott et al., *Plasmid* 50(1):74-79 (2003)). Particularly useful for expression in *Zymomonas* are vectors that can replicate in both *E. coli* and *Zymomonas*, such as pZB188 which is described in U.S. Pat. No. 5,514,583. Vectors may include plasmids for autonomous replication in a cell, and plasmids for carrying constructs to be integrated into bacterial genomes. Plasmids for DNA integration may include transposons, regions of nucleic acid sequence homologous to the target bacterial genome, or other sequences supporting integration. An additional type of vector may be a transposome produced using, for example, a system that is commercially available from EPICENTRE®. It is well known how to choose an appropriate vector for the desired target host and the desired function.

Bacterial cells may be engineered by introducing a vector having a chimeric gene comprising an RPI coding region by well known methods, such as using freeze-thaw transformation, calcium-mediated transformation, electroporation, or conjugation. Any bacterial cell to be engineered for improved xylose utilization by increasing expression of an RPI enzyme is a target host cell for transformation to engineer a strain as described herein. Particularly suitable host cells are *Zymomonas* and *Zymobacter*. The introduced chimeric gene may be maintained in the cell on a stably replicating plasmid, or integrated into the genome following introduction.

For engineering a strain with an integrated RPI chimeric gene or operon in the bacterial cell genome, methods may be used that are well known in the art such as homologous recombination, transposon insertion, or transposome insertion. In homologous recombination, DNA sequences flanking a target integration site are placed bounding a spectinomycin-resistance gene, or other selectable marker, and Rpi chimeric gene leading to insertion of the selectable marker and the Rpi chimeric gene into the target genomic site. In addition, the selectable marker may be bounded by site-specific recombination sites, so that after expression of the corresponding site-specific recombinase, the resistance gene is excised from the genome.

In addition, the promoter of the endogenous RPI expressing gene may be replaced with a more highly expressed promoter to increase RPI activity in the cell. This may be accomplished by homologous recombination using vectors and methods as described above.

Combination of Increased Xylose Isomerase and RPI Expression

The present microorganisms may be engineered to have increased expression of xylose isomerase. The presence of increased RPI activity in the cells, along with further increased xylose isomerase expression, leads to further increased ethanol production. For example, ethanol production may be increased by at least about 10%, 15%, 20%, or 25%, depending on factors such as the specific strain, media composition, and growth conditions.

In the present cells, increased expression of xylose isomerase activity may be obtained by expressing a gene encoding a xylose isomerase enzyme that is active in the host cell, using any method known in the art as described above for expression of RPI. Useful enzymes with xylose isomerase activity are described in commonly owned and co-pending US Patent Application Publication US 2009-0246846 A1, which is herein incorporated by reference. As disclosed therein xylose isomerases may be identified using a Profile HMM (described above for RPI) prepared therein using 32 xylose isomerase protein sequences with experimentally verified function as referenced in the BRENDA database. These proteins are listed in Table 1 and have SEQ ID NOs:19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, and 81. The Profile HMM for the xylose isomerase family of proteins is given in Table 3. In addition to the Profile HMM, four catalytic site amino acids were found to be characteristic of xylose isomerases: histine 54, aspartic acid 57, glutamic acid 181, and lysine 183, with the position numbers in reference to the *Streptomyces albus* xylose isomerase sequence (SEQ ID NO:61). Any protein fitting the xylose isomerase Profile HMM with an E-value score < or $=3\times10^{-10}$ and having these four catalytic site residues is a xylose isomerase whose coding region may be used to increase xylose isomerase activity in the present cells, in addition to the proteins with SEQ ID NOs listed in Table 1. Examples of coding regions that may be used to express xylose isomerase proteins are SEQ ID NOs: 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80 as listed in Table 1.

As known in the art, there may be variations in DNA sequences encoding an amino acid sequence due to the degeneracy of the genetic code. Codons may be optimized for expression of an amino acid sequence in a target host cell to provide for optimal encoded expression.

Fermentation of Improved Xylose-Utilizing Strain

The present engineered microorganisms with increased RPI activity may be used in fermentation to produce ethanol. As an example, production of ethanol by a *Z. mobilis* strain of the invention is described.

For production of ethanol, recombinant xylose-utilizing *Z. mobilis* having increased RPI activity is brought in contact with medium that contains xylose. Xylose may be the sole sugar, but typically the medium contains a mixture of sugars including xylose and glucose. The medium may contain biomass hydrolysate that includes these sugars that are derived from treated cellulosic or lignocellulosic biomass.

When the mixed sugars concentration is high such that growth is inhibited, the medium includes sorbitol, mannitol, or a mixture thereof as disclosed in commonly owned U.S. Pat. No. 7,629,156 B2. Galactitol or ribitol may replace or be combined with sorbitol or mannitol. The *Z. mobilis* grows in the medium where fermentation occurs and ethanol is produced. The fermentation is run without supplemented air, oxygen, or other gases (which may include conditions such as anaerobic, microaerobic, or microaerophilic fermentation), for at least about 24 hours, and may be run for 30 or more hours. The timing to reach maximal ethanol production is variable, depending on the fermentation conditions. Typically, if inhibitors are present in the medium, a longer fermentation period is required. The fermentations may be run at temperatures that are between about 30° C. and about 37° C., at a pH of about 4.5 to about 7.5.

The present *Z. mobilis* may be grown in medium containing mixed sugars including xylose in laboratory scale fermenters, and in scaled up fermentation where commercial quantities of ethanol are produced. Where commercial production of ethanol is desired, a variety of culture methodologies may be applied. For example, large-scale production from the present *Z. mobilis* strains may be produced by both batch and continuous culture methodologies. A classical batch culturing method is a closed system where the composition of the medium is set at the beginning of the culture and not subjected to artificial alterations during the culturing process. Thus, at the beginning of the culturing process the medium is inoculated with the desired organism and growth or metabolic activity is permitted to occur adding nothing to the system. Typically, however, a "batch" culture is batch with respect to the addition of carbon source and attempts are often made at controlling factors such as pH and oxygen concentration. In batch systems the metabolite and biomass compositions of the system change constantly up to the time the culture is terminated. Within batch cultures cells moderate through a static lag phase to a high growth log phase and finally to a stationary phase where growth rate is diminished or halted. If untreated, cells in the stationary phase will eventually die. Cells in log phase are often responsible for the bulk of production of end product or intermediate in some systems. Stationary or post-exponential phase production can be obtained in other systems.

A variation on the standard batch system is the Fed-Batch system. Fed-Batch culture processes are also suitable for growth of the present *Z. mobilis* strains and comprise a typical batch system with the exception that the substrate is added in increments as the culture progresses. Fed-Batch systems are useful when catabolite repression is apt to inhibit the metabolism of the cells and where it is desirable to have limited amounts of substrate in the medium. Measurement of the actual substrate concentration in Fed-Batch systems is difficult and is therefore estimated on the basis of the changes of measurable factors such as pH and the partial pressure of waste gases such as $CO_2$. Batch and Fed-Batch culturing methods are common and well known in the art and examples may be found in Biotechnology: A Textbook of Industrial Microbiology, Crueger, Crueger, and Brock, Second Edition (1989) Sinauer Associates, Inc., Sunderland, Mass., or Deshpande, Mukund V., *Appl. Biochem. Biotechnol.,* 36, 227, (1992), herein incorporated by reference.

Commercial production of ethanol may also be accomplished with a continuous culture. Continuous cultures are open systems where a defined culture medium is added continuously to a bioreactor and an equal amount of conditioned medium is removed simultaneously for processing. Continuous cultures generally maintain the cells at a constant high liquid phase density where cells are primarily in log phase growth. Alternatively, continuous culture may be practiced with immobilized cells where carbon and nutrients are continuously added, and valuable products, by-products or waste products are continuously removed from the cell mass. Cell immobilization may be performed using a wide range of solid supports composed of natural and/or synthetic materials as is known to one skilled in the art.

Continuous or semi-continuous culture allows for the modulation of one factor or any number of factors that affect cell growth or end product concentration. For example, one method will maintain a limiting nutrient such as the carbon source or nitrogen level at a fixed rate and allow all other parameters to moderate. In other systems a number of factors affecting growth can be altered continuously while the cell concentration, measured by medium turbidity, is kept constant. Continuous systems strive to maintain steady state growth conditions and thus the cell loss due to medium being drawn off must be balanced against the cell growth rate in the culture. Methods of modulating nutrients and growth factors for continuous culture processes as well as techniques for maximizing the rate of product formation are well known in the art of industrial microbiology and a variety of methods are detailed by Brock, supra.

Particularly suitable for ethanol production is a fermentation regime as follows. The desired *Z. mobilis* strain of the present invention is grown in shake flasks in semi-complex medium at about 30° C. to about 37° C. with shaking at about 150 rpm in orbital shakers and then transferred to a 10 L seed fermentor containing similar medium. The seed culture is grown in the seed fermentor anaerobically until $OD_{600}$ is between 3 and 6, when it is transferred to the production fermentor where the fermentation parameters are optimized for ethanol production. Typical inoculum volumes transferred from the seed tank to the production tank range from about 2% to about 20% v/v. Typical fermentation medium contains minimal medium components such as potassium phosphate (1.0-10.0 g/L), ammonium sulfate (0-2.0 g/L), magnesium sulfate (0-5.0 g/L), a complex nitrogen source such as yeast extract or soy based products (0-10 g/L). A final concentration of about 5 mM sorbitol or mannitol is present in the medium. Mixed sugars including xylose and at least one additional sugar such as glucose (or sucrose), providing a carbon source, are continually added to the fermentation vessel on depletion of the initial batched carbon source (50-200 g/L) to maximize ethanol rate and titer. Carbon source feed rates are adjusted dynamically to ensure that the culture is not accumulating glucose in excess, which could lead to build up of toxic byproducts such as acetic acid. In order to maximize yield of ethanol produced from substrate utilized, biomass growth is restricted by the amount of phosphate that is either batched initially or that is fed during the course of the fermentation. The fermentation is controlled at pH 5.0-6.0 using caustic solution (such as ammonium hydroxide, potassium hydroxide, or sodium hydroxide) and either sulfuric or phosphoric acid. The temperature of the fermentor is controlled at 30° C.-35° C. In order to minimize foaming, antifoam agents (any class-silicone based, organic based etc) are added to the vessel as needed. An antibiotic, for which there is an antibiotic resistant marker in the strain, such as kanamycin, may be used optionally to minimize contamination.

Any set of conditions described above, and additionally variations in these conditions that are well known in the art, are suitable conditions for production of ethanol by a xylose-utilizing recombinant *Zymomonas* strain.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

General Methods

Standard recombinant DNA and molecular cloning techniques used here are well known in the art and are described by Sambrook, J., Fritsch, E. F. and Maniatis, T., *Molecular Cloning: A Laboratory Manual,* $2^{nd}$ ed., Cold Spring Harbor Laboratory: Cold Spring Harbor, N.Y. (1989) (hereinafter "Maniatis"); and by Silhavy, T. J., Bennan, M. L. and Enquist, L. W., *Experiments with Gene Fusions*, Cold Spring Harbor Laboratory: Cold Spring Harbor, N.Y. (1984); and by Ausubel, F. M. et al., *Current Protocols in Molecular Biology*, published by Greene Publishing Assoc. and Wiley-Interscience, Hoboken, N.J. (1987).

The meaning of abbreviations is as follows: "kb" means kilobase(s), "bp" means base pairs, "nt" means nucleotide(s), "hr" means hour(s), "min" means minute(s), "sec" means second(s), "d" means day(s), "L" means liter(s), "ml" means milliliter(s), "4" means microliter(s), "4" means microgram(s), "ng" means nanogram(s), "mM" means millimolar, "μM" means micromolar, "nm" means nanometer(s), "μmol" means micromole(s), "μmol" means picomole(s), "Cm" means chloramphenicol, "$Cm^r$" means chloramphenicol resistant, "$Cm^s$" means chloramphenicol sensitive, "$Sp^r$" means spectinomycin resistance, "$Sp^s$" means spectinomycin sensitive, "XI" is xylose isomerase, "XK" is xylulokinase, "TAL" is transaldolase, "TKT" is transketolase, "OD600" means optical density measured at a wavelength of 600 nm, "PCR" means polymerase chain reaction, "kDa" means kilodaltons, "g" means the gravitation constant, "bp" means base pair(s), "kbp" means kilobase pair(s), "HPLC" means high performance liquid chromatography, and "GC" means gas chromatography, "RM" means rich medium containing 10 g/L yeast extract plus 2 g/L $KH_2PO_4$, "MM" means mating medium containing 10 g/L yeast extract, 5 g/L tryptone, 2.5 g/L $(NH_4)_2SO_4$ and 0.2 g/L $KH_2PO_4$.

Example 1

Ribulose Accumulation *Zymomonas mobilis* Strain ZW801-4

The recombinant *Z. mobilis* strain ZW801-4 was described in U.S. Pat. No. 7,741,119, which is herein incorporated by reference. Strain ZW801-4 was derived from strain ZW800, which was derived from strain ZW658, all as described in U.S. Pat. No. 7,741,119. ZW658 was constructed by integrating two operons, $P_{gap}$xylAB and $P_{gap}$taltkt, containing four xylose-utilizing genes encoding xylose isomerase (xylA), xylulokinase (xylB), transaldolase (tal), and transketolase (tkt), into the genome of ZW1 (rename of strain ZM4; ATCC #31821) via sequential transposition events to produce strain X13L3, which was renamed ZW641, and followed by adaptation on selective media containing xylose. ZW658 was deposited under the Budapest Treaty as ATCC #PTA-7858. In ZW658, the gene encoding glucose-fructose oxidoreductase was insertionally-inactivated using host-mediated, double-crossover, homologous recombination and spectinomycin resistance as a selectable marker to create strain ZW800. The spectinomycin resistance marker, which was bounded by loxP sites, was removed by site specific recombination using Cre recombinase to create strain ZW801-4. As disclosed in commonly owned and co-pending US Patent Application Publication #US 20090246846 A1, ZW648 has much more xylose isomerase activity (about 7-fold higher) than ZW641 (represented by X13bC strain) due to a mutation in the promoter (Pgap) expressing the xylA coding region.

Figure 2:
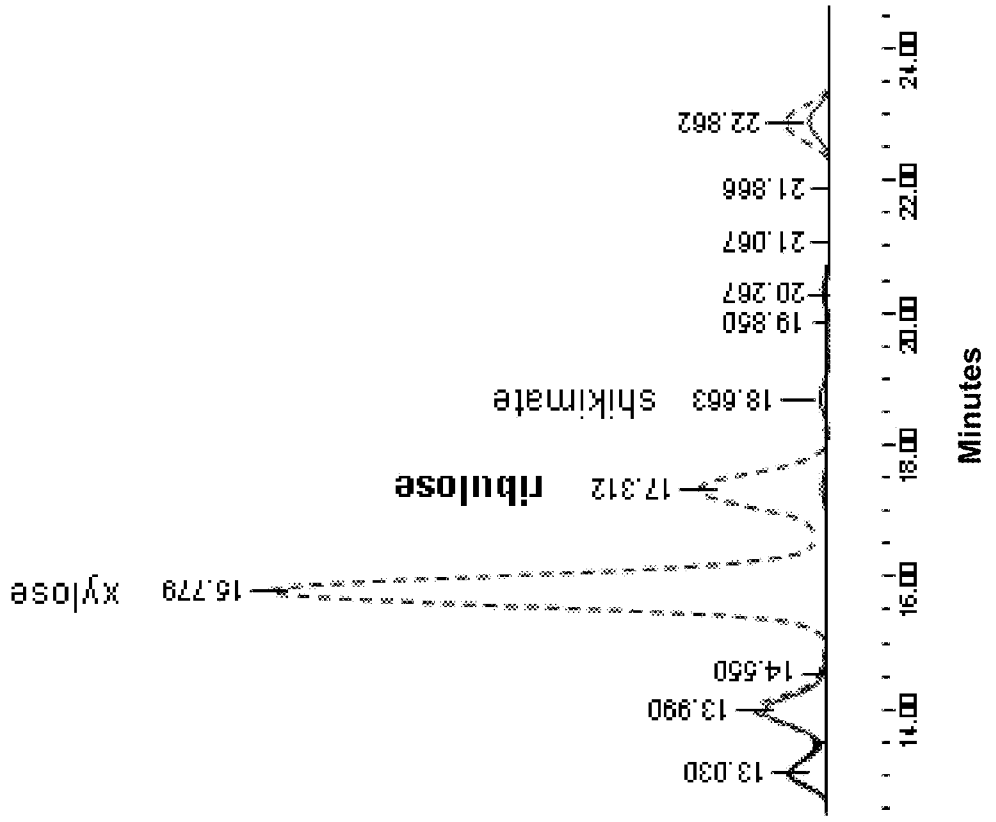
FIG. 2 shows HPLC analysis of culture media following growth of strain ZW801-4 in media containing glucose (solid line) or xylose (dashed line).

ZW801-4 was grown in medium containing xylose as the sole carbon source (MRM3X10 media; 1% yeast extract, 15 mM $KH_2PO_4$, 4 mM $MgSO_4$, and 100 g/L xylose) and in medium with 100 g/L glucose substituted for the xylose (MRM3G10). Cells were grown at 33° C. with minimal agitation (125 RPM in a LAB-Line orbital shaker; Terra Universal, Inc. Fullerton, Calif.). Ribulose and other fermentation products were analyzed by high performance chromatography (HPLC). HPLC analysis was performed on an Agilent 1200 series (Agilent Technologies, Santa Clara, Calif.) with both refractive index and diode array detectors. Mobile phase consisted of 0.01N sulfuric acid at 0.5 ml/min. A Shodex SH1011 (Showa Denko, Tokyo, Japan) sugar column was used for separation of substrates and fermentation products. External standards included D-glucose, D-xylose, glycerol, acetate, ethanol and D-ribulose (Sigma-Aldrich, St. Louis, Mo.) at various concentrations for calibration and comparison to products accumulating in culture media. The refractive index signal for the D-ribulose standard was at a retention time of 17.3 minutes and, as expected, presents no signal with diode array detection. Analysis of culture media showed ribulose production began very early in the xylose containing culture and continued until the xylose source had been exhausted. Furthermore, ribulose accumulated only when cells were grown in xylose containing media (FIG. 2, dashed line). Comparison of culture media by HPLC for the strain ZW801-4 grown in culture media with glucose as the carbon source (FIG. 2, solid line) showed neither transient nor cumulative production of ribulose despite complete use of this substrate (FIG. 2). Xylose was not used to completion in the culture containing xylose medium.

Example 2

Engineering of *Z. Mobilis* with Chimeric *Z. Mobilis* Ribulose-5-Phosphate Isomerase Gene Expression of an extrachromosomal copy of a chimeric gene containing the native *Z. mobilis* ribulose-5-phosphate isomerase (RPI-A) coding region was accomplished by cloning the coding region into a shuttle vector adjacent to a glucose isomerase (GI) promoter derived from *Actinoplanes missouriensis*.

The *Z. mobilis* RPI-A coding region (SEQ ID NO:1870) was isolated from strain ZW1 (rename of strain ZM4; ATCC 31821) genomic DNA using PCR. Genomic DNA was prepared from ZW1 using a Puregene genomic DNA purification kit following the manufacturer's instructions (Gentra Systems, Minneapolis, Minn.). PCR primers were designed to amplify the RPI-A coding region and incorporate appropriate restriction enzyme sites for cloning purposes. PCR primers were also designed to preserve the native distance between the promoter's Shine-Delgarno sequence and the coding region initiation codon.

PCR primers used to isolate the RPI-A coding region were Primer-1 and Primer-2 (SEQ ID NOs:1 and 2). The sequence of Primer-1 corresponds to the 5'-end of the RPI-A coding region, including the native initiation codon and 15 bp of sequence at the extreme 3'-end of the *A. missouiensis* GI promoter. Primer-2 includes the 3'-end of the RPI-A coding region, incorporating the native STOP codon and a XhoI restriction enzyme recognition site. PCR using genomic DNA from *Z. mobilis* ZW1 with Primer-1 and Primer-2 resulted in a DNA fragment containing the 474 bp RPI-A coding sequence, with 15 bp of the GI promoter sequence at the 5'-end and an XhoI restriction enzyme recognition site at the 3'-end.

The 186 bp *A. missouriensis* (ATCC 14538) GI promoter (SEQ ID NO:14) was isolated by PCR using primers Primer-3 and Primer-4 (SEQ ID NOs:3 and 4). The PCR Primer-3 contains sequence for NcoI and SacI restriction enzyme recognition sites located at the 5'-end of the GI promoter fragment. The sequence for Primer-4 contains the 3'-end of the GI promoter and the first 15 bp for the RPI-A coding sequence.

The GI promoter and RPI-A coding sequence PCR products were combined in a second PCR using only the primers Primer-2 and Primer-3, which resulted in a DNA fragment containing the GI promoter linked to the RPI-A coding sequence with the distance between the Shine-Delgarno sequence and initiation codon preserved. The DNA fragment was then digested with the restriction enzymes NcoI and XhoI and ligated into the *Zymomonas*-*E. coli* shuttle vector pZB188/aadA previously treated with the same two enzymes. pZB188/aadA (SEQ ID NO:15) is a vector constructed from pZB188, described in U.S. Pat. No. 5,514,583, which is able to replicate in *E. coli* and *Z. mobilis*, and has a tetracycline resistance marker. Construction of pZB188/aadA was described in commonly owned and co-pending US Patent Application Publication US 2009-0246876 A1 (Example 5, which is herein incorporated by reference), and has a deletion of the tetracycline resistance marker and replacement with a spectinomycin resistance marker. Following ligation, the resulting plasmid, designated pZB-GI-RPI (SEQ ID NO:16), was transformed into chemically competent *E. coli* SCS110 cells (Stratagene, San Diego, Calif.) using the manufacturer's protocol.

The plasmid pZB-GI-RPI isolated from SCS110 cells was transformed into competent *Z. molilis* strain ZW801-4. Competent ZW801-4 cells were prepared by growing cultures overnight in MRM3G5 (1% yeast extract, 15 mM $KH_2PO_4$, 4 mM $MgSO_4$, and 50 g/L glucose) at 30° C. Cells were harvested the next day and transferred to fresh medium to an initial OD600 value of 0.025. Cultures were grown to an OD600 of 0.5, then harvested and washed once with 4° C. sterile-filtered water and then twice with 4° C. 10% glycerol. Competent cells, concentrated by a factor of 200× (OD600=100), were stored at −80° C. until use.

Transformed *Z. molilis* strains containing the pZB-GI-RPI plasmid were isolated from single colonies following incubation on MRM3G5-Spec250 plates (MRM3G5 media with 250 mg/L spectinomycin and 15 g/L agar) incubated for 2 days at 30° C., in an anaerobic jar using AnaeroPacks (Mitsubishi Gas Chemical, New York, N.Y.).

Example 3

Effects of Increased Expression of *Z. Mobilis* Ribulose-5-Phosphate Isomerase in Recombinant *Z. Mobilis* Strains To determine whether recombinant *Z. mobilis* strains carrying extrachromosomal copies of the RPI-A gene would have altered levels of ribulose and improved xylose fermentation, individual transformed strains containing pZB-GI-RPI were selected from MRM3G5-Spec250 plates. Transformed strains (RPI-1 and RPI-2) were transferred to MRM3G5-Spec250 liquid media at a 0.1 initial OD600 and incubated at 30° C. After 14-16 hours incubation, strains were transferred to MRM3X10 medium (1% yeast extract, 15 mM $KH_2PO_4$, 4 mM $MgSO_4$, and 100 g/L xylose) and incubated for 24 hours. Testing the effect of increased RPI-A gene copy number on fermentation performance began after a second transfer of cultures to fresh MRM3X10 medium as a measure to prevent glucose carry-over from the original culture. Transformed strains carrying pZB-GI-RPI and controls (ZW801-4 in duplicate: ZW801-1 and ZW801-2) were inoculated to an initial OD600 of 0.1 and incubated at 30° C. Growth was monitored by optical density measurements. Xylose consumption and product accumulation (i.e. ribulose and ethanol) were monitored by HPLC analysis as described in Example 1.

Figure 3:
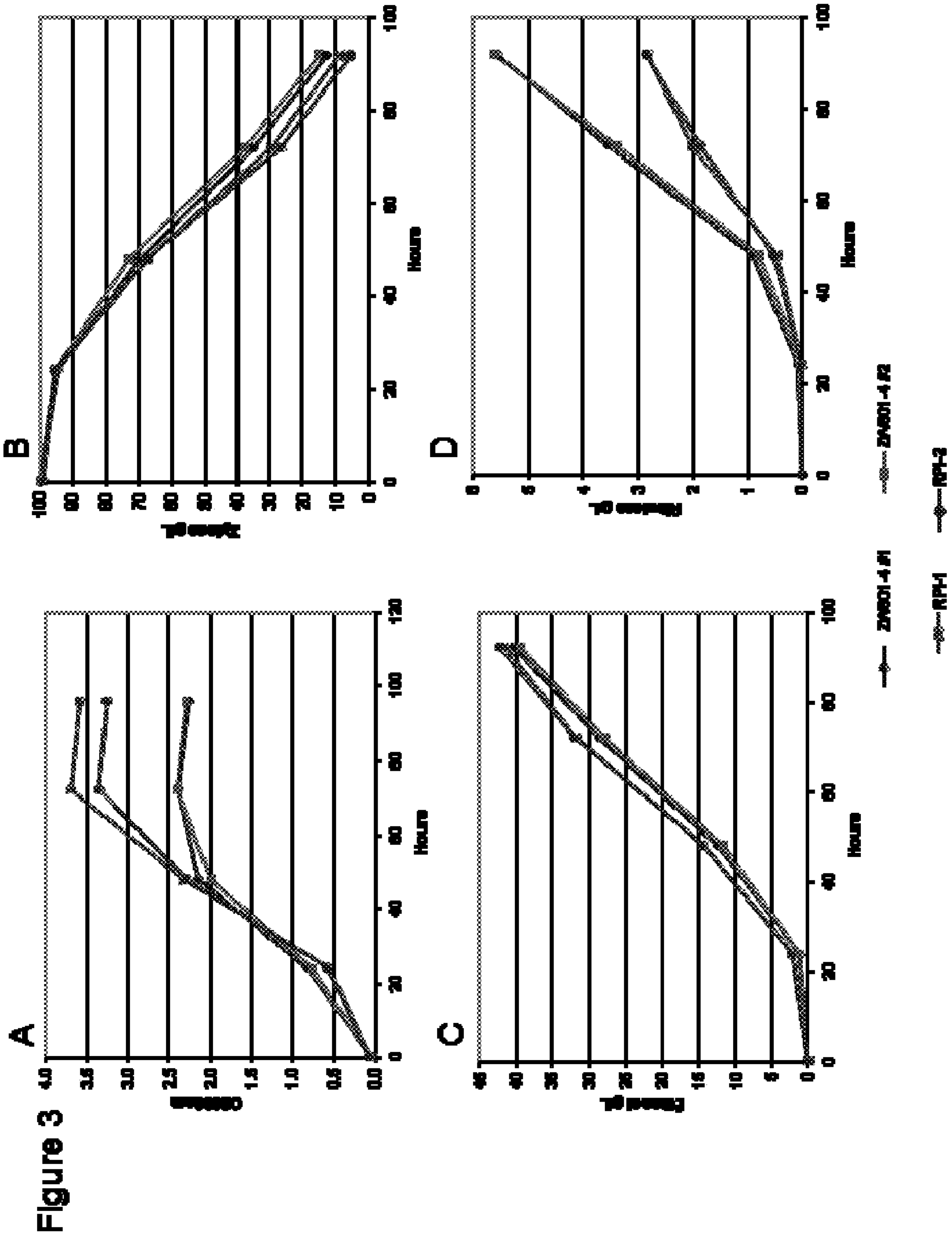
FIG. 3 shows graphs of growth (A), xylose utilization (B), ethanol production (C), and ribulose accumulation in media (D) of cultures of ZW801-4 control strains (ZW801-4#1 and ZW801-4#2) and ZW801-4 strains containing a plasmid containing a chimeric gene with an *A. missouriensis* GI promoter and *Z. mobilis* RPI-A coding region (RPI-1 and RPI-2).

The results for fermentation in MRM3X10 medium are shown in FIG. 3 (A-C). FIG. 3A is a record of the change in optical density for two transformed strains (RPI-1 and RPI-2) compared to the controls (ZW801-4#1 and ZW801-4#2). From this data it can be seen that early growth of the transformed and control strains was similar. However, at the 48-hour time point the control strain ceased growing, whereas the two independent transformed strains continued to increase in cell mass. The increase in cell mass accumulated by the strains carrying extra copies of the *Z. mobilis* RPI-A coding region was also reflected in the increased use of xylose and increase in ethanol production over the later time-points for this experiment (FIGS. 3B and 3C). FIG. 3D also shows the time course for ribulose accumulation for each strain. From this data it is clear that the level of ribulose was reduced for the recombinant strains containing additional *Z. mobilis* RPI-A coding region copies, compared to controls.

Example 4

Expression of the *E. Coli* RPI-A Gene in Recombinant *Zymomonas mobilis*

The RPI-A coding region was cloned from *E. coli* (coding region SEQ ID NO:2108, protein SEQ ID NO:83) and placed into the pZB188/aadA shuttle vector, in a chimeric gene expressed from the native *Z. mobilis* glyceraldehyde-3-phosphate dehydrogernase (GAP) promoter (from ZW1, also called ZM4; SEQ ID NO:17).

The native distance between the Shine-Delgarno sequence for the GAP promoter and the initiation codon of the *E. coli* RPI-A coding region was preserved through primer design. Appropriate restriction enzyme recognition sites were added for cloning purposes. The PCR Primer-5 (SEQ ID NO:5) includes NcoI and SacI recognition sites added to the 5'-end of the GAP promoter sequence. Using Primer-6 (SEQ ID NO:6) in a reaction, paired with Primer-5, and ZW1 (ATCC #31821) genomic DNA as template, produced a 304 base pair DNA fragment containing the entire native *Z. mobilis* GAP promoter. This fragment also contained 15 base pairs of the 5'-end coding sequence for the *E. coli* RPI-A coding region by incorporation into the Primer-6 sequence. Using Primer-7 and Primer-8 (SEQ ID NOS:7 and 8), and genomic DNA isolated from *E. coli* K12, a 660 base pair fragment was amplified by PCR. The 5'-end of the fragment contained 15 base pairs of sequence corresponding to the 3'-end of the GAP promoter. Sequence for the restriction enzyme recognition site XhoI was added to the 3-end of the RPI-A coding region. The GAP promoter and RPI-A coding region fragments were isolated and used in a second PCR with Primer-5 and Primer-8. This reaction resulted in a single DNA fragment which linked the GAP promoter to the *E. coli* RPI-A coding region, preserving the native distance between Shine-Delgarno and initiation codon, also incorporating restriction enzyme sites for cloning into the pZB188/aadA shuttle vector (described in Example 2). Insertion into the shuttle vector followed digestion with the enzymes NcoI and XhoI. Transformation of the ligation product into competent *E. coli* SCS110 cells allowed isolation of an intact plasmid (named pZB-GI-RPI-ECA) which was then transformed into competent *Z. mobilis* ZW801-4 cells by the methods described in Example 2.

Figure 4:
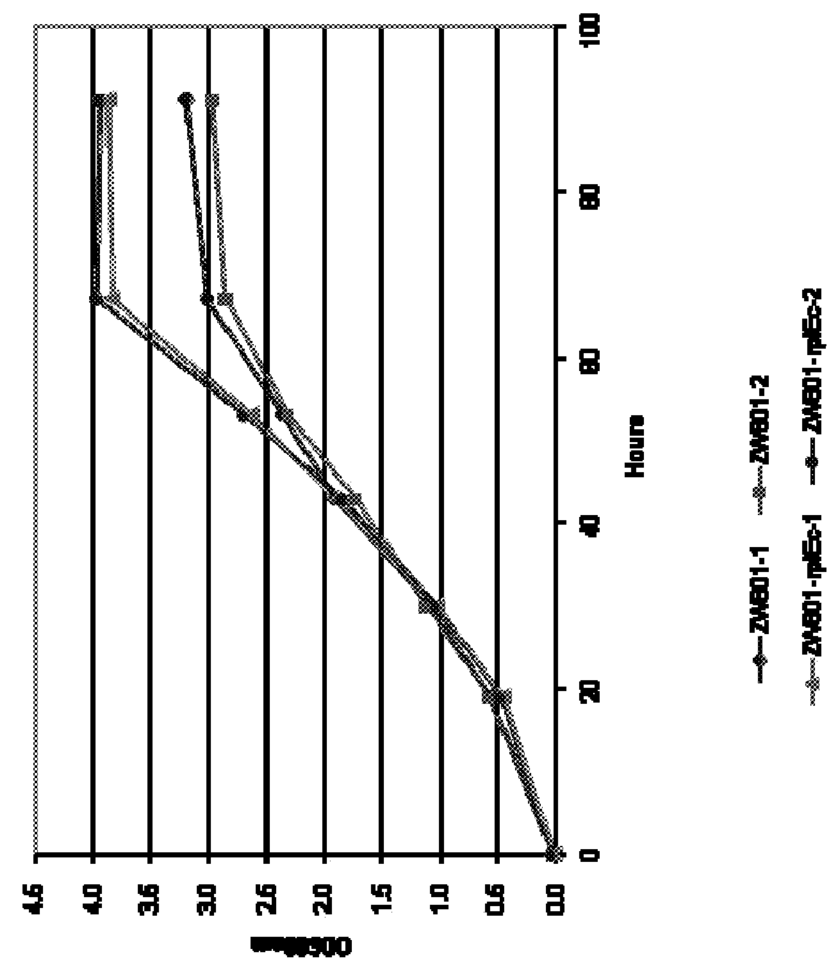
FIG. 4 shows a graph of growth of ZW801-4 control strains (ZW801-1 and ZW801-2) and ZW801-4 strains containing a plasmid containing a chimeric gene with a native *Z. mobilis* GAP promoter and an *E. coli* RPI-A coding region (ZW801-rpiEc-1 and ZW801-rpiEc-2).

Single colonies from MRM3G5-Spec250 plates, named strains ZW801-rpiEc-1 and ZW801-rpiEc-2, were grown in MRM3G10 liquid medium with spectinomycin (250 μg/ml) and then transferred to fresh MRM3×10, along with the parent ZW801-4 strain (ZW801-1 and ZW801-2) as a control. Optical density for the cultures was determined following 16 hours incubation at 30° C. Cells were transferred to fresh MRM3X10 medium, minimizing transfer of glucose into the xylose medium, and growth for the strains containing the chimeric gene expressing the *E. coli RPI-A* coding region was compared to the control (in duplicate) to determine whether an increase in cell mass and reduction in ribulose accumulation was possible through expression of this heterologous gene. Results in FIG. 4 demonstrate an increase in cell mass accumulation for the two independently isolated strains containing the chimeric gene expressing the heterologous RPI-A coding region as compared to controls. The results were similar to those demonstrated for the *Z. mobilis* RPI-A coding region, shown in FIG. 3A, with the transformed lines accumulating higher cell mass. HPLC analysis also demonstrated lower ribulose accumulation in the medium. The end-point analysis at 91 hours resulted in accumulation of 3.03 g/L ribulose for an average of the two control strains and only 2.12 g/L and 1.93 g/L ribulose for the strains ZW801-rpiEc-1 and ZW801-rpiEc-2, respectively. The results from this comparison are consistent with those demonstrated in Example 3, showing increased expression of RPI in a strain growing in medium containing xylose resulted in an increase in cell mass accumulation and reduced ribulose accumulation.

Example 5

Comparative: Fermentation Performance for Recombinant *Z. Mobilis* Strain ZW801-4 with Further Increased Xylose Isomerase Expression The *E. coli* xylA coding region was expressed from a GAP promoter on a multi-copy shuttle vector to increase activity for this enzyme. Expression was in the ZW801-4 strain which is a xylose-utilizing strain with high xylose isomerase activity due to a mutation in the promoter (Pgap) expressing the xylA coding region, as described in Example 1.

Construction of a pZB188/aadA (described in Example 2 above) vector containing the *E. coli* xylose isomerase coding region (coding region SEQ ID NO:20; protein SEQ ID NO:19) with its transcription directed by a native *Z. mobilis* glyceraldehyde-3-phosphate dehydrogenase (GAP) promoter (pZB188/aadA-GapXylA, also called pZB188/aadA-641GapXylA) was previously described in Example 5 of commonly owned and co-pending US Patent Application Publication US 2009-0246876 A1, which is herein incorporated by reference. The PgapXylA expression cassette (SEQ ID NO:18) has the GAP promoter (Pgap) from the ZW641 strain.

The pZB188/aadA and pZB188/aadA-641GapXylA plasmids were transformed into the strain ZW801-4 as described in Example 1 above. Strains were isolated from single colonies grown on a MMG-KAN500 plate (1% yeast extract, 15 mM $KH_2PO_4$, 4 mM $MgSO_4$, 50 g/L glucose, 500 μg/ml kanamycin) and transferred to MRM3X10 medium. The initial cell OD600 was adjusted to 0.08 for each strain and then cells were incubated at 30° C. with shaking at 150 RPM.

Figure 5:
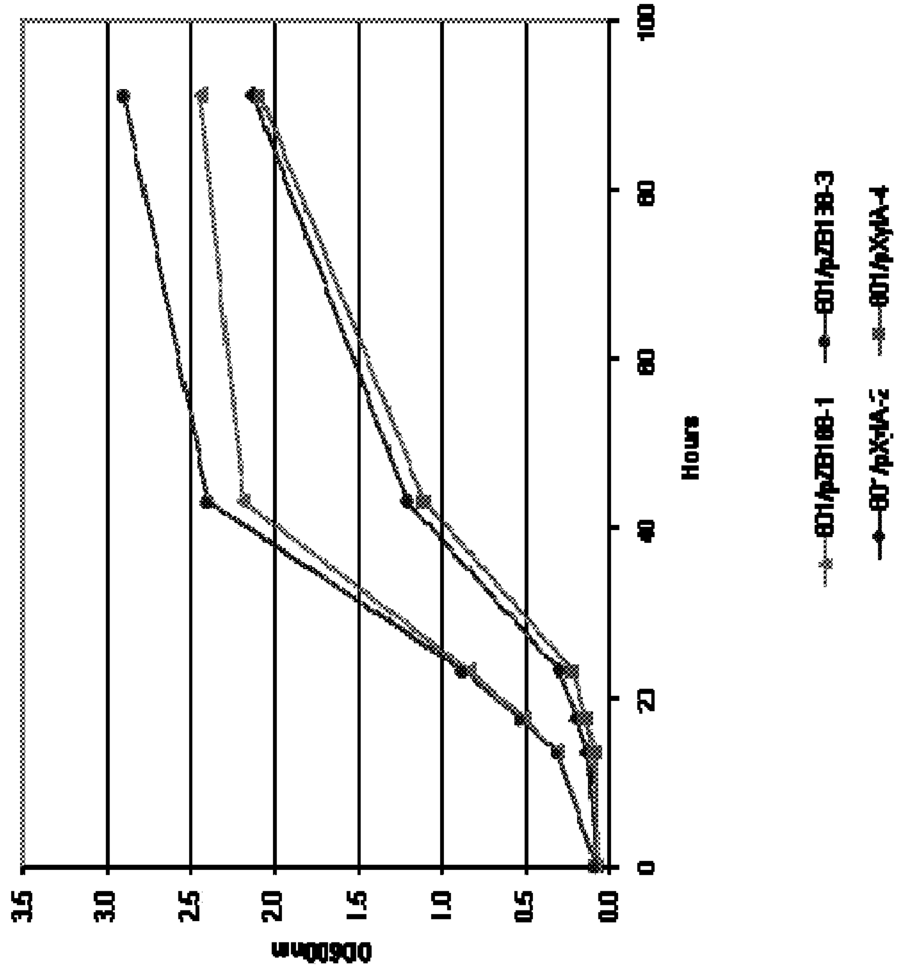
FIG. 5 shows a graph of growth of ZW801-4 control strains (801/pZB188-1 and 801/pZB188-3) and ZW801-4 strains containing a plasmid containing a chimeric gene with a *Z. mobilis* GAP promoter and an *E. coli* xylA coding region (801/pXylA-2 and 801/pXylA-4).

Growth rates of the strains in MRM3X10 medium are shown in FIG. 5. The results show that growth rates for the controls (801/pZB188-1 and 801/pZB188-3) were higher than for strains transformed with pZB188/aadA-641GapXylA (801/pXylA-2 and 801/pXylA-4). Final cell mass was also increased for the control strains growing in media containing xylose. HPLC analysis, in Table 6, also clearly demonstrated reduced use of xylose and lower ethanol production for strains containing pZB188/aadA-641GapXylA. Ribulose accumulation per gram of xylose used was also found to be increased in these strains compared to the control line.

Thus further increased expression of xylose isomerase in ZW801-4, which already has high expression of xylose isomerase as described above, is detrimental to fermentation performance.

TABLE 6

HPLC analysis of culture media following 91 hours incubation.

| Strain | Xylose | Ribulose | Ethanol |
|---|---|---|---|
| 801/pXylA-2 | 34.72 | 4.27 | 32.26 |
| 801/pXylA-4 | 39.05 | 3.93 | 29.67 |
| 801/pZB188-1 | 8.20 | 8.20 | 43.67 |
| 801/pZB188-3 | 5.57 | 6.95 | 45.17 |

Data is in g/L.

Example 6

Fermentation Performance for Strain ZW801-4 with Increased Expression of Xylose Isomerase and Ribulose-5-Phosphate Isomerase Effects of increasing expression of both xylose isomerase (XI) and ribulose-5-phosphate isomerase (RPI) in the high xylose isomerase expressing strain ZW801-4 were assessed.

The shuttle vectors pZB-GI-RPI, described in Example 1, and pZB188/aadA-641GapXylA, described in Example 5, were sequentially transformed into the *Z. mobilis* strain ZW801-4 described above. The strain containing the RPI-A vector, containing a spectinomycin marker, was isolated first by transformation and selection on MRM3G5-spec plates. Transformed cells were isolated as single colonies and then re-transformed with the xylA vector containing a kanamycin resistance marker. Strains isolated from MRM3G5-KAN plates were shown to be both spectinomycin and kanamycin tolerant, and are referred to as xylA/GI-rpiZ strains.

Individual colonies containing the two plasmids (xylA/G1-rpiZ1.1 and xylA/GI-rpiZ1.2) were grown overnight in MRM3G10 medium with both spectinimycin (250 μg/ml) and kanamycin (400 μg/ml). Control strains (ZW801-1 and ZW801-2) were grown in MRM3G10 medium with no antibiotic selection. Cells were then transferred to MRM3X10 medium and incubated for an additional 20 hours at 30° C. A final transfer to fresh MRM3X10 medium, at an initial OD600 of 0.1, was done to minimize transfer of glucose from the original culture into the test medium. The ZW801 control strain, in duplicate, and xylA/GI-rpiZ strains were incubated at 30° C. and monitored for cell growth and sugar consumption by HPLC analysis.

The results are shown in FIG. 6 (A-D). Growth of cells throughout the experiment is shown in FIG. 6A. Strains with increased XI and RPI expression grew at an increased rate and to a higher final cell mass, relative to the controls. The results are in contrast to those in Example 4 where a strain having only increased XI expression grew at a reduced rate in medium containing xylose. FIGS. 6B and 6C also show an improved fermentation performance with an increase in xylose use rate and final xylose amount consumed for strains carrying both xylA and RPI-A shuttle vectors, with increased xylose use reflected in an increase in final ethanol titer. FIG. 6D shows that ribulose levels were also found to be lower as compared to the controls.

Thus the combination of increased XI and RPI remedied the detrimental effect of increased XI alone (Example 5) and further increased xylose utilization and ethanol production in the high XI ZW801-4 strain.

Example 7

Increased Ribulose-5-Phosphate Isomerase Protein Levels in Recombinant *Z. mobilis* Strains Data in the above Examples demonstrated that increased expression of RPI-A protein in recombinant *Z. moblilis* resulted in increased fermentation performance. This example demonstrates an alternative method for increasing RPI in transformed cells.

The translation initiation codon for the *Z. mobilis* RPI-A coding region (SEQ ID NO:3895) was changed from the naturally occurring GTG codon to the more common ATG codon. In addition, the native *Z. mobilis* GAP promoter was linked to the coding sequence for RPI-A while preserving the distance between the Shine-Delgarno sequence and the initiation codon for this promoter. The GAP promoter (SEQ ID NO:17) was isolated from *Z. mobilis* ZW1 genomic DNA by PCR using Primer-5 (SEQ ID NO:5), which has NcoI and SacI restriction enzyme sites incorporated at the 3'-end and Primer-9 (SEQ ID NO:9), containing a 15 base pair overlap with the start of the RPI-A coding region. The 15 base pair overlap in Primer-9 also alters the native GTG start codon to an ATG.

The RPI-A coding region was isolated in a separate PCR using *Z. mobilis* ZW1 genomic DNA as template with Primer-10 (SEQ ID NO:10), also with the ATG start codon change and a 15 base pair overlap with the GAP promoter. Primer-11 (SEQ ID NO:11) was paired with Primer-10 in a reaction leading to isolation of the complete coding sequence for RPI-A. Primer-11 also contains an XhoI restriction enzyme recognition site for cloning into the pZB188 shuttle vector.

Following the two separate reactions, a third PCR was run with the two isolated DNA fragment products using Primer-5 and Primer-11. From this reaction a DNA fragment containing a GAP promoter linked to the RPI-A coding region with an ATG start codon was isolated and it was then digested with the enzymes NcoI and XhoI. The fragment was ligated into the pZB188/aadA shuttle vector, which was used to determine the effect of an altered start codon on steady state protein levels in transformed cells.

As a control, the same RPI-A coding region was isolated with its native GTG start codon by the same method, except that Primer-12 (SEQ ID NO:12) and Primer-13 (SEQ ID NO:13) were substituted in place of Primers 9 and 10. Following the first round of PCR, the two DNA fragments, one containing the GAP promoter with 15 base pair overlap to the native RPI-A coding region and the other containing the RPI-A coding region with the native start codon, were isolated and used in a third PCR. This reaction included Primer-5 and Primer-11, and produced a DNA fragment containing the GAP promoter linked to the RPI-A coding region with a native GTG start codon. This fragment was digested with the restriction enzymes NcoI and XhoI and ligated into the pZB188/aadA shuttle vector. The GAP-promoter native RPI-A expression vector was used as a control to compare to protein levels produced by cells containing the same promoter linked to the ATG altered version of the RPI-A coding region.

The shuttle vectors containing the native and ATG-altered genes were transformed into *E. coli* SCS110 competent cells. The plasmids isolated from *E. coli* were used to transform competent ZW801-4 cells and single colonies were selected by plating on MRM3G5-spec plates. Isolated single colonies named ZW801 GAP-rpi-1, ZW801 GAP-rpi-3 and ZW801 GAP-rpi-4 were grown overnight in MRM3G5 media with spectinomycin (250 μg/ml) and harvested for preparation of protein extracts. Extracts were made by transferring cells to fresh MRM3G10 medium and growing to an OD600 of 0.6 to 0.8. Concentration of total protein in the extracts was controlled by dilution of cells in a ratio of 1 OD600 to 44.38 μl of sample buffer. Sample buffer consisted of 650 μl water, 250 μl Nupage 4× loading buffer, and 100 μl 10× Nupage reducing buffer. The cells suspended in sample buffer, were heated to 80° C. for 10 minutes. Supernatants were collected following centrifugation at 13000 RPM for 10 minutes. Fifteen microliters of protein extract from the supernatants and Mark12 unstained standards (Invitrogen, Carlsbad, Calif.) were loaded on a 4-12% Nupage Bis-Tris acrylamide gel (Invitrogen, Carlsbad, Calif.), which was run using Nupage 1×MES SDS running buffer.

The SDS gel, stained with Simply Blue Safe Stain (Invitrogen, Carlsbad, Calif.) is shown in FIG. 7. From this figure it can be seen that the level of RPI-A protein from an extract of total protein was higher in strains containing the start codon altered RPI-A coding region (ZW801 GAP-rpi-1, ZW801 GAP-rpi-3 and ZW801 GAP-rpi-4 in lanes 2, 3, and 4, respectively) compared to the control lanes containing the native RPI-A coding region (lanes 5 and 6). The results are a clear demonstration that the level of *Z. mobilis* RPI-A protein level was increased in transformed lines by changing the start codon from the native GTG to ATG.

Example 8

Structural Analysis of Ribose-5-Phosphate Isomerase Enzymes

For analysis of RPI sequence structure, RPI proteins functionally characterized as ribose-5-phosphate isomerases were extracted from Brenda (BRENDA, AMENDA and FRENDA the enzyme information system: new content and tools in 2009. Chang A., Scheer M., Grote A., Schomburg I., Schomburg D. *Nucleic Acids Res.* 2009, Vol. 37, Database issue, D588-D592) and PubMed (US National Library of Medicine, National Institutes of Health) databases. These seed sequences included 15 sequences for RPI-A and 5 sequences for RPI-B. The RPI-A seed sequences are those from *E. coli* (SEQ ID NO:83), *Enterobacter cloacae* (SEQ ID NO:84), *Vibrio vulnificus* (SEQ ID NO:85), *Thermus thermophilus* (SEQ ID NO:86), *Chlamydomonas reinhardtii* (SEQ ID NO:87), *Spinacia oleracea* (SEQ ID NO:88), *Arabidopsis thaliana* (SEQ ID NO:89), *Arabidopsis thaliana* (SEQ ID NO:90), *Plasmodium falciparum* (SEQ ID NO:91), *Pyrococcus horikoshii* (SEQ ID NO:92), *Methanocaldococcus jannaschii* (SEQ ID NO:93), *Fibrobacter succinogenes* (SEQ ID NO:94), *Homo sapiens* (SEQ ID NO:95), *Caenorhabditis elegans* (SEQ ID NO:96), and *Saccharomyces cerevisiae* (SEQ ID NO:97). The RPI-B seed sequences are those from *Mycobacterium tuberculosis* (SEQ ID NO:1213), *Thermotoga maritime* (SEQ ID NO:1214), *Clostridium thermocellum* (SEQ ID NO:1215), *Escherichia coli* (SEQ ID NO:1216), and *Trypanosoma cruzi* (SEQ ID NO:1217). References with abstracts providing information on functional characterization of RPIs used as seed sequences is provided in Appendix file “rpi_exp_evid.doc”.

Each sequence (member) of the seed sequences was used to search the non-redundant Genbank database (National Center for Biotechnology Information, Bethesda, Md.) using BLAST with the E-value set at 0.001. Blast search results were combined separately for RPI-A and RPI-B, and redundancy at 100% ID and 100% length overlap was performed. This analysis resulted in 1232 RPI-A sequences and 1206 RPI-B sequences. These numbers were reduced to 1155 RPI-A sequences and 1112 RPI-B sequences by retaining sequences with a length in the range of 200-300 amino acids for RPI-A and 125-185 amino acids for RPI-B.

A multiple sequence alignment was made for each set of RPI-A and RPI-B seed sequences, which was then used to create a profile Hidden Markov Model (HMM) using the hmmsearch algorithm of the HMMER software package following the user guide which is available from HMMER (Janelia Farm Research Campus, Ashburn, Va.). The theory behind profile HMMs is described in R. Durbin, S. Eddy, A. Krogh, and G. Mitchison, *Biological sequence analysis: probabilistic models of proteins and nucleic acids*, Cambridge University Press, 1998; Krogh et al., 1994; J. Mol. Biol. 235:1501-1531). As stated in the user guide, Profile HMMs are statistical models of multiple sequence alignments. They capture position-specific information about how conserved each column of the alignment is, and which amino acid residues are most likely to occur at each position. Thus HMMs have a formal probabilistic basis. Profile HMMs for a large number of protein families are publicly available in the PFAM database (Janelia Farm Research Campus, Ashburn, Va.), and the software is publicly available for creating profile HMMs.

The Profile HMMs were built as follows:

Step 1. Build a Sequence Alignment

The seed sequences (sequences with high confidence infunctional characterization) were aligned using Clustal W with default parameters.

Step 2. Build a Profile HMM

The hmmbuild program was run on each set of aligned sequences using default parameters. hmmbuild reads the multiple sequence alignment file, builds a new Profile HMM, and saves the Profile HMM to file. Using this program a profile was generated from the multiple alignment for each set of seed sequences described above. The profile HMM for RPI-A is given in Table 4 and the profile HMM for RPI-B is given in Table 5.

The following information based on the HMMER software user guide gives some description of the way that the hmmbuild program prepares a Profile HMM. A Profile HMM is capable of modeling gapped alignments, e.g. including insertions and deletions, which lets the software describe a complete conserved domain (rather than just a small ungapped motif). Insertions and deletions are modeled using insertion (I) states and deletion (D) states. All columns that contain more than a certain fraction x of gap characters will be assigned as an insert column. By default, x is set to 0.5. Each match state has an I and a D state associated with it. HMMER calls a group of three states (M/D/I) at the same consensus position in the alignment a “node”. These states are interconnected with arrows called state transition probabilities. M and I states are emitters, while D states are silent. The transitions are arranged so that at each node, either the M state is used (and a residue is aligned and scored) or the D state is used (and no residue is aligned, resulting in a deletion-gap character, ‘–’). Insertions occur between nodes, and I states have a self-transition, allowing one or more inserted residues to occur between consensus columns.

The scores of residues in a match state (i.e. match state emission scores), or in an insert state (i.e. insert state emission scores) are proportional to Log_2 (p_x)/(null_x). Where p_x is the probability of an amino acid residue, at a particular position in the alignment, according to the Profile HMM and null_x is the probability according to the Null model. The Null model is a simple one state probabilistic model with pre-calculated set of emission probabilities for each of the 20 amino acids derived from the distribution of amino acids in the SWISSPROT release 24.

State transition scores are also calculated as log odds parameters and are propotional to Log_2 (t_x). Where t_x is the probability of transiting to an emitter or non-emitter state.

Step 3. Check the Profile HMM

The Profile HMMs were searched against the corresponding set of RPI-A or RPI-B homologues retrieved by BLAST search as noted above. An E value of 0.1 was used as a cut-off, with the Z parameter set to 1 billion. All RPI-A and RPI-B sequence homologues, except for one, were identified by the profile HMM searches. The non-matching sequence was removed. The RPI-A Profile HMM is given in Table 4, the RPI-B Profile Hmm is in Table 5.

Refining RPI-A and RPI-B Sequence Sets

Further refining of RPI-A and RPI-B sequence sets was as follows. Multiple sequence alignments were performed to remove sequences with internal, N-terminal or C-terminal truncations. This resulted in 1145 sequences for RPI-A and no change for RPI-B (1112 sequences).

Sequences were evaluated with respect to active site residues that had been identified for RPI-A and RPI-B (Roos et al. (2004) J. Mol. Biol. 335:799-809; Graile et al. (2005) Biochimie 87:763-769). These active site residues are:

For RPI-A: aspartic acid and glutamic acid at positions 107 and 128, respectively, in the *S. cerevisiae* sequence (D107 and E128; SEQ ID NO:97). Positions 107 and 128 of the *S. cerevisiae* protein correspond to positions 91 and 114, respectively, in the HMM profile.

For RPI-B: cysteine and threonine at positions 66 and 68, respectively, in the *E. coli* sequence (C66 and T68; SEQ ID NO:1216). Positions 66 and 68 of the *E. coli* protein correspond to positions 69 and 71, respectively, in the HMM profile.

OR: serine and glutamic acid at positions 68 and 72, respectively, in the *M. tuberculosis* sequence (S68 and E72; SEQ ID NO:1213). Positions 68 and 72 of the *M. tuberculosis* protein correspond to positions 71 and 75, respectively, in the HMM profile.

Proteins lacking the appropriate catalytic site residues were removed from the sets of RPI-A or RPI-B homologues. The final set of RPI-A proteins was 1130 proteins.

It was found that although the RpiB Profile HMM was generated from an alignment of RPI-B sequences derived from experimentally verified enzymes, the Profile HMM identifies a general class of sugar isomerases known as the RpiB/LacA/LacB family that contains, in addition to ribose-6-phosphate isomerase, the two subunits LacA and LacB of galactose-6-phosphate isomerase. The two subunits are easily identifiable: They are contiguously positioned in the genome, one subunit lacks the two catalytic residues, and the other brings complementary active site residues as well as the two catalytic residues.

The LacA subunit was removed from the RPI-B set of proteins by its lack of the catalytic residues. LacB proteins were distinguished from RPI-B proteins based on having leucine instead of asparagine at position 100 in the *E. coli* and *M. tuberculosis* proteins (SEQ ID NOs:1216 and 1213). RPI-B proteins may also have glycine, aspartic acid, serine, or glutamic acid at the position corresponding to 100, which corresponds to position 104. In the Profile HMM. Proteins having leucine at this position were removed from the RPI-B protein set, leaving 895 sequences.

Through this structural analysis, proteins matching RPI-A function have been identified as SEQ ID NOs:83 through 1212. Coding sequences for RPI-A proteins are SEQ ID NOs:2108 through 3237.

Through this structural analysis, proteins matching RPI-B function have been identified as SEQ ID NOs: 1213 through 2107. Coding sequences for RPI-B proteins are SEQ ID NOs: 3238 through 4132.

TABLE 3

HMMER2.0 [2.3.2][1]
NAME brenda_xylA3_seqs-con[2]
LENG 455[3]
ALPH Amino[4]
MAP yes[5]
COM hmmbuild brenda-xyla3.hmm brenda_xylA3_seqs-con.aln[6]
COM hmmcalibrate brenda-xyla3.hmm[7]
NSEQ 32[8]
DATE Wed Mar 12 21:55:22 2008[9]
XT −8455 −4 −1000 −1000 −8455 −4 −8455 −4
NULT −4 −8455[10]
NULE 595 −1558 85 338 −294 453 −1158 197 249 902 −1085 −142 −21 −313 45 531 201 384 −1998 −644[11]
EVD −379.726868 0.105452[12]

| HMM | A m->m | C m->i | D m->d | E i->m | F i->i | G d->m | H d->d | I b->m | K m->e | L | M | N | P | Q | R | S | T | V | W | Y | |
|---|---|---|---|---|---|---|---|---|---|---|---|---|---|---|---|---|---|---|---|---|---|
| | −152 | * | −3322 | | | | | | | | | | | | | | | | | | |
| 1(W) | −204 | 887 | 46 | 246 | −204 | −619 | 891 | −475 | 338 | −941 | 659 | 291 | −334 | 598 | 147 | −143 | 7 | −471 | 1260 | 199 | 51 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −383 | −8312 | −2119 | −894 | −1115 | −701 | −1378 | −152 | * | | | | | | | | | | | | |
| 2(I) | −652 | −1642 | −4507 | −4008 | 395 | −3998 | −3165 | 3120 | −3750 | 38 | −736 | −3643 | −3893 | −3438 | −3659 | −3185 | −1974 | 1769 | −2848 | −2496 | 52 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −9 | −7937 | −8980 | −894 | −1115 | −1952 | −431 | * | * | | | | | | | | | | | | |
| 3(D) | −60 | −2403 | 1750 | 355 | −2717 | 573 | −526 | −2474 | −145 | −2417 | −1502 | 888 | 1044 | 650 | −666 | 634 | −860 | −2023 | −2588 | −1891 | 53 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −9 | −7937 | −8980 | −894 | −1115 | −1952 | −431 | * | * | | | | | | | | | | | | |
| 4(K) | −1273 | −2543 | −1243 | −600 | −2936 | −2186 | −668 | −2589 | 2995 | −2503 | 541 | −838 | −82 | 803 | 733 | −1166 | −210 | −2211 | −2612 | −2088 | 54 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −9 | −7937 | −8980 | −894 | −1115 | −1952 | −431 | * | * | | | | | | | | | | | | |
| 5(I) | −2454 | −1957 | −5121 | −4804 | −2568 | −4911 | −4887 | 3182 | −4747 | −1338 | −1282 | −4599 | −4682 | −4674 | −4889 | −4283 | −2449 | 2522 | −4274 | −3775 | 55 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −9 | −7937 | −8980 | −894 | −1115 | −1952 | −431 | * | * | | | | | | | | | | | | |
| 6(Q) | −232 | −2237 | −616 | 690 | −2557 | −420 | −400 | −2306 | 1437 | −2253 | −1327 | 1063 | −363 | 1500 | 815 | −649 | 560 | −754 | −2421 | −1740 | 56 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −9 | −7937 | −8980 | −894 | −1115 | −1952 | −431 | * | * | | | | | | | | | | | | |
| 7(Y) | −4607 | −3566 | −5021 | −5359 | 2754 | −4894 | −1132 | −3491 | −4922 | −2814 | −2904 | −3541 | −4763 | −3674 | −4302 | −4158 | −4468 | −3655 | −380 | 4341 | 57 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −9 | −7937 | −8980 | −894 | −1115 | −1952 | −431 | * | * | | | | | | | | | | | | |
| 8(E) | −1557 | −2509 | −804 | 3252 | −3197 | −2167 | −1540 | −2531 | −1429 | −2964 | −2264 | −1142 | −2608 | −1221 | −1910 | −404 | −1676 | 930 | −3370 | −2737 | 58 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −9 | −7937 | −8980 | −894 | −1115 | −1952 | −431 | * | * | | | | | | | | | | | | |
| 9(G) | −4079 | −3917 | −4766 | −5131 | −5608 | 3825 | −4746 | −6295 | −5445 | −6007 | −5654 | −4803 | −4532 | −5224 | −5099 | −4361 | −4464 | −5518 | −4690 | −5554 | 59 |
| — | −149 | −500 | 233 | 44 | −381 | 398 | 108 | −625 | 210 | −466 | −721 | 275 | 394 | 45 | 97 | 359 | 117 | −369 | −295 | −250 | |
| — | −284 | −2499 | −8980 | −602 | −1552 | −1952 | −431 | * | * | | | | | | | | | | | | |
| 10(K) | −211 | −2265 | −699 | −143 | −2591 | −1802 | −444 | −2325 | 2070 | −2275 | −1362 | −444 | 1490 | 1183 | 432 | 193 | 169 | −1892 | −2442 | −1783 | 62 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −9 | −7937 | −8980 | −894 | −1115 | −1952 | −431 | * | * | | | | | | | | | | | | |
| 11(K) | −238 | −2256 | 1519 | 758 | −2576 | −602 | −412 | −2328 | 1550 | −2272 | −1346 | 498 | −1845 | 1040 | −505 | 399 | 267 | −1878 | −2440 | −1756 | 63 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −9 | −7937 | −8980 | −894 | −1115 | −1952 | −431 | * | * | | | | | | | | | | | | |

TABLE 3-continued

| | | | | | | | | | | | | | | | | | | | | | |
|---|---|---|---|---|---|---|---|---|---|---|---|---|---|---|---|---|---|---|---|---|---|
| 12(S) | −24 | −1368 | −1330 | −776 | −1457 | −2006 | −777 | −219 | 3 | −20 | −569 | −944 | −366 | −548 | −1012 | 2341 | 203 | −865 | −1771 | −1305 | 64 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −9 | −7937 | −8980 | −894 | −1115 | −1952 | −431 | * | * | | | | | | | | | | | | |
| 13(K) | −815 | −2291 | 332 | 381 | −2610 | −1764 | −439 | −2362 | 2248 | −2306 | −1383 | 929 | −1870 | 1259 | −537 | 203 | 744 | −1912 | −2474 | −1788 | 65 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −9 | −7937 | −8980 | −894 | −1115 | −1952 | −431 | * | * | | | | | | | | | | | | |
| 14(N) | −112 | −2600 | −523 | 381 | −2952 | −1931 | −753 | −2702 | 541 | −2657 | −1773 | 3112 | −2133 | −322 | −907 | 983 | −1121 | −2258 | −2837 | −2142 | 66 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −9 | −7937 | −8980 | −894 | −1115 | −1952 | −431 | * | * | | | | | | | | | | | | |
| 15(P) | −67 | −1766 | −1443 | −999 | −2363 | 1282 | −1134 | −1992 | 272 | −2170 | 1037 | −1129 | 2920 | −813 | −1183 | −1074 | −1062 | −1654 | −2530 | −2036 | 67 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −9 | −7937 | −8980 | −894 | −1115 | −1952 | −431 | * | * | | | | | | | | | | | | |
| 16(L) | −1558 | −1364 | −253 | −3026 | 1709 | −3054 | −1523 | −618 | −2677 | 2198 | 1130 | −2548 | −3046 | −2242 | −2517 | −2147 | −1490 | −703 | −1178 | 1973 | 68 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −9 | −7937 | −8980 | −894 | −1115 | −1508 | −625 | * | * | | | | | | | | | | | | |
| 17(A) | 2539 | −1340 | −2407 | −1923 | −114 | 254 | −1611 | −1400 | −1746 | −1704 | 967 | −1746 | −2462 | −1570 | −1957 | 1232 | −1093 | −1168 | −2213 | −1825 | 69 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8005 | −9047 | −894 | −1115 | −1811 | −484 | * | * | | | | | | | | | | | | |
| 18(F) | −3970 | −3283 | −4844 | −4992 | 4163 | −4617 | −1220 | −3051 | −4579 | −2594 | −2558 | −3472 | −4567 | −3555 | −4097 | −3851 | −332 | −3156 | −493 | 2114 | 70 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8005 | −9047 | −894 | −1115 | −1811 | −484 | * | * | | | | | | | | | | | | |
| 19(K) | −1512 | −2771 | −1507 | −818 | −3232 | −2385 | 2267 | −2858 | 2388 | −2715 | −1873 | 46 | −2431 | 989 | 2056 | −1394 | −1391 | −589 | −2767 | −2293 | 71 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8005 | −9047 | −894 | −1115 | −1811 | −484 | * | * | | | | | | | | | | | | |
| 20(Y) | −3420 | −2864 | −4689 | −4633 | 1930 | −4361 | 3299 | −2576 | −4223 | −668 | −2142 | −3313 | −4295 | −3326 | −3804 | −3534 | −3326 | −132 | 2330 | 3572 | 72 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8005 | −9047 | −894 | −1115 | −1811 | −484 | * | * | | | | | | | | | | | | |
| 21(Y) | −3783 | −3746 | −2646 | −265 | −826 | −3845 | −1884 | −3929 | −3309 | −3512 | −3401 | −2873 | −4182 | −3050 | −3402 | −3623 | −3828 | −3890 | −1488 | 4716 | 73 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8005 | −9047 | −894 | −1115 | −1811 | −484 | * | * | | | | | | | | | | | | |
| 22(N) | −2403 | −4115 | 2160 | −610 | −4589 | −2333 | −1803 | −4558 | −2130 | −4439 | −3800 | 3631 | −2908 | −1490 | −3023 | −352 | −2529 | −3961 | −4620 | −3589 | 74 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8005 | −9047 | −894 | −1115 | −1811 | −484 | * | * | | | | | | | | | | | | |
| 23(P) | 1749 | −1901 | −2474 | −2677 | −4084 | −2051 | −2900 | −3873 | −3079 | −4087 | −3221 | 194 | 3510 | −2758 | −3227 | −1440 | −1653 | −2866 | −4265 | −3960 | 75 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8005 | −9047 | −894 | −1115 | −1811 | −484 | * | * | | | | | | | | | | | | |
| 24(E) | −1269 | −2810 | 2039 | 2488 | −3105 | −1980 | −824 | −2879 | 132 | −2814 | −1924 | 557 | −2199 | 462 | −1082 | −1105 | −1230 | −604 | −2987 | −2252 | 76 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8005 | −9047 | −894 | −1115 | −1811 | −484 | * | * | | | | | | | | | | | | |
| 25(E) | −1569 | −3030 | −675 | 2974 | −3390 | −2199 | −979 | −3118 | 1545 | −3013 | −2167 | −824 | −2424 | 431 | −850 | −255 | −1514 | −2686 | −3134 | −2484 | 77 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8005 | −9047 | −894 | −1115 | −1811 | −484 | * | * | | | | | | | | | | | | |
| 26(V) | −940 | −874 | −2689 | 438 | 215 | −2419 | −1259 | 1264 | 196 | 312 | −72 | −1852 | −2473 | −1538 | −1814 | −1476 | 712 | 1953 | −1336 | −976 | 78 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8005 | −9047 | −894 | −1115 | −1811 | −484 | * | * | | | | | | | | | | | | |
| 27(I) | −2373 | −1909 | −4992 | −4608 | −2445 | −4701 | −4324 | 2910 | −4485 | −353 | −1224 | −4353 | −4509 | −4336 | −4547 | −3996 | −278 | 2559 | −3880 | −3432 | 79 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8005 | −9047 | −894 | −1115 | −1147 | −867 | * | * | | | | | | | | | | | | |
| 28(M) | 297 | −2163 | 527 | 293 | −2408 | 1145 | −557 | −2107 | 444 | 404 | 2320 | 222 | −1978 | −127 | −668 | −804 | −824 | −1744 | −2394 | −1759 | 80 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8107 | −9149 | −894 | −1115 | −623 | −1512 | * | * | | | | | | | | | | | | |

TABLE 3-continued

| | | | | | | | | | | | | | | | | | | | | | |
|---|---|---|---|---|---|---|---|---|---|---|---|---|---|---|---|---|---|---|---|---|---|
| 29(G) | −858 | −2502 | 613 | −529 | −2936 | 2600 | −948 | −2664 | −620 | −2675 | 970 | 838 | −430 | −525 | −1133 | 25 | −1200 | −2235 | −2897 | −2236 | 81 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8252 | −9294 | −894 | −1115 | −533 | −1695 | * | * | | | | | | | | | | | | |
| 30(K) | −1648 | −2125 | −2186 | −1533 | −1645 | −2748 | 734 | −1787 | 3106 | −865 | −1291 | −1622 | −2796 | −1038 | −912 | −1781 | −1555 | 269 | −1998 | 1612 | 82 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 31(T) | −1046 | −2501 | −897 | 404 | −2830 | −2011 | −653 | −2571 | 1787 | −2511 | −1591 | −648 | 227 | 1574 | 636 | −249 | 1801 | −2128 | −2671 | −2004 | 83 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 32(M) | −551 | −1875 | −3895 | −3452 | −1627 | −3127 | −2589 | −1019 | −3062 | 172 | 4465 | −3001 | 1725 | −2776 | −2984 | −2338 | −1912 | −1168 | −2513 | −2250 | 84 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 33(K) | 127 | −2511 | −888 | 1379 | −2865 | −2030 | −726 | −2605 | 2447 | −2560 | −1648 | −691 | −2148 | −275 | −785 | 270 | 1004 | −2163 | −2733 | −2065 | 85 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 34(D) | −2246 | −3964 | 2730 | 2201 | −4210 | −2482 | −1633 | −4052 | −1600 | −3950 | −3164 | −1082 | 1471 | −1258 | 488 | −1984 | −2261 | −3563 | −4127 | −3260 | 86 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 35(W) | −307 | −2255 | −1047 | 1375 | −2417 | −2110 | 3282 | −2137 | −380 | −1097 | −1379 | −803 | −2206 | 929 | −826 | −1054 | −1045 | −1820 | 3681 | −1859 | 87 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 36(L) | −2283 | −2311 | 1522 | −2528 | 661 | −3412 | 1226 | −1601 | −2637 | 2573 | −1135 | −2460 | −3499 | −2296 | −2785 | −2587 | −2228 | −1696 | −1466 | −539 | 88 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 37(R) | −3325 | −3893 | −4311 | −2623 | −4835 | −3766 | 1845 | −4080 | 1753 | −3674 | −3032 | −2431 | −3666 | −1120 | 3594 | −3191 | −2938 | −3882 | −3468 | −3430 | 89 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 38(F) | −5308 | −4420 | −5610 | −5948 | 4547 | −4921 | −3048 | −4656 | −5852 | −3992 | −4112 | −4995 | −5217 | −5110 | −5315 | −5363 | −5399 | −4866 | −2341 | −1279 | 90 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 39(S) | 2011 | −1975 | −4184 | −4245 | −4465 | −522 | −3670 | −4249 | −4052 | −4495 | −3559 | −2916 | −3035 | −3647 | −3928 | 2570 | 1512 | −3083 | −4681 | −4554 | 91 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 40(V) | −389 | −1555 | −4211 | −3620 | 2221 | −3520 | −2467 | 827 | −3266 | −146 | 1500 | −3166 | −3495 | −2880 | −3090 | −2639 | −1760 | 2647 | −2235 | −1917 | 92 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 41(A) | 2968 | 1546 | −4577 | −4780 | −4439 | 1767 | −3862 | −4189 | −4447 | −4480 | −3561 | −3040 | −3058 | −3946 | −4144 | −1616 | −19 | −3053 | −4696 | −4614 | 93 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 42(Y) | −4757 | −3801 | −5352 | −5629 | 2454 | −5193 | −1481 | −3601 | −5191 | 1280 | −3022 | −3865 | −5051 | −3974 | −4590 | −4428 | −4620 | −3780 | 3031 | 3651 | 94 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 43(W) | −6178 | −4896 | −5848 | −6204 | −4109 | −4952 | −4743 | −6650 | −6203 | −5992 | −6031 | −5971 | −5371 | −6028 | −5699 | −6531 | −6329 | −6559 | 6291 | −3733 | 95 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 44(H) | −2390 | −2940 | −3006 | −3167 | −3361 | −3029 | 4890 | −4377 | −2892 | −4385 | −3795 | −2928 | −3660 | −3087 | −2954 | −2556 | 2015 | −3712 | −3688 | −2968 | 96 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −383 | −8312 | −2119 | −894 | −1115 | −701 | −1378 | * | * | | | | | | | | | | | | |
| 45(T) | −1111 | −1722 | −3459 | −3693 | −4071 | −1979 | −3313 | −3836 | −3645 | −4141 | −3273 | −2568 | −2762 | −3316 | −3519 | 182 | 3789 | −2767 | −4303 | −4118 | 97 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −9 | −7937 | −8980 | −894 | −1115 | −254 | −2629 | * | * | | | | | | | | | | | | |

TABLE 3-continued

| | | | | | | | | | | | | | | | | | | | | | |
|---|---|---|---|---|---|---|---|---|---|---|---|---|---|---|---|---|---|---|---|---|---|
| 46(F) | −2728 | −2359 | −5136 | −4558 | 3354 | −4572 | −3468 | 910 | −4252 | 475 | 1893 | −4231 | −4294 | −3617 | −3993 | −3745 | −2649 | 1605 | −2824 | −2691 | 98 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 47(C) | −1098 | 2971 | 1338 | −866 | −2368 | 1340 | −1058 | −2007 | −774 | −2171 | −1369 | −1075 | −2324 | −705 | 113 | −1140 | 1757 | −600 | −2527 | −1988 | 99 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 48(W) | 1080 | −2296 | −913 | 535 | −2548 | 415 | −675 | −2251 | −288 | −2283 | 573 | 864 | −2098 | 1523 | −780 | −923 | −946 | −1882 | 3639 | −1888 | 100 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 49(D) | −994 | −2466 | 1756 | 978 | −2785 | −1962 | −625 | −2536 | −208 | −2481 | −1556 | 1471 | −2058 | 1356 | 818 | −349 | 553 | −426 | −2650 | −1967 | 101 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 50(W) | −204 | 887 | 46 | 246 | −204 | −619 | 891 | −475 | 338 | −941 | 659 | 291 | −334 | 598 | 147 | −143 | 7 | −471 | 1260 | 199 | 102 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 51(G) | −321 | −2099 | −3782 | −3944 | −3733 | 3298 | −3507 | −3250 | −3871 | 860 | −2925 | −2956 | −3185 | −3562 | −3763 | −1823 | −1971 | −2699 | −4191 | −3938 | 103 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 52(R) | 877 | −2295 | −923 | −374 | −2567 | −29 | −672 | −2273 | 201 | −2299 | −1418 | 171 | −2092 | −237 | 1473 | 1037 | 601 | 603 | −2534 | −1895 | 104 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 53(D) | −4886 | −4905 | 4186 | −3339 | −5949 | −4221 | −4195 | −6666 | −4787 | −6283 | −6022 | −3676 | −4750 | −4186 | −5191 | −4762 | −5055 | −6188 | −5117 | −5507 | 105 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 54(P) | −358 | −1704 | −2202 | −1724 | −1995 | −2408 | −1572 | −1504 | −1467 | −1768 | 1554 | −1730 | 3367 | 1187 | −1721 | −1521 | −1336 | −433 | −2377 | −1966 | 106 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 55(F) | −5308 | −4420 | −5610 | −5948 | 4547 | −4921 | −3048 | −4656 | −5852 | −3992 | −4112 | −4995 | −5217 | −5110 | −5315 | −5363 | −5399 | −4866 | −2341 | −1279 | 107 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 56(G) | −4740 | −4445 | −5364 | −5738 | −6131 | 3840 | −5265 | −6903 | −6030 | −6539 | −6235 | −5426 | −5034 | −5814 | −5624 | −5041 | −5115 | −6153 | −5123 | −6096 | 108 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 57(D) | 674 | −2424 | 2070 | 271 | −2717 | 297 | −669 | −2448 | 257 | −2431 | −1527 | −639 | −352 | −221 | −775 | −916 | −171 | 1037 | −2630 | −1963 | 109 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 58(G) | 2216 | −2048 | −3999 | −4272 | −4632 | 2814 | −3817 | −4443 | −4322 | −4692 | −3754 | −2971 | 778 | −3836 | −4128 | −1679 | −1899 | −3208 | −4829 | −4747 | 110 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 59(T) | −552 | −1875 | −3402 | −3173 | −3341 | −2281 | −2846 | −2926 | −3030 | −3256 | −2480 | −431 | −2933 | −2784 | −3135 | 445 | 3459 | 549 | −3668 | −3358 | 111 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 60(M) | 1157 | −1590 | −1704 | −1125 | 650 | −2335 | −1036 | −1217 | 1096 | −1475 | 2399 | −1271 | −2407 | −836 | 1972 | −1316 | −1065 | −1061 | −1945 | 272 | 112 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 61(Q) | 506 | −2444 | 274 | 1073 | −701 | −1222 | −615 | −365 | 270 | −2458 | −1534 | 700 | −532 | 2051 | −444 | −279 | 33 | −667 | −2629 | −1949 | 113 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 62(R) | 716 | −1736 | −2244 | −1683 | 752 | −2703 | −1193 | −1344 | −1412 | −1580 | −929 | −63 | −2766 | −1328 | 3068 | −1710 | −1403 | −1220 | 1669 | 685 | 114 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |

TABLE 3-continued

| | | | | | | | | | | | | | | | | | | | | | |
|---|---|---|---|---|---|---|---|---|---|---|---|---|---|---|---|---|---|---|---|---|---|
| 63(P) | −625 | −2530 | 60 | −1072 | −2925 | −2398 | −1624 | −2563 | −1584 | 1086 | −2026 | 184 | 3237 | −1340 | −2075 | −1705 | −1751 | −2272 | −3163 | −2593 | 115 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −90 | −8312 | −4120 | −894 | −1115 | −701 | −1378 | * | * | | | | | | | | | | | | |
| 64(W) | −4762 | −4593 | 2301 | −3636 | −3451 | −4258 | −3708 | −5821 | −4679 | −5395 | −5229 | −3844 | −4736 | −4222 | −4864 | −4710 | −4913 | −5577 | 5797 | −3009 | 116 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −130 | −8229 | −3598 | −894 | −1115 | −1121 | −889 | * | * | | | | | | | | | | | | |
| 65(D) | −1309 | −2840 | 2011 | 494 | −3135 | −2037 | −873 | −2906 | −572 | −2846 | −1955 | 2010 | 1717 | 1170 | −1125 | −1150 | −1269 | −671 | −3021 | −2290 | 117 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −2311 | −8107 | −331 | −894 | −1115 | −628 | −1503 | * | * | | | | | | | | | | | | |
| 66(Y) | −635 | −882 | −1209 | −779 | 422 | −1778 | −110 | −454 | −556 | 590 | −63 | 1215 | −1869 | −452 | −785 | −844 | −583 | −360 | −175 | 2802 | 118 |
| — | −149 | −500 | 234 | 43 | −381 | 399 | 106 | −626 | 210 | −466 | −721 | 275 | 394 | 46 | 96 | 359 | 117 | −369 | −294 | −249 | |
| — | −1029 | −988 | −7468 | −137 | −3461 | −571 | −1614 | * | * | | | | | | | | | | | | |
| 67(H) | −9 | −2243 | 374 | 1170 | −2564 | 95 | 1478 | −2314 | 1276 | −2259 | −1332 | −378 | −1836 | 1253 | 987 | −8 | −709 | −1865 | −2426 | −1743 | 120 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −9 | −7937 | −8980 | −894 | −1115 | −1952 | −431 | * | * | | | | | | | | | | | | |
| 68(Y) | −804 | −1603 | −77 | −470 | −287 | 1328 | −615 | −1330 | 378 | −176 | −755 | −707 | −70 | −291 | −797 | −226 | −744 | −1108 | −1927 | 2425 | 121 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −9 | −7937 | −8980 | −894 | −1115 | −1952 | −431 | * | * | | | | | | | | | | | | |
| 69(T) | −167 | −2183 | 188 | −187 | −2570 | 677 | −524 | −2303 | 362 | −2287 | −1382 | −483 | −141 | −80 | −634 | 985 | 2088 | −1868 | −2484 | −1822 | 122 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −9 | −7937 | −8980 | −894 | −1115 | −1952 | −431 | * | * | | | | | | | | | | | | |
| 70(D) | −1090 | −2605 | 2512 | 741 | −2908 | 391 | 837 | −2674 | −342 | −2615 | −1713 | 665 | −2065 | −234 | −883 | 9 | 769 | −2220 | −2788 | −2070 | 123 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −262 | −7937 | −2624 | −894 | −1115 | −1952 | −431 | * | * | | | | | | | | | | | | |
| 71(P) | 1251 | −2101 | −546 | 596 | −2491 | −1704 | −497 | −2212 | 497 | −2217 | −1335 | −424 | 2156 | −66 | −607 | 788 | −767 | −1795 | −2431 | −1781 | 124 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7686 | −8728 | −894 | −1115 | −1200 | −825 | * | * | | | | | | | | | | | | |
| 72(M) | −1983 | −1721 | −4201 | −671 | −1027 | −3652 | −2508 | 473 | −3258 | 1831 | 3893 | −3253 | −3511 | −2756 | −3069 | −2772 | −1908 | 239 | −2109 | −1917 | 125 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −9 | −7937 | −8980 | −894 | −1115 | −1952 | −431 | * | * | | | | | | | | | | | | |
| 73(D) | 325 | −3516 | 2804 | 2034 | −3761 | −2131 | −1242 | −3593 | −1187 | −3502 | −2691 | 664 | −2522 | 465 | −1858 | −1573 | −1824 | −3108 | −3684 | −2831 | 126 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −9 | −7937 | −8980 | −894 | −1115 | −1952 | −431 | * | * | | | | | | | | | | | | |
| 74(M) | −162 | 687 | −1246 | 48 | −1449 | −1992 | −713 | 457 | 968 | 807 | 1568 | −876 | −2071 | 590 | 824 | −952 | 177 | −864 | −1751 | −1277 | 127 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −9 | −7937 | −8980 | −894 | −1115 | −1952 | −431 | * | * | | | | | | | | | | | | |
| 75(A) | 3609 | −2502 | −4177 | −4484 | −4584 | −2730 | −3982 | −4412 | −4488 | −4693 | −4043 | −3432 | −3468 | −4163 | −4245 | −2287 | −2480 | −3528 | −4478 | −4636 | 128 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −9 | −7937 | −8980 | −894 | −1115 | −1952 | −431 | * | * | | | | | | | | | | | | |
| 76(K) | −1027 | −2025 | −1083 | 321 | −188 | −2040 | 1105 | −1850 | 2712 | 477 | −1152 | −762 | −2121 | −270 | −504 | −1005 | −952 | −1581 | −2205 | −1638 | 129 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −9 | −7937 | −8980 | −894 | −1115 | −1952 | −431 | * | * | | | | | | | | | | | | |
| 77(A) | 2085 | −2164 | −961 | −400 | −2453 | −1963 | −598 | −2122 | −76 | −2158 | 472 | 939 | −2059 | 608 | 1792 | −921 | −920 | −1780 | −2390 | −1815 | 130 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −9 | −7937 | −8980 | −894 | −1115 | −1952 | −431 | * | * | | | | | | | | | | | | |
| 78(R) | −3027 | −3580 | −3980 | −2342 | −4547 | −3455 | −1266 | −3796 | 2824 | −3394 | −2754 | −2150 | −3372 | −849 | 3133 | −2900 | −2653 | −3595 | −3184 | −3156 | 131 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −9 | −7937 | −8980 | −894 | −1115 | −1952 | −431 | * | * | | | | | | | | | | | | |
| 79(V) | 1224 | −1553 | −4145 | −3706 | −1862 | −3327 | −2889 | 214 | −3415 | −1131 | 2011 | −3214 | −3508 | −3137 | −3344 | −2552 | −1771 | 3003 | −2764 | −2407 | 132 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −9 | −7937 | −8980 | −894 | −1115 | −254 | −2629 | * | * | | | | | | | | | | | | |

TABLE 3-continued

| | | | | | | | | | | | | | | | | | | | | | |
|---|---|---|---|---|---|---|---|---|---|---|---|---|---|---|---|---|---|---|---|---|---|
| 80(D) | −493 | −3116 | 2767 | 1555 | −3391 | −2262 | −1166 | −3139 | 191 | −3116 | −2255 | −888 | −2518 | −751 | −1483 | −1454 | −1589 | 1219 | −3318 | −2582 | 133 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 81(A) | 2284 | −1391 | −2040 | 1144 | −1397 | −2450 | −1253 | −149 | −1343 | −1258 | −592 | −1560 | −2537 | −1201 | −1606 | −1469 | −1103 | 118 | −1822 | 1911 | 134 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 82(A) | 2251 | −1006 | −3057 | −2446 | 931 | −297 | 873 | 186 | −2124 | 136 | −207 | −2119 | −2664 | −1821 | −2064 | −199 | −1051 | 393 | −1458 | −1105 | 135 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 83(F) | −2224 | −2250 | −4424 | −4264 | 3927 | −1145 | −2398 | −1376 | −3976 | −1984 | −1709 | −3372 | −3765 | −3490 | −3760 | −2682 | −2389 | 1653 | −1938 | −991 | 136 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 84(E) | −2532 | −3829 | −1248 | 3330 | −4180 | −2869 | 2424 | −3974 | −839 | −3774 | −3045 | −1508 | −3153 | −1222 | 558 | −2322 | −2451 | −3596 | −3729 | −3191 | 137 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 85(F) | −1403 | −1396 | −2948 | −2272 | 3286 | −2799 | −1493 | 1022 | 1260 | −1060 | 686 | −2099 | −2836 | −1618 | 230 | −1871 | −1330 | −773 | −1748 | −1356 | 138 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 86(F) | −317 | 889 | −3643 | −3012 | 2565 | −2871 | −1711 | −515 | −2614 | 1586 | 2444 | −2508 | −2900 | −2216 | −2412 | −1959 | −1257 | −505 | −1529 | 755 | 139 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 87(E) | 1138 | −2517 | −22 | 2128 | −2834 | −1986 | 953 | −2586 | −260 | −2532 | −1609 | 47 | −2094 | 1725 | −772 | −522 | −30 | −2137 | −2701 | −2014 | 140 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 88(K) | −3061 | −4130 | −1699 | 1837 | −4807 | −3224 | −1891 | −4412 | 3434 | −4126 | −3469 | −1918 | −3509 | −1513 | −1024 | −2841 | −2941 | −4072 | −3990 | −3669 | 141 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 89(L) | −3259 | −2823 | −5615 | −5021 | −1437 | −5150 | −3961 | 745 | −4731 | 2913 | 1019 | −4827 | −4647 | −3875 | −4383 | −4368 | 365 | −1276 | −3007 | −3044 | 142 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 90(G) | −1754 | −3293 | 758 | −600 | −3610 | 2854 | 295 | −3395 | −1059 | −3333 | −2477 | 1368 | −2611 | −871 | −192 | −608 | −1738 | −2933 | −3514 | −2754 | 143 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 91(V) | 1814 | −1770 | −4355 | −3892 | −2144 | −3716 | −3087 | 1744 | −3628 | −1521 | −1158 | −748 | −3817 | −3368 | −3576 | −2912 | −2012 | 2602 | −2979 | −2593 | 144 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 92(P) | −1176 | −2665 | 795 | 1462 | −2975 | −2054 | 1351 | −2732 | 293 | −2676 | −1764 | 301 | 2104 | −333 | −927 | −1042 | −1122 | −2283 | −2848 | 1814 | 145 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 93(Y) | −3660 | −3259 | −4548 | −4414 | 1974 | 1637 | −1482 | −3075 | −3905 | −2811 | −2599 | −3440 | −4500 | −3380 | −86 | −3688 | −3603 | −3082 | −832 | 3949 | 146 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 94(F) | −1766 | −1543 | −3984 | −3431 | 2846 | −3263 | −1648 | 658 | −3029 | 322 | −605 | −2801 | −3277 | −2560 | −2795 | −2362 | −1702 | 919 | 1783 | 2653 | 147 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 95(C) | 367 | 5085 | −4219 | −4291 | −4096 | −2272 | −3593 | −3763 | −4037 | −4088 | −3236 | 350 | −3041 | −3643 | −3867 | −1621 | 1654 | −2856 | −4389 | −4220 | 148 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 96(F) | −4420 | −3702 | −5536 | −5637 | 4337 | −5230 | −2140 | −2246 | −5268 | −125 | −1647 | −4338 | −5053 | −4174 | −4736 | −4670 | −4342 | −2825 | −1358 | −250 | 149 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |

TABLE 3-continued

| | | | | | | | | | | | | | | | | | | | | | |
|---|---|---|---|---|---|---|---|---|---|---|---|---|---|---|---|---|---|---|---|---|---|
| 97(H) | −5506 | −4764 | −5029 | −5331 | −4362 | −4732 | +Z,29 | −6634 | −5266 | −6082 | −5977 | −5274 | −5186 | −5341 | −5054 | −5722 | −5705 | −6336 | −4332 | −3976 | 150 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 98(D) | −4886 | −4905 | 4186 | −3339 | −5949 | −4221 | −4195 | −6666 | −4787 | −6283 | −6022 | −3676 | −4750 | −4186 | −5191 | −4762 | −5055 | −6188 | −5117 | −5507 | 151 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 99(R) | −1078 | −2255 | 1071 | 345 | −2468 | −2070 | −762 | 246 | −400 | −2220 | −1378 | 214 | −2175 | −352 | 2115 | −1018 | −1019 | 1592 | −2508 | −1898 | 152 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 100(W) | −204 | 887 | 46 | 246 | −204 | −619 | 891 | −475 | 338 | −941 | 659 | 291 | −334 | 598 | 147 | −143 | 7 | −471 | 1260 | 199 | 153 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 101(D) | −4886 | −4905 | +Z,30 | −3339 | −5949 | −4221 | −4195 | −6666 | −4787 | −6283 | −6022 | −3676 | −4750 | −4186 | −5191 | −4762 | −5055 | −6188 | −5117 | −5507 | 154 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 102(I) | −3148 | −2630 | −5718 | −5282 | −1996 | −5478 | −4785 | 2752 | −5148 | 2210 | −760 | −5155 | −4982 | −4511 | −4983 | −4815 | −3092 | 885 | −3726 | −3666 | 155 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 103(A) | 2332 | 880 | −3499 | −2885 | 155 | −2753 | −1687 | 1413 | −2507 | −912 | −290 | −2404 | −2824 | −2151 | −2344 | 131 | −1170 | 922 | −1580 | −1235 | 156 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 104(P) | −672 | −3716 | 211 | −35 | −4479 | −2521 | −1993 | −4330 | −2167 | −4293 | −3563 | −1294 | 3795 | −1666 | −2911 | −671 | −2463 | −3744 | −4510 | −3639 | 157 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 105(E) | −1113 | −2563 | 755 | 2544 | 1516 | −2031 | −733 | −2609 | −341 | −2569 | −1661 | −668 | −2154 | 563 | 301 | −991 | −66 | −2175 | −2752 | −2069 | 158 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 106(G) | 299 | −2657 | 34 | −2104 | −4774 | 3464 | −2959 | −4642 | −3376 | −4771 | −3958 | −2126 | −3197 | −2757 | −3854 | −1993 | −2272 | −3598 | −4890 | −4406 | 159 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 107(D) | 940 | −2485 | 1893 | 127 | −2803 | −1971 | 844 | −2554 | 764 | −2500 | −1576 | 1057 | −2071 | −182 | −737 | 809 | 137 | −2106 | −2669 | −1984 | 160 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 108(T) | −1565 | −2482 | 739 | −1528 | −3930 | −2299 | −2089 | −3698 | −2004 | −3773 | −2913 | −1652 | 144 | −1753 | −2486 | 2008 | 2860 | −2980 | −3986 | −3403 | 161 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 109(L) | 183 | −1297 | 530 | −2212 | −1245 | −2705 | −1605 | 1003 | −2029 | 2269 | −425 | −2074 | −99 | −1781 | −2114 | −1784 | −1252 | −579 | −1782 | −1423 | 162 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 110(K) | 640 | −2464 | −846 | 531 | −2786 | −634 | −624 | −2534 | 1804 | −2478 | −1554 | −606 | −2062 | 1184 | 1680 | −183 | 159 | −2087 | −2644 | −1966 | 163 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 111(E) | −2632 | −4118 | −726 | 3650 | −4688 | −2682 | −2003 | −4498 | −1128 | −4407 | −3745 | −1375 | −3200 | −1672 | −2399 | −2379 | −470 | −3990 | −4537 | −3731 | 164 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 112(T) | −1378 | −1595 | −2330 | −1769 | 970 | −2639 | −1269 | −1211 | −1461 | −1477 | −820 | −1762 | −2729 | −1384 | 1813 | −551 | 2331 | −1088 | −1586 | 2248 | 165 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −383 | −8312 | −2119 | −894 | −1115 | −701 | −1378 | * | * | | | | | | | | | | | | |
| 113(N) | −791 | −1832 | 50 | 1047 | −305 | −1841 | −525 | −703 | −197 | −251 | −964 | 2489 | −1931 | −140 | −666 | −283 | −731 | −1371 | −2110 | 963 | 166 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −9 | −7937 | −8980 | −894 | −1115 | −1952 | −431 | * | * | | | | | | | | | | | | |

TABLE 3-continued

| | | | | | | | | | | | | | | | | | | | | | |
|---|---|---|---|---|---|---|---|---|---|---|---|---|---|---|---|---|---|---|---|---|---|
| 114(K) | 1001 | −2246 | −618 | 864 | −2565 | −1750 | 758 | −2313 | 2093 | −2260 | −1336 | 584 | −1845 | 635 | −493 | −69 | −7 | −1867 | −2429 | −1749 | 167 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −9 | −7937 | −8980 | −894 | −1115 | −1952 | −431 | * | * | | | | | | | | | | | | |
| 115(N) | −2127 | −2452 | −2097 | −2034 | −660 | −2951 | −1368 | −198 | −1982 | −2230 | −1833 | 3905 | −3222 | −1904 | −2179 | −2236 | −2170 | −1981 | −1308 | 936 | 168 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −9 | −7937 | −8980 | −894 | −1115 | −1952 | −431 | * | * | | | | | | | | | | | | |
| 116(L) | −3492 | −2924 | −5834 | −5257 | 789 | −5550 | −4102 | 1027 | −5024 | 2950 | 84 | −5225 | −4707 | −3869 | −4541 | −4869 | −3343 | −1272 | −2805 | −2830 | 169 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −9 | −7937 | −8980 | −894 | −1115 | −254 | −2629 | * | * | | | | | | | | | | | | |
| 117(D) | 352 | −2696 | 2970 | 584 | −3009 | −2082 | −807 | −2762 | 980 | −2704 | −1796 | −713 | −2225 | −360 | 0 | −1079 | −1159 | −2316 | −2873 | −1202 | 170 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 118(Q) | −379 | −2417 | −845 | 1254 | −2722 | −784 | 874 | −200 | 1175 | −2426 | 150 | −604 | −2055 | 1667 | 717 | −495 | −154 | 224 | −2610 | −1937 | 171 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 119(M) | −1906 | −1631 | −4282 | −3715 | −1632 | −3659 | 1153 | 2809 | −3369 | −1030 | 2854 | −3290 | −3631 | −3031 | −3229 | −2790 | −1858 | 1751 | −2428 | −2079 | 172 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 120(V) | −1675 | −1428 | −4046 | −3465 | −1535 | −3381 | −2355 | 1345 | −3118 | −355 | 657 | −3016 | −3390 | −2785 | −2974 | −980 | 862 | 2932 | −2198 | −1841 | 173 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 121(D) | 893 | −2550 | 2186 | 1147 | −2867 | 374 | −691 | −2620 | 533 | −2564 | −1644 | −634 | −2116 | −235 | 310 | −332 | −1012 | −2171 | −2733 | −2044 | 174 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 122(M) | −1064 | −1348 | −380 | −1330 | −160 | −875 | 767 | 37 | 931 | 35 | 2022 | −1413 | −2427 | −1031 | 1430 | −1349 | −1004 | 428 | −1753 | 1366 | 175 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 123(I) | 624 | −2059 | −4727 | −4136 | 2069 | −4088 | −2966 | 2565 | −3797 | 1421 | −374 | −3739 | −3937 | −3261 | −3569 | −3229 | −2291 | −675 | −2502 | −2265 | 176 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 124(K) | 164 | −2420 | −870 | 864 | −2723 | −1981 | −637 | −2456 | 2548 | −1107 | −1515 | 258 | −2073 | −184 | 396 | −892 | −135 | −384 | −2612 | −1946 | 177 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 125(Q) | −1086 | −2570 | 755 | 2102 | −2887 | −239 | −702 | −2641 | 579 | −2583 | −1663 | −642 | −2127 | 2335 | −145 | −259 | −1028 | −2191 | −2750 | −2060 | 178 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 126(K) | 1143 | −2138 | −1047 | −491 | −2334 | −1268 | −731 | −1997 | 1991 | −845 | 321 | 94 | −2151 | −329 | 582 | −988 | −966 | −1692 | −2398 | 1901 | 179 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 127(M) | −3159 | −2791 | −5237 | −4626 | −1375 | −4924 | −3658 | 241 | −4242 | 1751 | 3379 | −4479 | −4487 | 2834 | −4010 | −4102 | −3045 | −1481 | −2879 | −2882 | 180 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 128(K) | 531 | −2467 | 1672 | 432 | −2787 | −1962 | 842 | −2538 | 1945 | −2482 | −1556 | −597 | −2058 | 764 | −60 | 337 | −933 | −2089 | −2649 | −1966 | 181 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 129(E) | 608 | −2501 | 1336 | 1866 | −2820 | −1977 | −651 | −2572 | 350 | −2516 | −1592 | 79 | −2081 | 847 | −752 | −263 | 1096 | −2122 | −2684 | −1998 | 182 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 130(T) | −1443 | −2096 | −3124 | −3287 | −4401 | −2292 | −3317 | −4200 | −3525 | −4417 | −3519 | −111 | −3045 | −3199 | −3603 | 2044 | 3281 | −3122 | −4592 | −4334 | 183 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |

TABLE 3-continued

| | | | | | | | | | | | | | | | | | | | | | |
|---|---|---|---|---|---|---|---|---|---|---|---|---|---|---|---|---|---|---|---|---|---|
| 131(G) | −2342 | −3617 | −1078 | −1138 | −4177 | 3145 | 602 | −3928 | 852 | −3793 | −3046 | 937 | −3065 | −1284 | −1318 | −2168 | −2338 | −3491 | −3842 | −3252 | 184 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 132(M) | −1412 | −1211 | −3721 | −3109 | −1195 | −3019 | −1922 | 1936 | 153 | 636 | 2441 | −2644 | −3047 | −2378 | −2570 | −2115 | 254 | 1830 | −1783 | −1441 | 185 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 133(K) | −2382 | −3084 | −2779 | −1906 | −3480 | −3186 | −1412 | −563 | 3569 | −2849 | −2226 | −1941 | −3205 | 185 | −333 | −2373 | −2209 | −664 | −3109 | −2822 | 186 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 134(L) | −2611 | −2332 | −4972 | −4508 | −1725 | −4314 | −3571 | −413 | −4186 | 2461 | −619 | −4123 | −180 | −3692 | −3999 | −3552 | −2603 | 2258 | −3031 | −2851 | 187 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 135(L) | −3561 | −3470 | −4972 | −5000 | −2527 | −4319 | −4274 | −2132 | −4722 | 2904 | −1522 | −4638 | 2196 | −4380 | −4502 | −4088 | −3732 | −2706 | −3760 | −3674 | 188 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 136(W) | −4178 | −3738 | −5370 | −5358 | −1338 | −4715 | −2806 | −2734 | −4647 | −2000 | 3289 | −4520 | −4875 | −4300 | −4355 | −4520 | −4225 | −3205 | 5740 | −1122 | 189 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 137(N) | 142 | −1989 | −2878 | −2702 | −3612 | 1917 | −2689 | −3274 | −2730 | −3523 | −2701 | 2927 | −2900 | −2506 | −2962 | −414 | −1684 | 1320 | −3855 | −3498 | 190 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 138(T) | −3014 | −3363 | −4795 | −5109 | −5200 | −3551 | −4612 | −5219 | −5081 | −5386 | −4862 | −4270 | −4241 | −4876 | −4829 | −3277 | 4049 | −4432 | −4902 | −5198 | 191 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 139(A) | 2832 | −1972 | −4244 | −4339 | −4463 | −760 | −3712 | −4243 | −4136 | −4497 | −3564 | −2941 | −3041 | −3711 | −3978 | 1060 | 1917 | −3080 | −4688 | −4571 | 192 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 140(N) | −2239 | −3351 | −994 | −1271 | −4465 | −2566 | −2158 | −4418 | −2073 | −4368 | −3639 | 3979 | −3136 | 445 | −2533 | 245 | −2444 | −3731 | −4441 | −3700 | 193 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 141(M) | −1488 | 1901 | −3790 | −3168 | −1094 | −3058 | −1949 | −467 | −2783 | 2250 | 2832 | −414 | −3076 | −2387 | −2597 | −2155 | −1430 | 533 | −1764 | −1453 | 194 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 142(F) | −5308 | −4420 | −5610 | −5948 | 4547 | −4921 | −3048 | −4656 | −5852 | −3992 | −4112 | −4995 | −5217 | −5110 | −5315 | −5363 | −5399 | −4866 | −2341 | −1279 | 195 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 143(T) | −1333 | −1921 | −3518 | −3324 | −3642 | 123 | −3003 | −3307 | −3160 | −3578 | 1028 | −2602 | −2954 | −2918 | −3250 | 1815 | 3158 | −2607 | −3929 | −3640 | 196 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 144(H) | −2587 | −4410 | 687 | −793 | −4549 | −2586 | 4208 | −4506 | −1989 | −4378 | −3682 | 2832 | −3090 | 194 | −2726 | −2268 | −2637 | −4002 | −4523 | −3562 | 197 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 145(P) | −777 | −3430 | −1097 | −93 | −4208 | −2659 | −1777 | −3899 | 593 | −3828 | −3084 | −1470 | 3745 | −1415 | −1541 | −2135 | −2319 | −3430 | −3945 | −3364 | 198 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 146(R) | −550 | −1933 | −2864 | −2364 | −2830 | −927 | −2070 | −2310 | −1691 | −2646 | −1918 | −2140 | −2867 | −1879 | 3417 | −1633 | −92 | 1325 | −3074 | −2717 | 199 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 147(F) | −4998 | −3935 | −5388 | −5739 | 3810 | −5262 | −1482 | −3879 | −5300 | −3188 | −3284 | −3899 | −5127 | −4036 | −4670 | −4527 | −4855 | −4043 | −729 | 3525 | 200 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |

TABLE 3-continued

| | | | | | | | | | | | | | | | | | | | | | |
|---|---|---|---|---|---|---|---|---|---|---|---|---|---|---|---|---|---|---|---|---|---|
| 148(M) | −1239 | −1212 | −2845 | −2242 | −1184 | −92 | −1512 | −579 | 1562 | 39 | 2941 | −2060 | −2743 | −1703 | −1901 | −1745 | −1181 | 1944 | −1681 | −1320 | 201 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 149(H) | 593 | −3227 | 1964 | 442 | −3513 | −2264 | 3263 | −3299 | −948 | −3231 | −2358 | 1914 | −2532 | −764 | −1529 | −462 | −1628 | −2836 | −3408 | −2646 | 202 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 150(G) | −4740 | −4445 | −5364 | −5738 | −6131 | 3840 | −5265 | −6903 | −6030 | −6539 | −6235 | −5426 | −5034 | −5814 | −5624 | −5041 | −5115 | −6153 | −5123 | −6096 | 203 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 151(W) | −204 | 887 | 46 | 246 | −204 | −619 | 891 | −475 | 338 | −941 | 659 | 291 | −334 | 598 | 147 | −143 | 7 | −471 | 1260 | 199 | 204 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 152(A) | 3079 | −1981 | −4321 | −4534 | −4388 | 1735 | −3806 | −3957 | −4337 | −4384 | −3516 | −3010 | −3078 | −3869 | −4090 | −1647 | −1847 | −409 | −4664 | −4550 | 205 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 153(A) | 2589 | −1888 | −3886 | −3806 | 2401 | −778 | −3205 | −3235 | −3632 | −3529 | −2743 | −2783 | −3003 | −3276 | −3573 | 1465 | −1739 | −2566 | −3839 | −3512 | 206 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 154(T) | −1493 | −2101 | −3952 | −4245 | −4536 | −2355 | −3794 | −4349 | −4195 | −4644 | −3761 | −2999 | −3149 | −3828 | −4010 | −557 | 3902 | −3205 | −4753 | −4602 | 207 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 155(S) | 540 | −2055 | −3002 | −2865 | −4153 | −2245 | −2899 | −3915 | −2898 | −4091 | −3185 | 1991 | −2931 | −2672 | −3128 | 2781 | 1118 | −2953 | −4296 | −3964 | 208 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 156(C) | −1362 | 3283 | −2411 | −2080 | −3450 | −2276 | −2150 | −3137 | −1861 | −3298 | −2470 | 2369 | 2823 | −1857 | −547 | −338 | −1614 | −2541 | −3575 | −3147 | 209 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 157(D) | −1060 | −2512 | 2344 | 682 | 408 | −2001 | −688 | −2563 | −290 | −2522 | −1608 | 1941 | −2113 | −236 | 126 | 73 | −1002 | −2126 | −2701 | −334 | 210 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 158(A) | 2203 | −1406 | −2316 | −1761 | 1179 | −2422 | −1413 | −1077 | −1508 | −1393 | −717 | −1726 | 1050 | −1393 | 1435 | −1489 | −1163 | 75 | −1934 | −1529 | 211 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 159(D) | −1108 | −2589 | 2572 | 1474 | −2902 | −2021 | −725 | −2655 | 395 | −2602 | −1685 | 326 | −2145 | −272 | −851 | 251 | −169 | −2207 | 1553 | −2081 | 212 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 160(V) | −2769 | −2275 | −5444 | −5141 | −2907 | −5216 | −5273 | 1475 | −5092 | −1669 | −1617 | −4931 | −5004 | −5033 | −5244 | −4603 | −2770 | 3537 | −4643 | −4129 | 213 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 161(F) | −3052 | −2695 | −4546 | −4247 | 3203 | −4202 | −1494 | −2262 | −3699 | −2242 | −1900 | −3317 | −4178 | −3190 | 2010 | −3345 | −2975 | 767 | −879 | 2654 | 214 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 162(A) | 3042 | −2119 | −3426 | −3206 | −4202 | −2348 | −2904 | −3925 | −2474 | −4083 | −3222 | −2583 | −3032 | −2685 | 1719 | 534 | −1849 | −3011 | −4246 | −4000 | 215 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 163(Y) | −3964 | −3336 | −5040 | −5039 | 1445 | −4787 | −1468 | −3083 | −4580 | −2777 | 836 | −3655 | −4704 | −3678 | 1014 | −3973 | −3862 | −3132 | 2650 | 4219 | 216 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 164(A) | 3397 | −1996 | −4237 | −4525 | −4627 | −310 | −3879 | −4438 | −4443 | −4696 | −3743 | −3000 | −3071 | −3927 | −4178 | 218 | −1854 | −3173 | −4847 | −4779 | 217 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |

TABLE 3-continued

| | | | | | | | | | | | | | | | | | | | | | |
|---|---|---|---|---|---|---|---|---|---|---|---|---|---|---|---|---|---|---|---|---|---|
| 165(A) | 2613 | −1126 | −3505 | −2891 | −69 | −991 | −1733 | 690 | −2525 | 734 | −274 | −2447 | −2880 | −2171 | −2378 | −1919 | −1233 | −16 | −1624 | −1284 | 218 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 166(A) | 2400 | −1805 | −2420 | −1934 | −2555 | 164 | −1841 | −2139 | −1713 | −2410 | −1660 | −1850 | −2680 | −1637 | 1676 | −1432 | 551 | 718 | −2846 | −2430 | 219 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 167(Q) | −3216 | −3916 | −3036 | −2340 | −4750 | −3581 | −1704 | −4191 | 2500 | −3828 | −3184 | −2315 | −3640 | 3726 | −379 | −3075 | −2950 | −3942 | −3629 | −3505 | 220 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 168(V) | −1889 | −1609 | −4294 | −3746 | −1809 | −3673 | −2738 | 1337 | −3430 | 223 | −879 | −3321 | −3670 | −3122 | −3314 | −452 | 114 | 3027 | −2565 | −2197 | 221 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 169(K) | −1988 | −1815 | −3867 | −3265 | −61 | −3579 | −2411 | 608 | 3002 | 1068 | −398 | −3036 | −3519 | −2605 | −2843 | −2673 | −1920 | 280 | −2274 | −1989 | 222 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 170(H) | −256 | −2524 | −929 | 393 | −2858 | −2038 | 2453 | −2595 | 2209 | −2532 | −1615 | 617 | −2127 | −214 | 1169 | −956 | 416 | −2154 | −2687 | −2028 | 223 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 171(A) | 1760 | −2287 | −1318 | −859 | −3091 | 1259 | −1172 | −2823 | −819 | −2844 | −1946 | 1423 | −2360 | 334 | −1298 | 1120 | 170 | −2306 | −3051 | −2433 | 224 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 172(M) | −3851 | −3263 | −6245 | −5660 | −1466 | −5999 | −4689 | 2110 | −5449 | 2475 | 2821 | −5714 | −5087 | −4261 | −4955 | −5348 | −3701 | −1503 | −3271 | −3471 | 225 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 173(D) | −2907 | −4984 | 3077 | 2640 | −5091 | −2646 | −2094 | −5089 | −2514 | −4917 | −4353 | 575 | −3236 | −1786 | −3527 | −2508 | −3007 | −4525 | −5119 | −3978 | 226 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 174(I) | 1132 | −1695 | −4439 | −3899 | −1866 | −3834 | −2908 | 2259 | −3592 | 1435 | −900 | −3481 | −3802 | −3276 | −3473 | −2983 | −597 | 1521 | −2695 | −2335 | 227 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 175(T) | 2228 | −1974 | −4202 | −4278 | −4460 | 1638 | −3685 | −4242 | −4085 | −4491 | −3558 | −2925 | −3038 | −3671 | −3948 | 523 | 2255 | −3080 | −4681 | −4557 | 228 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 176(K) | 692 | −1650 | −1775 | −1196 | −1722 | −2391 | 1742 | 714 | 2556 | −1538 | −836 | −1336 | −2470 | −892 | −1164 | −1384 | −1131 | 634 | −2040 | −1598 | 229 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 177(E) | −1319 | −2706 | −1195 | 2572 | −3079 | −2247 | −809 | −2780 | 1335 | −2691 | −1802 | −886 | −2327 | 234 | 1489 | −1200 | −369 | −2360 | −2812 | 310 | 230 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 178(L) | −3875 | −3291 | −6254 | −5672 | −1457 | −5994 | −4687 | −834 | −5446 | 3095 | 1236 | −5724 | −5089 | −4257 | −4949 | −5349 | −3726 | 117 | −3263 | −3460 | 231 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 179(G) | −2536 | −3114 | −2855 | −3225 | −5099 | 3685 | −3752 | −5315 | −4127 | −5358 | −4624 | 59 | −3784 | −3697 | −4300 | −2703 | −2949 | −4249 | −4910 | −4848 | 232 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 180(A) | 2480 | −2007 | −3784 | −3834 | −4416 | 2311 | −3496 | −4197 | −3742 | −4425 | −3503 | −2804 | −3029 | −3419 | −1816 | 1068 | −1817 | −3076 | −4613 | −4438 | 233 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 181(E) | −2358 | −3954 | −688 | 3489 | −4290 | −2588 | −1658 | −4076 | −137 | −3947 | −3188 | −1202 | −2990 | −287 | −1831 | −242 | −2356 | −3617 | −4074 | −3314 | 234 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |

TABLE 3-continued

| | | | | | | | | | | | | | | | | | | | | | |
|---|---|---|---|---|---|---|---|---|---|---|---|---|---|---|---|---|---|---|---|---|---|
| 182(N) | −1197 | −1819 | −2024 | −1565 | −2415 | −764 | −1594 | −14 | −1466 | −2263 | −1508 | 3406 | −2581 | −1353 | −1820 | −247 | 1313 | −893 | −2696 | −2243 | 235 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 183(Y) | −4914 | −3888 | −5384 | −5705 | 1863 | −5254 | −1485 | −3696 | −5262 | −1015 | −3107 | −3892 | −5106 | −4013 | −4642 | −4501 | −4770 | −3900 | −732 | 4560 | 236 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 184(V) | −3382 | −3135 | −5319 | −5407 | −3802 | −4379 | −4923 | −1179 | −5325 | −2915 | −2860 | −4909 | −4787 | −5200 | −5168 | −4266 | −3561 | 3821 | −4638 | −4461 | 237 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 185(F) | −245 | −1976 | −4569 | −3955 | 3611 | −3896 | −2734 | −630 | −3595 | 1079 | 1156 | −3542 | −3766 | −3052 | −3355 | −3019 | −2168 | 266 | −2302 | −2075 | 238 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 186(W) | −6178 | −4896 | −5848 | −6204 | −4109 | −4952 | −4743 | −6650 | −6203 | −5992 | −6031 | −5971 | −5371 | −6028 | −5699 | −6531 | −6329 | −6559 | 6291 | −3733 | 239 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 187(G) | −3000 | −3383 | −4355 | −4713 | −5554 | 3708 | −4577 | −5789 | −5128 | −5785 | −5102 | −4100 | 282 | −4765 | −4941 | −3242 | −3441 | −4699 | −5042 | −5532 | 240 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 188(G) | −4740 | −4445 | −5364 | −5738 | −6131 | 3840 | −5265 | −6903 | −6030 | −6539 | −6235 | −5426 | −5034 | −5814 | −5624 | −5041 | −5115 | −6153 | −5123 | −6096 | 241 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 189(R) | −5156 | −4675 | −5377 | −4998 | −5777 | −4641 | −4103 | −6271 | −3143 | −5805 | −5439 | −4840 | −4993 | −4014 | 4230 | −5318 | −5151 | −5964 | −4773 | −5292 | 242 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 190(E) | −4894 | −4877 | −3044 | 3932 | −5916 | −4252 | −4190 | −6541 | −4583 | −6183 | −5913 | −3747 | −4767 | −4175 | −4884 | −4792 | −5049 | −6107 | −5083 | −5486 | 243 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 191(G) | −4740 | −4445 | −5364 | −5738 | −6131 | 3840 | −5265 | −6903 | −6030 | −6539 | −6235 | −5426 | −5034 | −5814 | −5624 | −5041 | −5115 | −6153 | −5123 | −6096 | 244 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 192(Y) | 1128 | −2151 | −3615 | −3697 | −2169 | −2532 | −2750 | −3414 | −3639 | −3566 | −2927 | −2840 | −3221 | −3299 | −3585 | 346 | −2022 | −2806 | −2762 | 4321 | 245 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 193(E) | −380 | −3053 | 283 | 3153 | −3334 | −2232 | −1107 | −3096 | −834 | −3054 | 1184 | −859 | −2470 | 595 | −1389 | −1391 | −1518 | −2659 | −3248 | −2518 | 246 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 194(T) | −1103 | 1142 | −2635 | −2048 | 226 | −2529 | −1370 | −640 | −1798 | −977 | −315 | 492 | −2600 | −1565 | −1879 | 1469 | 2053 | 325 | −1553 | 1510 | 247 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 195(L) | −2451 | −3826 | 1344 | 380 | −3974 | −118 | −1886 | −3714 | −2079 | 2668 | −3117 | −1233 | −3073 | −1582 | −2813 | −2228 | −2503 | −3386 | −4143 | −3340 | 248 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 196(W) | 386 | −1134 | −2676 | −2101 | −1119 | −347 | 779 | −682 | −1838 | 2157 | −357 | −1927 | −2623 | −1612 | −1910 | 39 | −1078 | −582 | 2407 | −1210 | 249 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 197(N) | 1013 | −2090 | −2983 | −3038 | −4320 | −2272 | −3125 | −4091 | −3254 | −4290 | −3387 | 3818 | −2998 | −2951 | −3423 | −234 | 228 | −3062 | −4487 | −4194 | 250 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 198(T) | −1798 | −2527 | −2472 | −2321 | −4196 | −165 | −2323 | −3864 | 1571 | −3911 | −3113 | −2201 | −3114 | −2006 | −1736 | −1923 | 3444 | −3160 | −4006 | −3686 | 251 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |

TABLE 3-continued

| | | | | | | | | | | | | | | | | | | | | | |
|---|---|---|---|---|---|---|---|---|---|---|---|---|---|---|---|---|---|---|---|---|---|
| 199(D) | −2628 | −4493 | 3630 | −795 | −4689 | −2595 | −1891 | −4588 | 78 | −4447 | −3759 | 761 | −3106 | 1043 | −2749 | −2297 | −2679 | −4074 | −4622 | −3654 | 252 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 200(M) | −97 | −1073 | −3318 | −2701 | −998 | −2739 | −1606 | −472 | −2346 | 1093 | 3659 | −2307 | −2785 | 467 | −2231 | −1817 | −59 | 1113 | −1534 | −1193 | 253 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 201(K) | −294 | −2512 | −898 | 178 | −2843 | −95 | −659 | −2584 | 2469 | −2522 | −1603 | 266 | −2109 | 522 | 1551 | −254 | −990 | −2140 | −2680 | −2014 | 254 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 202(W) | −204 | 887 | 46 | 246 | −204 | −619 | 891 | −475 | 338 | −941 | 659 | 291 | −334 | 598 | 147 | −143 | 7 | −471 | 1260 | 199 | 255 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 203(R) | 515 | −2100 | −67 | −484 | 1101 | −2050 | −726 | −1947 | 420 | 512 | −1227 | −760 | −2139 | 1266 | 1890 | −975 | −948 | −993 | −2369 | −1782 | 256 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 204(E) | 1191 | −2588 | −1433 | 3261 | −3616 | −2449 | −2074 | −2773 | −1979 | −3329 | −2647 | −1665 | −2946 | −1764 | −2429 | −1806 | −1937 | −133 | −3820 | −3246 | 257 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 205(L) | −1513 | −1884 | −2260 | −1562 | −1940 | −2676 | −1221 | −1499 | 519 | 2067 | 848 | −1624 | −2718 | 1781 | 725 | −1719 | −1418 | −1369 | 1760 | −1802 | 258 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 206(D) | −745 | −4362 | 3177 | 2316 | −4570 | −2552 | −1843 | −4464 | −1204 | −4345 | −3627 | −1146 | −3050 | −1496 | −2798 | −856 | −2573 | −3948 | −4537 | −3568 | 259 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 207(H) | −1159 | −2582 | −194 | −438 | −2895 | −2097 | 3162 | −2638 | −245 | −2581 | −1678 | 2194 | −2196 | 1039 | 1482 | −1040 | −1092 | −2210 | 1571 | −2082 | 260 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 208(M) | −667 | −1277 | −3818 | −3186 | 164 | −3048 | −1914 | 1188 | −2791 | 1720 | 3132 | −2694 | −3054 | −2373 | −2581 | −2141 | −1411 | 370 | −1706 | 1039 | 261 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 209(A) | 2605 | −2502 | −1660 | −1121 | −3271 | 74 | −1239 | −2944 | 508 | −2930 | −2076 | −1300 | −2572 | −823 | 1599 | −500 | −1463 | −2485 | −3089 | −2569 | 262 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 210(R) | −254 | −2474 | −853 | 1591 | −2798 | −1977 | −630 | −2545 | 1166 | −2488 | −1564 | 387 | −2070 | 471 | 2128 | −309 | 332 | −2098 | −2652 | −1975 | 263 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 211(F) | 948 | −1050 | −3245 | −2644 | 3385 | −798 | −1571 | 28 | −2300 | −901 | 1472 | −2239 | −893 | −1973 | −2197 | −1725 | −1113 | −475 | −1528 | −1174 | 264 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 212(F) | −2629 | −2312 | −4914 | −4321 | 2717 | −4278 | −2852 | −858 | −3964 | 1977 | 2554 | −3882 | −4056 | −3300 | −3668 | −3416 | −2538 | −122 | −2251 | 1119 | 265 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 213(H) | −1020 | −2488 | 1097 | −309 | −2812 | −1983 | 2931 | −2560 | 749 | −2502 | −1579 | 918 | −2079 | 1776 | 469 | −899 | 752 | −2112 | −2667 | −1988 | 266 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 214(M) | −359 | −1579 | −4116 | −3488 | 569 | −3396 | −2253 | 143 | −3109 | 1631 | 3928 | −3036 | −3351 | −2647 | −2893 | −2497 | −246 | −756 | −1968 | −1708 | 267 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 215(A) | 2548 | 947 | −3783 | −3180 | −1231 | −3043 | −2001 | −310 | −2809 | 672 | 1303 | −2705 | −3092 | −2442 | −2643 | −2151 | −1419 | 1111 | −1853 | −1521 | 268 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |

TABLE 3-continued

| | | | | | | | | | | | | | | | | | | | | | |
|---|---|---|---|---|---|---|---|---|---|---|---|---|---|---|---|---|---|---|---|---|---|
| 216(V) | 787 | 844 | −1857 | −1289 | −1397 | −389 | 570 | 555 | 958 | −1259 | −562 | −1384 | −2419 | −995 | 817 | −1338 | −1009 | 1831 | −1782 | −1359 | 269 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 217(D) | −208 | −3213 | 2902 | 1429 | −3501 | −609 | −1166 | −3288 | −924 | −3217 | −2340 | 436 | −2518 | 976 | −1504 | −420 | −1608 | −2823 | −3391 | −2630 | 270 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 218(Y) | −4881 | −3957 | −5031 | −5318 | −128 | −5096 | 2506 | −3985 | −4860 | −3314 | −3388 | −3861 | −5053 | −3965 | −4419 | −4476 | −4777 | −4116 | −844 | 4614 | 271 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 219(A) | 2495 | −1569 | −1878 | −1335 | −1756 | −621 | −1246 | −153 | 939 | −1605 | −891 | −1427 | −2466 | −1072 | −1499 | −411 | −1115 | 571 | −2102 | −1665 | 272 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 220(K) | −986 | −2457 | −27 | 762 | −2778 | −1959 | 1449 | −834 | 2054 | −2472 | −1546 | 980 | −2052 | 603 | 1183 | −866 | 205 | −2079 | −2639 | −1958 | 273 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 221(E) | −254 | −2564 | 1369 | 2076 | −2882 | −2009 | −700 | −2635 | 1371 | −2578 | −1658 | −642 | −2125 | −245 | −31 | 858 | −1025 | −2185 | −2745 | −2056 | 274 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 222(I) | −2688 | −3306 | −3275 | −2169 | −3815 | −3397 | −1438 | 3178 | 1262 | −3125 | −2452 | −2120 | −3365 | 1862 | 561 | −2654 | −2443 | −3013 | −3178 | −2982 | 275 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 223(G) | −2637 | −3974 | 390 | −1153 | −5020 | 3488 | −2357 | −5035 | −2776 | −4946 | −4322 | 291 | −3293 | −2075 | −3657 | −2438 | −2858 | −4295 | −5047 | −4127 | 276 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 224(Y) | −4400 | −3612 | −5188 | −5335 | 3494 | −5009 | 1099 | −3457 | −4913 | −1074 | −2941 | −3762 | −4903 | −3843 | −4408 | −919 | −4284 | −3538 | −732 | 3504 | 277 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 225(D) | −991 | −2464 | 1721 | 213 | −2784 | 477 | 823 | −2534 | 919 | −1132 | −1553 | 893 | −2056 | 1223 | −713 | −871 | 944 | −2085 | −2647 | −1964 | 278 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 226(G) | 624 | −1134 | −2638 | −2059 | −1134 | 2287 | −1399 | −199 | −1811 | 555 | −355 | −1900 | 408 | −1582 | −1898 | −1575 | −499 | −578 | −1599 | 672 | 279 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 227(Q) | −1134 | −2497 | −1028 | −462 | −2811 | −2101 | −720 | −622 | 101 | −2489 | −1598 | 278 | −1086 | 2837 | 1581 | −1029 | 1381 | −2117 | −2667 | −2040 | 280 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 228(F) | −3742 | −3197 | −6068 | −5484 | 3900 | −5732 | −4235 | 207 | −5233 | 1117 | 1544 | −5389 | −4953 | −4113 | −4759 | −5019 | −3594 | −1653 | −3024 | −2977 | 281 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 229(L) | 1551 | −2659 | −4811 | −4712 | −2094 | −3608 | −3887 | −1436 | −4392 | 2837 | −1006 | −3969 | −4022 | −3904 | −4164 | −3002 | −2754 | −1827 | −3457 | −3347 | 282 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 230(I) | −3359 | −2829 | −5847 | −5421 | −1855 | −5595 | −4779 | 3551 | −5239 | 1256 | −646 | −5322 | −5043 | −4488 | −4999 | −4988 | −3295 | −533 | −3603 | −3558 | 283 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 231(E) | −4894 | −4877 | −3044 | +Z,31 | −5916 | −4252 | −4190 | −6541 | −4583 | −6183 | −5913 | −3747 | −4767 | −4175 | −4884 | −4792 | −5049 | −6107 | −5083 | −5486 | 284 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 232(P) | −5161 | −4627 | −5479 | −5844 | −6102 | −4639 | −5314 | −6971 | −6053 | −6538 | −6341 | −5638 | 4316 | −5917 | −5641 | −5486 | −5496 | −6390 | −5102 | −6043 | 285 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |

TABLE 3-continued

| | | | | | | | | | | | | | | | | | | | | | |
|---|---|---|---|---|---|---|---|---|---|---|---|---|---|---|---|---|---|---|---|---|---|
| 233(K) | −4797 | −4587 | −4692 | −4321 | −5682 | −4474 | −3615 | −5879 | +Z,32 | −5471 | −5024 | −4244 | −4783 | −3408 | −2493 | −4857 | −4726 | −5584 | −4639 | −5025 | 286 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 234(P) | −513 | −2636 | −4047 | −4375 | −4929 | −2842 | −4112 | −4853 | −4533 | −5052 | −4279 | −3436 | 4155 | −4192 | −4369 | −2335 | −2548 | −3772 | −4881 | −4955 | 287 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 235(K) | −1854 | −3064 | −1724 | −1121 | −3517 | −2674 | −1100 | −3136 | 2701 | −3003 | 1908 | 2081 | −2743 | 1586 | −404 | −1736 | −1732 | −2775 | −3062 | −2601 | 288 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 236(E) | −4894 | −4877 | −3044 | 3932 | −5916 | −4252 | −4190 | −6541 | −4583 | −6183 | −5913 | −3747 | −4767 | −4175 | −4884 | −4792 | −5049 | −6107 | −5083 | −5486 | 289 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 237(P) | −5161 | −4627 | −5479 | −5844 | −6102 | −4639 | −5314 | −6971 | −6053 | −6538 | −6341 | −5638 | 4316 | −5917 | −5641 | −5486 | −5496 | −6390 | −5102 | −6043 | 290 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 238(T) | −1947 | −2421 | −3165 | −2413 | −2978 | −2880 | −1827 | −2467 | −892 | −2555 | 1753 | −2247 | −3160 | −1548 | 2098 | −2129 | 3164 | −2270 | −3058 | −2755 | 291 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 239(K) | −484 | −2389 | −1045 | −493 | −2703 | 1249 | −755 | −2401 | 2460 | −2412 | 376 | −776 | −2191 | 560 | −730 | −1027 | 996 | −2019 | −2628 | −2010 | 292 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 240(H) | −3186 | −4015 | 2118 | −1712 | 238 | −3267 | 4734 | −4101 | −2845 | −3764 | −3475 | −1967 | −3709 | −2311 | −3399 | −2927 | −3243 | −3909 | −2018 | −872 | 293 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 241(Q) | −2896 | −3052 | −3270 | −3166 | −2696 | −3713 | −2865 | 2002 | −2306 | −2048 | −2010 | −3126 | −4018 | 3975 | −2353 | −3246 | −2972 | −1751 | −3437 | −2918 | 294 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 242(Y) | −4742 | −3801 | −5383 | −5639 | 926 | −5232 | −1545 | −3295 | −5204 | 588 | −2693 | −3920 | −5066 | −3993 | −4610 | −4477 | −4604 | −3605 | −791 | 4507 | 295 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 243(D) | −3103 | −3191 | 3532 | −2696 | 707 | −3852 | −2334 | −1817 | −3417 | 1062 | −1316 | −2809 | −4046 | −2871 | −3673 | −3321 | −3098 | −2210 | −2109 | −1168 | 296 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 244(F) | −78 | −1005 | −3333 | −2714 | 2786 | −2679 | −1509 | −502 | −2343 | −852 | −208 | −2267 | 1364 | −1992 | −2198 | −1758 | 336 | 525 | 1608 | 1606 | 297 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 245(D) | −2674 | −3777 | 3647 | −1466 | −4960 | −2802 | −2593 | −4914 | −2986 | −4935 | −4319 | −1779 | −3430 | −2333 | −3759 | −2551 | 1960 | −4212 | −4943 | −4224 | 298 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 246(V) | 1871 | −1480 | −3615 | −3153 | −1890 | −2627 | −2297 | −306 | −2859 | −1673 | −1071 | −2602 | −2996 | −2560 | −2812 | 319 | 356 | 2553 | −2416 | −2073 | 299 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 247(A) | 2611 | −2786 | −991 | 446 | −3556 | 1526 | −1508 | −3306 | −1293 | −3323 | −2474 | −1193 | −2662 | 380 | −1815 | −724 | −1690 | −2792 | −3540 | −2870 | 300 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 248(T) | −1575 | −2397 | −1716 | −1668 | −3555 | −2353 | 2795 | −3355 | −1840 | −3474 | −2665 | −42 | −2866 | −1754 | −2195 | −42 | 3311 | −2773 | −3678 | −3134 | 301 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 249(A) | 1906 | −1213 | −2611 | −2044 | −1274 | −749 | −1459 | −806 | −1803 | −1153 | 1226 | −1896 | −2621 | −1594 | −618 | −1555 | 1741 | 1404 | −1729 | −1356 | 302 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |

TABLE 3-continued

| | | | | | | | | | | | | | | | | | | | | | |
|---|---|---|---|---|---|---|---|---|---|---|---|---|---|---|---|---|---|---|---|---|---|
| 250(I) | −1289 | −1106 | −3622 | −2990 | 447 | −2843 | 556 | 2280 | −2590 | 1525 | 1089 | −2484 | −2875 | −2195 | −2387 | −1931 | −1228 | 105 | −1521 | 1527 | 303 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 251(A) | 2994 | −2060 | −3318 | −3466 | −4480 | 1477 | −3420 | −4277 | −3713 | −4492 | −3567 | 555 | −3034 | −3314 | −3765 | −61 | −1848 | −3134 | −4669 | −4455 | 304 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 252(F) | −4510 | −3775 | −5456 | −5636 | 4401 | −5131 | −2010 | −2624 | −5257 | −859 | −2061 | −4236 | −5048 | −4187 | −4724 | −4603 | −4458 | −3115 | −1246 | −111 | 305 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 253(W) | −204 | 887 | 46 | 246 | −204 | −619 | 891 | −475 | 338 | −941 | 659 | 291 | −334 | 598 | 147 | −143 | 7 | −471 | 1260 | 199 | 306 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 254(L) | −3584 | −3041 | −6020 | −5465 | −1547 | −5724 | −4559 | 2056 | −5257 | 2650 | 1509 | −5420 | −4986 | −4234 | −4854 | −5036 | −3464 | −85 | −3297 | −3428 | 307 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 255(Q) | −1021 | 248 | 260 | 920 | −2812 | −1989 | 1097 | −2558 | 2005 | −2499 | −1576 | −625 | −2082 | 2156 | 985 | −901 | −958 | −2111 | −2661 | −1987 | 308 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 256(Q) | −387 | −2464 | −846 | 769 | −2785 | −1226 | −626 | −2533 | 1569 | −2478 | −1554 | −607 | −2064 | 1918 | 125 | −280 | 1845 | −2086 | −2645 | −1968 | 309 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 257(Y) | −4615 | −3726 | −5293 | −5520 | 1958 | −5121 | 2666 | −3552 | −5082 | 1275 | −3001 | −3826 | −4994 | −3925 | −4517 | −4347 | −4486 | −3686 | −731 | 3736 | 310 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 258(G) | −747 | −4382 | 2188 | 1513 | −4595 | 2379 | −1856 | −4494 | −2029 | −4373 | −3659 | 909 | −3058 | −1510 | −2839 | −2220 | −2589 | −3973 | −4566 | −3588 | 311 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 259(L) | −2849 | −3066 | −3826 | −2761 | −2395 | −3664 | 902 | −2487 | −656 | 2698 | −1855 | −2584 | −3649 | −1532 | 1920 | −2997 | −2656 | −2597 | −2707 | −2185 | 312 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 260(D) | −1081 | −2552 | 2320 | 1262 | −2865 | −682 | −702 | −2615 | 533 | −2565 | 328 | −642 | 1396 | −249 | −820 | −956 | 36 | −2170 | −2738 | −2050 | 313 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 261(K) | −1509 | −3060 | 1864 | 1703 | −3356 | −449 | −1058 | −3134 | 2145 | −3064 | −2175 | 56 | −2431 | 967 | −1320 | −1342 | −1471 | −2672 | −3234 | −2495 | 314 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 262(H) | −1002 | −2068 | 1504 | 952 | −2245 | −2050 | 1617 | −504 | −395 | −182 | 481 | −767 | −2139 | −339 | 266 | −215 | −39 | −604 | −2345 | 1579 | 315 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 263(F) | −2939 | −2542 | −4828 | −4519 | 3955 | −4337 | −1860 | 649 | −4141 | −1500 | −1361 | −3601 | −4252 | −3447 | −3825 | −3494 | −2868 | 491 | −1216 | 1328 | 316 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 264(K) | −3285 | −3787 | −3212 | −3069 | −5220 | 1761 | −2834 | −5042 | 3532 | −4797 | −4163 | −3047 | −4026 | −2528 | −1831 | −3329 | −3400 | −4504 | −4387 | −4430 | 317 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 265(L) | −3149 | −2690 | −5597 | −5054 | 1255 | −5177 | −4100 | 997 | −4810 | 2411 | −428 | −4847 | −4706 | −4033 | −4515 | −4417 | −3061 | 1824 | −3171 | −3136 | 318 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 266(N) | −4313 | −4359 | −3728 | −4093 | −5358 | −4169 | −4424 | −6344 | −4850 | −6082 | −5725 | 4411 | −4732 | −4593 | −4904 | −4442 | −4627 | −5689 | −4872 | −5035 | 319 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |

TABLE 3-continued

| | | | | | | | | | | | | | | | | | | | | | |
|---|---|---|---|---|---|---|---|---|---|---|---|---|---|---|---|---|---|---|---|---|---|
| 267(I) | −2513 | −2147 | −4957 | −4435 | −1823 | −4442 | −3529 | 2351 | −4159 | 1722 | −717 | −4099 | 1949 | −3712 | −4007 | −3631 | −2464 | 904 | −3048 | −2816 | 320 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 268(E) | −4894 | −4877 | −3044 | 3932 | −5916 | −4252 | −4190 | −6541 | −4583 | −6183 | −5913 | −3747 | −4767 | −4175 | −4884 | −4792 | −5049 | −6107 | −5083 | −5486 | 321 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 269(A) | 2088 | 1365 | −3378 | −2828 | 487 | 698 | −1799 | −836 | −2493 | −1210 | −556 | −2334 | −2768 | −2166 | −2396 | −1684 | 1302 | 1028 | −1808 | −1465 | 322 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 270(N) | 11 | −2335 | −2305 | −2622 | −4638 | 1373 | −3163 | −4488 | −3477 | −4658 | −3784 | 3837 | −3115 | −3000 | −3729 | −1807 | −2052 | −3368 | −4789 | −4432 | 323 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 271(H) | −5506 | −4764 | −5029 | −5331 | −4362 | −4732 | 5444 | −6634 | −5266 | −6082 | −5977 | −5274 | −5186 | −5341 | −5054 | −5722 | −5705 | −6336 | −4332 | −3976 | 324 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 272(A) | 3116 | −3101 | −1551 | 1884 | −4671 | −2707 | −2717 | −4449 | −2864 | −4585 | −3878 | −2034 | −3343 | −2468 | −3340 | −2287 | −2556 | −3712 | −4673 | −4159 | 325 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 273(T) | −1255 | −2072 | −1391 | −875 | −1774 | −2311 | −946 | −1843 | −693 | −1995 | −1243 | 873 | −2410 | 1832 | −1084 | −1286 | 2808 | −1615 | 1353 | 355 | 326 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 274(M) | −4049 | −3435 | −6360 | −5790 | −1437 | −6127 | −4754 | −942 | −5533 | 2883 | 3227 | −5895 | −5154 | −4292 | −4999 | −5549 | −3886 | −1796 | −3261 | −3457 | 327 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 275(A) | 3290 | −2018 | −4238 | −4530 | −4608 | −2288 | −3883 | −4417 | −4424 | −4691 | −3755 | −3019 | −3092 | −3936 | −4162 | 1337 | −1879 | −3180 | −4829 | −4744 | 328 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 276(G) | −2006 | −2603 | −2686 | −2983 | −51 | 3566 | −2982 | −4201 | −3636 | −4266 | −3635 | −99 | −3416 | −3230 | −3787 | −2185 | −2398 | −3434 | −3413 | −2529 | 329 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 277(H) | −3898 | −3709 | −4252 | −4240 | −1538 | −4376 | 4892 | −2923 | −3417 | 1381 | −2343 | −3896 | −4606 | −3607 | −3347 | −4116 | −3942 | −3297 | −2280 | −1292 | 330 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 278(T) | −1794 | −2944 | 99 | −1062 | −3953 | −2361 | −1803 | −3744 | −1729 | −3753 | −2919 | 2222 | −2829 | −1442 | −2305 | 1194 | 2849 | −3137 | −3957 | −3248 | 331 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 279(F) | −4666 | 1469 | −5329 | −5600 | 4144 | −5120 | −1487 | −3637 | −5160 | −3061 | −3095 | −3851 | −5019 | −3971 | −4573 | −4367 | −4562 | −3771 | −742 | 2400 | 332 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 280(E) | −993 | −2363 | −876 | 2071 | −2644 | −1981 | 2018 | −2365 | −241 | −2362 | 390 | −634 | −40 | 1941 | −739 | −894 | 426 | −384 | −2572 | −1915 | 333 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 281(H) | −3635 | −4141 | −2481 | −2626 | −2997 | −3692 | 5257 | −4886 | −2082 | −4514 | −4107 | −2763 | −4095 | 92 | −2165 | −3525 | −3677 | −4578 | −3303 | −2455 | 334 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 282(E) | −310 | −4317 | 520 | 3226 | −4661 | 1262 | −1926 | −4565 | −2136 | −4453 | −3755 | −1193 | −3092 | −1590 | −2961 | −2255 | −2635 | −4020 | −4649 | −3669 | 335 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 283(I) | −3109 | −2594 | −5687 | −5258 | −2040 | −5447 | −4789 | 2687 | −5127 | 2204 | −803 | −5121 | −4973 | −4528 | −4983 | −4783 | −3057 | 1096 | −3762 | −3679 | 336 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |

TABLE 3-continued

| | | | | | | | | | | | | | | | | | | | | | |
|---|---|---|---|---|---|---|---|---|---|---|---|---|---|---|---|---|---|---|---|---|---|
| 284(R) | 1930 | −2801 | −1080 | 241 | −3166 | −2275 | −912 | −2874 | −337 | −2798 | −1919 | 868 | −2397 | 569 | 2445 | −1288 | −1343 | −2456 | −2934 | −2321 | 337 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 285(Q) | −1119 | 867 | −3256 | −2635 | 296 | −2643 | −1503 | −469 | −2274 | −824 | 1432 | −2219 | −2695 | 2042 | −2148 | −1719 | 1528 | 1807 | −1431 | 1003 | 338 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 286(A) | 3647 | −2999 | −4758 | −5092 | −5144 | −3219 | −4514 | −5091 | −5094 | −5303 | −4637 | −3980 | −3954 | −4741 | −4797 | −2812 | −3007 | −4128 | −4931 | −5200 | 339 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 287(R) | −438 | −1218 | −2385 | −1792 | −1208 | −2507 | −1291 | 204 | −277 | 1082 | −410 | −1737 | −2569 | −1360 | 2522 | −410 | −1068 | 702 | −1647 | −1266 | 340 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 288(W) | 180 | −1750 | 1481 | 940 | −1841 | −2159 | −866 | 977 | −643 | −920 | −906 | 114 | −2242 | −565 | −1063 | −1106 | 370 | −499 | 2833 | 79 | 341 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 289(H) | 1869 | −1372 | −1935 | −1371 | 128 | −2386 | 2326 | −951 | −1207 | 263 | −557 | 1380 | −2458 | −1069 | −1489 | −476 | −1037 | −822 | −1723 | 344 | 342 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 290(G) | −2602 | −4486 | 1035 | 201 | −4670 | 3031 | −1891 | −4579 | −363 | −4449 | −3755 | 1477 | −3090 | −1551 | −2902 | −2272 | −2659 | −4058 | −4641 | −3646 | 343 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 291(M) | 251 | −1162 | −3387 | −2773 | −1077 | −2851 | −1716 | 431 | 1723 | 1291 | 2513 | −2402 | −2886 | −2100 | −2325 | −1930 | −1249 | 891 | −1646 | −1308 | 344 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 292(L) | −4115 | −3482 | −6205 | −5777 | 1065 | −5951 | −3943 | −1092 | −5536 | 3135 | −370 | −5542 | −5143 | −4288 | −4987 | −5397 | −3959 | −1932 | −2773 | −2309 | 345 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 293(G) | −2777 | −2893 | −4388 | −4459 | 2368 | 3236 | −2287 | −2772 | −4264 | −1129 | −2377 | −3541 | −4076 | −3729 | −4048 | −3027 | −3020 | −2799 | −1729 | −655 | 346 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 294(H) | −1953 | −2855 | −1413 | −1605 | −3687 | −2513 | 3228 | −4087 | −2128 | −4093 | −3338 | 332 | −3088 | −1980 | −2503 | 3011 | −2205 | −3384 | −3901 | −3137 | 347 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 295(I) | −2891 | −2384 | −5528 | −5155 | −2443 | −5319 | −4964 | 3155 | −5067 | 1192 | −1186 | −4980 | −4973 | −4745 | −5079 | −4666 | −2864 | 1741 | −4142 | −3869 | 348 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 296(D) | −4886 | −4905 | 4186 | −3339 | −5949 | −4221 | −4195 | −6666 | −4787 | −6283 | −6022 | −3676 | −4750 | −4186 | −5191 | −4762 | −5055 | −6188 | −5117 | −5507 | 349 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 297(A) | 3106 | −2388 | −4425 | −4439 | −2714 | −3005 | −3693 | −1978 | −4125 | 1368 | −1762 | −3486 | −3618 | −3799 | −3953 | −2396 | −2377 | −2053 | −3726 | −3485 | 350 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 298(N) | −4313 | −4359 | −3728 | −4093 | −5358 | −4169 | −4424 | −6344 | −4850 | −6082 | −5725 | 4411 | −4732 | −4593 | −4904 | −4442 | −4627 | −5689 | −4872 | −5035 | 351 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 299(Q) | −1050 | −2442 | −224 | −369 | −2747 | 1053 | −681 | −2473 | −248 | −2449 | 544 | −670 | −2117 | 2694 | 1514 | −944 | 498 | −2058 | −2641 | −1985 | 352 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 300(G) | −2973 | −3542 | −2659 | −2952 | −5121 | 3336 | −3467 | −5361 | −3342 | −5272 | −4637 | −3006 | −3958 | 2548 | −3517 | −3070 | −3300 | −4530 | −4778 | −4688 | 353 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |

TABLE 3-continued

| | | | | | | | | | | | | | | | | | | | | | |
|---|---|---|---|---|---|---|---|---|---|---|---|---|---|---|---|---|---|---|---|---|---|
| 301(D) | −1715 | −3268 | 3029 | −581 | −3564 | −2306 | 1979 | −3347 | −946 | −3273 | −2410 | 1223 | −2578 | −803 | 1209 | −403 | −1686 | −2889 | −3440 | −2693 | 354 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 302(M) | −558 | −1400 | −1835 | −1269 | −1420 | 890 | −1097 | −990 | 950 | 207 | 1982 | −1370 | 1756 | −980 | −1393 | −1333 | −1014 | −854 | −1800 | 1377 | 355 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 303(Q) | −1128 | −1286 | −2178 | −1630 | −1284 | −2459 | −1259 | 1117 | −1410 | 1858 | −477 | −456 | −570 | 2119 | −1614 | −710 | −1072 | −723 | −1713 | −1319 | 356 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 304(W) | −204 | 887 | 46 | 246 | −204 | −619 | 891 | −475 | 338 | −941 | 659 | 291 | −334 | 598 | 147 | −143 | 7 | −471 | 1260 | 199 | 357 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 305(L) | −1103 | −1400 | −1916 | −1340 | −1417 | −2382 | −1126 | 637 | 1258 | 1645 | −580 | 975 | −2451 | −1022 | 117 | −1378 | −44 | 68 | −1800 | −1383 | 358 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 306(G) | −4196 | −3631 | −4960 | −5174 | 1957 | 3226 | −1563 | −3645 | −4889 | −3130 | −3107 | −3746 | −4818 | −3883 | −4436 | −4054 | −4213 | −3704 | −843 | 2077 | 359 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 307(W) | −4933 | −4706 | 2215 | −3821 | −3602 | −4386 | −3866 | −6001 | −4863 | −5555 | −5403 | −4024 | −4864 | −4404 | −5022 | −4890 | −5088 | −5755 | 5837 | −3163 | 360 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 308(D) | −3069 | −4812 | 3638 | −1083 | −5072 | −2828 | −2301 | −5194 | −2654 | −5012 | −4468 | −1476 | −3411 | 2464 | −3523 | −2710 | −3180 | −4638 | −5009 | −4074 | 361 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 309(T) | −1461 | −1742 | 1783 | −1718 | −1846 | −2672 | −1664 | 872 | −1706 | −1478 | 697 | −1809 | −2839 | −1548 | −2007 | −1775 | 2886 | −761 | −2357 | −1930 | 362 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 310(D) | −3546 | −4222 | 3684 | −2153 | −3783 | −3505 | −3081 | −3676 | −3519 | 1330 | −3277 | −2487 | −4027 | −2939 | −4117 | −3445 | −3684 | −3809 | −4315 | −3781 | 363 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 311(E) | −1512 | −2828 | −1244 | 2417 | −3192 | −2375 | −959 | −2865 | −303 | −2800 | −1945 | −1024 | −2482 | 2385 | 1159 | −1395 | −1429 | 514 | −2934 | −2364 | 364 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 312(F) | −4608 | −3778 | −5235 | −5513 | 4303 | −5053 | −1486 | −3725 | −5109 | −3128 | −3164 | −3822 | −4992 | −3954 | −4550 | −914 | −4537 | −3840 | −745 | 1588 | 365 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −61 | −8312 | −4703 | −894 | −1115 | −701 | −1378 | * | * | | | | | | | | | | | | |
| 313(P) | −1888 | −2446 | −3444 | −3643 | −4185 | 1827 | −3530 | −4064 | −3734 | −780 | −3561 | −3019 | 3618 | −3530 | −3731 | −2122 | −2300 | −3299 | −4374 | −4144 | 366 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8258 | −9300 | −894 | −1115 | −545 | −1668 | * | * | | | | | | | | | | | | |
| 314(T) | −273 | −2001 | −1163 | −623 | −2217 | −2089 | 1932 | 12 | −526 | −2008 | −1201 | 1155 | −1093 | −465 | −983 | 551 | 2418 | −1582 | −2356 | −1797 | 367 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 315(D) | −1847 | −3447 | 2925 | 425 | −3721 | 1133 | −1341 | −3520 | −1177 | −1150 | −2603 | 1047 | −2659 | −937 | −1790 | 212 | −1833 | −3055 | −3636 | −2845 | 368 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 316(V) | −1151 | −1254 | 1271 | −1753 | −1247 | −2524 | −1330 | 1068 | −1572 | 1200 | −440 | 684 | −2591 | −99 | −1758 | −1555 | −1093 | 1616 | −1703 | −1314 | 369 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 317(Y) | −1131 | −1223 | −2356 | 151 | −1178 | −2505 | −1285 | 128 | −1515 | 1083 | −410 | −1730 | −2569 | −1365 | −371 | −327 | −1070 | −653 | −1626 | 3372 | 370 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |

TABLE 3-continued

| | | | | | | | | | | | | | | | | | | | | | |
|---|---|---|---|---|---|---|---|---|---|---|---|---|---|---|---|---|---|---|---|---|---|
| 318(E) | −66 | −2443 | 1230 | 1971 | −2759 | −1957 | −616 | −2506 | 514 | −1253 | 320 | −594 | −2050 | −158 | 115 | 620 | 475 | −2062 | −2629 | −1949 | 371 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 319(T) | 1585 | −1443 | −1997 | −1450 | −1562 | −2339 | −1262 | −37 | −1291 | −222 | −725 | 1400 | −2485 | −1158 | −1581 | −369 | 2133 | −963 | −1947 | −1528 | 372 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 320(T) | 1918 | −1866 | −4124 | −4033 | −3557 | −2298 | −3314 | −2998 | −3763 | −3472 | −2711 | −2860 | −3018 | −3397 | −3649 | −371 | 3024 | 789 | −3927 | −3691 | 373 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 321(F) | −55 | −1078 | −2947 | −2361 | 2116 | −724 | −1483 | −590 | −2061 | 2010 | −278 | −2084 | −2676 | 498 | −2047 | −1671 | −171 | −506 | −1537 | −1178 | 374 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 322(A) | 2342 | −969 | −3431 | −2800 | 739 | −2681 | −1551 | 746 | −2407 | −373 | −168 | −2310 | −2731 | −2040 | −2226 | −639 | −1077 | 1060 | 1858 | −1084 | 375 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 323(M) | −2508 | −2232 | −4761 | −4150 | −1237 | −4143 | −2920 | −798 | −3746 | 1337 | 4541 | −3775 | −3961 | −3190 | −3504 | −3281 | −381 | −1230 | 1231 | −2166 | 376 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 324(Y) | −1183 | −1021 | −3411 | −2790 | −854 | −2712 | 739 | −517 | −2406 | −192 | 1479 | −2312 | −2761 | −2042 | −2240 | −406 | −1123 | 1661 | 1953 | 3240 | 377 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 325(E) | −1745 | −3328 | 1991 | 2779 | −3608 | −2301 | −1256 | −3398 | −1050 | −3330 | −2469 | −915 | −2592 | 1001 | −1642 | −220 | −1723 | −626 | −3510 | −2737 | 378 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 326(I) | −2844 | −2383 | −5395 | −4937 | 151 | −5038 | −4287 | 2475 | −4753 | 1393 | −861 | −4697 | −4716 | −4269 | −4629 | −4304 | −2798 | 2345 | −3556 | −3362 | 379 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 327(L) | −3363 | −2830 | −5881 | −5398 | −1770 | −5628 | −4722 | 1688 | −5234 | 2786 | −540 | −5318 | −5008 | −4398 | −4954 | −4964 | −3282 | 734 | −3526 | −3572 | 380 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 328(K) | −365 | −2488 | 41 | 1718 | −2813 | −1989 | −641 | −2559 | 2204 | −1130 | −1578 | −624 | −2083 | 814 | 944 | −903 | −960 | −2112 | −2664 | −1989 | 381 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 329(N) | 716 | −2390 | −858 | 192 | −377 | −873 | 712 | −2414 | −222 | −2394 | 336 | 2657 | −2061 | 626 | −263 | 421 | −924 | −1997 | −2590 | −1924 | 382 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 330(G) | 66 | −2442 | 172 | −2179 | −4601 | 3363 | −2899 | −4434 | −3223 | −4571 | −3714 | −2119 | −3077 | −2685 | −3642 | −14 | −2069 | −3384 | −4750 | −4279 | 383 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −244 | −8312 | −2711 | −894 | −1115 | −701 | −1378 | * | * | | | | | | | | | | | | |
| 331(G) | −1329 | −1980 | −1953 | −1910 | 214 | 3238 | −2065 | −2824 | −2078 | −3015 | −2271 | −1831 | −2735 | 197 | −2364 | 190 | −1589 | −2329 | −3112 | −2499 | 384 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8076 | −9118 | −894 | −1115 | −1192 | −831 | * | * | | | | | | | | | | | | |
| 332(F) | −2519 | −2199 | −4819 | −4218 | 2372 | −4220 | −2969 | 1473 | −3877 | 2085 | −110 | −3854 | 1128 | −3227 | −3601 | −3367 | −2431 | −1024 | −2364 | −2136 | 385 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −1585 | −8137 | −593 | −894 | −1115 | −1458 | −653 | * | * | | | | | | | | | | | | |
| 333(D) | −901 | −2417 | 2169 | 499 | −2834 | 1682 | −424 | −2665 | −438 | −2621 | −1844 | 1572 | −1628 | −64 | −1115 | −688 | −954 | −2173 | −2820 | −1986 | 386 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −555 | −6574 | −1696 | −894 | −1115 | −3087 | −181 | * | * | | | | | | | | | | | | |
| 334(G) | −771 | −1114 | −1327 | −1503 | −2474 | 3336 | −1576 | −2519 | −1737 | −2659 | −2097 | −1339 | −1786 | −1606 | −1805 | −971 | −1107 | −1936 | −2209 | −2293 | 387 |
| — | −148 | −500 | 233 | 43 | −381 | 399 | 106 | −626 | 210 | −466 | −720 | 275 | 394 | 45 | 96 | 359 | 118 | −369 | −294 | −249 | |
| — | −1217 | −830 | −7094 | −156 | −3286 | −3231 | −162 | * | * | | | | | | | | | | | | |

TABLE 3-continued

| | | | | | | | | | | | | | | | | | | | | | |
|---|---|---|---|---|---|---|---|---|---|---|---|---|---|---|---|---|---|---|---|---|---|
| 335(P) | −947 | −1231 | −1366 | −1466 | −2201 | −1324 | −1470 | −2177 | −1504 | −2284 | −1843 | −1373 | 3767 | −1487 | −1585 | −1143 | −1229 | −1796 | −2061 | −2037 | 389 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −33 | −6052 | −7094 | −894 | −1115 | −2145 | −370 | * | * | | | | | | | | | | | | |
| 336(G) | 1354 | −1173 | −535 | −238 | −2069 | 1779 | −486 | −1725 | 1105 | −1853 | −1038 | −370 | −1543 | −134 | −464 | −352 | −421 | −1271 | −2125 | −1610 | 390 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −21 | −6683 | −7725 | −894 | −1115 | −113 | −3725 | * | * | | | | | | | | | | | | |
| 337(Y) | 923 | −2098 | −152 | −490 | −2292 | 773 | −737 | −1954 | 123 | −2065 | −1235 | −765 | 927 | −341 | −870 | −977 | 771 | −667 | −2379 | 2237 | 391 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 338(T) | −596 | −2454 | −27 | 443 | −2775 | −1955 | 675 | −2525 | 1003 | −2470 | −1543 | 140 | 1222 | 782 | 953 | −43 | 1528 | −2076 | −2637 | −1955 | 392 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 339(G) | −4740 | −4445 | −5364 | −5738 | −6131 | 3840 | −5265 | −6903 | −6030 | −6539 | −6235 | −5426 | −5034 | −5814 | −5624 | −5041 | −5115 | −6153 | −5123 | −6096 | 393 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 340(G) | −2931 | −3331 | −4304 | −4658 | −5520 | 3378 | −4536 | −5732 | −5076 | −5740 | −5043 | −4039 | 2291 | −4709 | −4901 | −3171 | −3373 | −4635 | −5035 | −5498 | 394 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 341(L) | −1644 | −1468 | −3782 | −3157 | 438 | −3201 | −2041 | 710 | −2752 | 2206 | −223 | −2773 | −3187 | −2399 | 1799 | −2291 | 253 | −697 | −1864 | −1566 | 395 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 342(N) | −3133 | −4000 | −1625 | −1938 | −3244 | −3217 | 3075 | −4941 | −2575 | −4694 | −4212 | 3945 | −3753 | −2478 | −2897 | −2996 | −3298 | −4437 | −3600 | −2686 | 396 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 343(F) | −5308 | −4420 | −5610 | −5948 | 4547 | −4921 | −3048 | −4656 | −5852 | −3992 | −4112 | −4995 | −5217 | −5110 | −5315 | −5363 | −5399 | −4866 | −2341 | −1279 | 397 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 344(D) | −3598 | −4594 | 4015 | −1825 | −3014 | −3354 | −2628 | −5167 | −3365 | −4864 | −4554 | −2168 | −3906 | −2692 | −4098 | −3307 | −3726 | −4804 | −3495 | 737 | 398 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 345(A) | 3015 | −2000 | −3678 | −3337 | 863 | −3026 | −1786 | −1924 | −3083 | −2118 | −1567 | −2743 | −3353 | −2703 | −3034 | −485 | −2005 | −1776 | −1454 | 1913 | 399 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 346(K) | −3437 | −3998 | −3427 | −2630 | −4447 | −3747 | 1328 | −4350 | 3785 | −3966 | −3350 | −2554 | −3806 | −1483 | −516 | −3312 | −3161 | −4115 | −3603 | −3389 | 400 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 347(V) | 467 | −1371 | −3451 | −2935 | −1595 | −2710 | −2060 | −662 | −2633 | −346 | −783 | −2500 | 2276 | −2347 | −2594 | −1872 | 715 | 2313 | −2129 | −1779 | 401 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 348(R) | −1896 | −2633 | −2566 | −1895 | −3409 | −2759 | −1580 | −3013 | −629 | −715 | −2292 | −1894 | 174 | −1218 | 3522 | 651 | −1925 | −2662 | −3190 | −2839 | 402 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 349(R) | −5156 | −4675 | −5377 | −4998 | −5777 | −4641 | −4103 | −6271 | −3143 | −5805 | −5439 | −4840 | −4993 | −4014 | 4230 | −5318 | −5151 | −5964 | −4773 | −5292 | 403 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 350(T) | 361 | −2459 | −832 | 770 | −2780 | −972 | −644 | −2526 | −232 | −2480 | −1560 | 624 | −666 | 1428 | −740 | 39 | 2295 | −2083 | −2655 | −1976 | 404 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 351(S) | −2650 | −4418 | 471 | 1677 | −4792 | −2597 | −2009 | −4725 | −2280 | −4605 | −3943 | −1231 | −3150 | −1685 | −3140 | 3091 | −2749 | −4162 | −4795 | −3785 | 405 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −383 | −8312 | −2119 | −894 | −1115 | −701 | −1378 | * | * | | | | | | | | | | | | |

TABLE 3-continued

| | | | | | | | | | | | | | | | | | | | | | |
|---|---|---|---|---|---|---|---|---|---|---|---|---|---|---|---|---|---|---|---|---|---|
| 352(F) | −1686 | −1643 | −3313 | −2900 | 3471 | −2934 | −1275 | −1319 | −2616 | −1518 | −978 | −2397 | −3095 | −2241 | −2563 | −216 | 1898 | −1228 | −906 | 1070 | 406 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −9 | −7937 | −8980 | −894 | −1115 | −254 | −2629 | * | * | | | | | | | | | | | | |
| 353(D) | 395 | −2586 | 2498 | 794 | −2902 | −678 | −718 | −2657 | 1205 | −2600 | −1681 | −648 | −2139 | 585 | −841 | −973 | 248 | −2206 | −2769 | −2076 | 407 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 354(W) | −204 | 887 | 46 | 246 | −204 | −619 | 891 | −475 | 338 | −941 | 659 | 291 | −334 | 598 | 147 | −143 | 7 | −471 | 1260 | 199 | 408 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 355(P) | 574 | −1802 | 174 | 209 | 242 | −2139 | −841 | −414 | 215 | −426 | 693 | −939 | 1418 | 345 | −227 | −1082 | −961 | 254 | −2132 | 883 | 409 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 356(E) | −1666 | −3205 | 2244 | 2653 | −3457 | −2276 | −1194 | −3250 | −962 | −3199 | −2337 | −894 | −2544 | 492 | −1537 | −1489 | −1638 | −1099 | −3379 | 987 | 410 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 357(D) | −3359 | −4413 | 3698 | −1801 | −5459 | 1768 | −2962 | −5658 | −3441 | −5486 | −4961 | −2153 | −3821 | −2730 | −4255 | −3154 | −3567 | −4971 | −5125 | −4670 | 411 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 358(L) | −3209 | −2692 | −5753 | −5295 | −1892 | −5491 | −4700 | 887 | −5141 | 2651 | −663 | −5173 | −4965 | −4433 | −4931 | −4819 | −3144 | 1908 | −3615 | −3591 | 412 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 359(W) | −3018 | −2633 | −4761 | −4491 | 3489 | −4266 | −1661 | 1631 | −4078 | −1724 | −1536 | −3487 | −1838 | −3365 | −3744 | −3422 | −2946 | −2006 | 4055 | 56 | 413 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 360(Y) | 828 | −1415 | −340 | −305 | −1437 | −2319 | 1172 | 1116 | −1057 | 992 | −593 | −1325 | −2393 | −936 | −276 | −1304 | −999 | −869 | −1810 | 2176 | 414 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 361(A) | 2490 | −1883 | −3530 | −3268 | 392 | 1317 | −2915 | −3137 | −3094 | −3410 | −2609 | −2570 | −2929 | −2839 | −3197 | 1570 | −155 | −2497 | −3780 | −3478 | 415 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 362(H) | 1671 | −2732 | −3104 | −3318 | −3618 | −2860 | 4890 | −4439 | −3288 | −4509 | −3848 | −2949 | −3546 | −3299 | −3341 | −2352 | −2548 | −3629 | −3930 | −3278 | 416 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 363(I) | 372 | −1510 | −2804 | −2153 | −1581 | −2814 | −1570 | 3136 | 406 | −1345 | −734 | −2057 | −2878 | −1575 | 172 | −1891 | −1390 | 26 | −2021 | −1655 | 417 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 364(A) | 2824 | −1953 | −4254 | −4336 | −4278 | 1795 | −3663 | −3992 | −4116 | −4288 | −3398 | −2940 | −3040 | −3690 | −3947 | 484 | −1804 | −87 | −4541 | −4398 | 418 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 365(G) | 440 | 2735 | −4017 | −4164 | −4414 | 3094 | −3664 | −4182 | −4084 | −4444 | −3530 | 1340 | −3050 | −3662 | −3947 | −1624 | −1829 | −3066 | −4648 | −4508 | 419 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 366(M) | −3435 | −3070 | −5645 | −5292 | −1686 | −5048 | −4285 | 177 | −4844 | −362 | 5058 | −5009 | −4816 | −4199 | −4559 | −4488 | −3429 | −1290 | −3293 | −3151 | 420 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 367(D) | −2500 | −3942 | 3572 | −1015 | −4586 | −2633 | −1974 | −4469 | −1888 | −4357 | −3653 | −1359 | −3145 | −1638 | 1771 | −503 | −2599 | −3914 | −4464 | −3654 | 421 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 368(T) | 1100 | −1830 | −2203 | −1732 | −2569 | −2230 | −1735 | −2187 | −1612 | −2425 | 2062 | 435 | −2620 | −1496 | −1953 | 1109 | 2598 | −1840 | −2841 | −2399 | 422 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |

TABLE 3-continued

| | | | | | | | | | | | | | | | | | | | | | |
|---|---|---|---|---|---|---|---|---|---|---|---|---|---|---|---|---|---|---|---|---|---|
| 369(Y) | −4358 | −3577 | −5299 | −5430 | 3019 | −5078 | −1573 | −2961 | −5006 | −1623 | 2952 | −3869 | −4923 | −3893 | −4468 | −4298 | −4237 | −3252 | −830 | 3643 | 423 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 370(A) | 3106 | −2388 | −4425 | −4439 | −2714 | −3005 | −3693 | −1978 | −4125 | 1368 | −1762 | −3486 | −3618 | −3799 | −3953 | −2396 | −2377 | −2053 | −3726 | −3485 | 424 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 371(R) | 722 | −1126 | −2900 | −2287 | −1095 | −2649 | −1470 | 1035 | −567 | 1406 | −311 | −2061 | −2701 | −1716 | 1956 | −1708 | −1121 | 435 | −1583 | −1225 | 425 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 372(G) | 1248 | −1889 | −3801 | −3776 | −3523 | 2775 | −3223 | −3143 | −3626 | 1237 | −2695 | −2780 | −3011 | −3284 | −3555 | −677 | −1747 | −2517 | −3884 | −3627 | 426 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 373(L) | −2143 | −2281 | −3312 | −2427 | 697 | −3298 | −1645 | −1581 | 1855 | 2371 | −1066 | −2323 | −3278 | −1496 | 360 | −2446 | −2014 | −1662 | −2346 | −1935 | 427 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 374(K) | −1243 | −2663 | −484 | 1864 | −3023 | −2175 | −770 | −2741 | 2247 | −1301 | −1757 | −811 | −2263 | 491 | 1587 | −1121 | −1167 | −2309 | −2789 | −2166 | 428 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 375(V) | 135 | −1595 | −1634 | −1081 | −1703 | −685 | −1060 | −548 | −931 | −1546 | −820 | 692 | −2371 | −843 | 1741 | −469 | −1038 | 2254 | −2023 | −1565 | 429 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 376(A) | 3481 | −2081 | −4434 | −4657 | −4120 | −2450 | −3905 | −2895 | −4402 | −3809 | −3256 | −3167 | −3225 | −3995 | −4150 | −1826 | −1986 | −149 | −4587 | −4404 | 430 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 377(A) | 1962 | −2221 | −948 | 716 | −2449 | −2010 | 1143 | −2137 | 247 | −1046 | −1336 | 675 | −2101 | −258 | −794 | −334 | −934 | −427 | −2463 | 1197 | 431 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 378(K) | 2235 | −3511 | −3265 | −2182 | −4396 | −3362 | −1483 | −3787 | 2511 | −3506 | −2802 | −2133 | −3385 | −1064 | 1852 | −2645 | −2521 | −3495 | −3399 | −3235 | 432 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 379(M) | −3847 | −3277 | −6201 | −5593 | 2394 | −5898 | −4497 | 240 | −5358 | 2214 | 3316 | −5599 | −5021 | −4167 | −4850 | −5211 | −3688 | −1727 | −3154 | −3303 | 433 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 380(I) | −1275 | −1329 | −2647 | −1990 | −1321 | −2643 | 565 | 2209 | 625 | 584 | −515 | −1883 | −2692 | −1414 | 1794 | −1698 | −1203 | 413 | −1741 | −1377 | 434 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 381(E) | 944 | −2571 | 656 | 2380 | −2887 | −2009 | −705 | −2642 | 620 | −2585 | −1665 | 137 | −2128 | 844 | −823 | −959 | −41 | −2191 | −2754 | −2062 | 435 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 382(D) | −598 | −4837 | 3833 | 578 | −5072 | −2648 | −2116 | −5055 | −2532 | −4904 | −4335 | −1252 | −3241 | −1811 | −3527 | −2501 | −2990 | −4481 | −5103 | −3988 | 436 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 383(P) | −1003 | −2474 | −144 | −294 | −2795 | 1002 | −631 | −2545 | 989 | −2490 | −1565 | 774 | 1615 | 611 | 937 | 553 | −942 | −2097 | −2657 | −1975 | 437 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 384(F) | 81 | −1956 | −1130 | 1500 | 1552 | −2090 | −781 | −1736 | 41 | −1894 | −1096 | −841 | 683 | 68 | −936 | −136 | −956 | 1365 | −2258 | −1704 | 438 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 385(F) | −2039 | −1782 | −4382 | −3777 | 2108 | −3679 | −2463 | 807 | −3406 | 1823 | −321 | −3311 | −3599 | −2912 | −3176 | −2794 | −1969 | 1752 | −2089 | 943 | 439 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |

TABLE 3-continued

| | | | | | | | | | | | | | | | | | | | | | |
|---|---|---|---|---|---|---|---|---|---|---|---|---|---|---|---|---|---|---|---|---|---|
| 386(D) | −987 | 436 | 2031 | 1591 | −2780 | −1958 | −618 | −2531 | 514 | −2475 | −1549 | 86 | −2053 | 1563 | 61 | −143 | −197 | −2081 | −2643 | −1960 | 440 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 387(E) | −507 | −2601 | 840 | 1955 | −2917 | −2021 | −726 | −2673 | 1456 | −2615 | −1696 | 1166 | −2147 | 1657 | −852 | −409 | −1056 | −2221 | −2783 | −2088 | 441 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 388(M) | 1019 | −961 | −3469 | −2834 | 1400 | −2682 | −1552 | 1329 | −2431 | 1012 | 1489 | −2324 | −2730 | −2055 | −255 | −1766 | −1074 | 894 | 1470 | −1077 | 442 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 389(M) | −1149 | −1013 | −3253 | −2628 | −962 | −2671 | −1525 | 2021 | −134 | 1151 | 2066 | −2232 | −2720 | −223 | −304 | −1746 | −1089 | 1184 | −1468 | −1122 | 443 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 390(A) | 1814 | −2486 | 567 | 1223 | −2807 | −1975 | −640 | −2557 | 1226 | −2501 | −1576 | −610 | −2073 | 413 | 729 | −291 | −953 | −2108 | −2667 | −1985 | 444 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 391(E) | 1007 | −2465 | 333 | 2274 | −2786 | −1961 | 536 | −2537 | 738 | −2481 | −1555 | 281 | −2057 | 320 | −172 | −872 | −68 | −2087 | −2649 | −1965 | 445 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 392(R) | 73 | −2800 | −1762 | −1095 | −3205 | −2591 | −1056 | −2829 | 795 | −2778 | −1964 | −1292 | −2658 | −633 | 3242 | 417 | −1588 | −2495 | −2901 | 541 | 446 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 393(Y) | −2721 | −3376 | −2973 | −2154 | −3188 | −727 | −1495 | −3439 | 891 | −3279 | −2619 | −2128 | −3405 | −1166 | 820 | −2667 | −2523 | −3217 | −2977 | 4298 | 447 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 394(A) | 1285 | −2377 | −872 | 585 | −2664 | −1977 | −638 | −2390 | 605 | −788 | −1475 | −626 | −2069 | 1284 | 427 | 1071 | −929 | 395 | −2580 | −1920 | 448 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 395(S) | 131 | −2423 | 336 | 386 | −341 | −50 | −762 | −2464 | −386 | −2470 | −1581 | −713 | −2161 | −325 | −890 | 2478 | −324 | −2059 | −2688 | −2031 | 449 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 396(F) | −3512 | −3303 | 10 | 1365 | 3217 | −4329 | −1411 | −3102 | −3530 | −2820 | −2586 | −3109 | −4323 | −3009 | −3565 | −3461 | −3428 | −3094 | 3031 | 2760 | 450 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 397(D) | −990 | −2441 | 1836 | −293 | −2754 | −1964 | −625 | −2498 | 1161 | 389 | −1533 | 1125 | −131 | −168 | 2 | −164 | 557 | −2059 | −2630 | −1953 | 451 |
| — | −147 | −500 | 233 | 43 | −381 | 399 | 105 | −627 | 211 | −466 | −721 | 276 | 393 | 45 | 96 | 359 | 117 | −370 | −295 | −250 | |
| — | −466 | −1865 | −9354 | −73 | −4335 | −701 | −1378 | * | * | | | | | | | | | | | | |
| 398(E) | −84 | −2457 | −258 | 1626 | −2777 | −455 | −617 | −2527 | 254 | −2472 | −1546 | −593 | −2051 | 799 | 115 | 1531 | 906 | −2078 | −2640 | −1958 | 453 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 399(G) | −1414 | −2476 | −1090 | 1358 | −2997 | 2543 | −1296 | −2678 | −1035 | −762 | −1957 | −1125 | 1149 | −921 | −1515 | −1387 | −149 | −2292 | −3069 | −2463 | 454 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 400(I) | 128 | −1033 | −3266 | −2651 | −1007 | −2701 | −1569 | 2545 | −778 | 400 | −239 | −2262 | −914 | −1978 | −2197 | −1777 | 1346 | 618 | −1515 | −1165 | 455 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 401(G) | 129 | −2062 | −3816 | −3956 | −3724 | 3250 | −3484 | −3244 | −3864 | 847 | −2909 | −2938 | −3156 | −3542 | −3752 | −1788 | −1933 | −2674 | −4165 | −3918 | 456 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −79 | −8312 | −4317 | −894 | −1115 | −701 | −1378 | * | * | | | | | | | | | | | | |
| 402(Q) | 1462 | −2384 | −811 | 38 | −2692 | −1184 | −584 | −2431 | 1433 | −354 | 117 | 801 | −2020 | 1472 | 466 | −836 | −887 | −1999 | −2574 | −1903 | 457 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8240 | −9282 | −894 | −1115 | −509 | −1750 | * | * | | | | | | | | | | | | |

TABLE 3-continued

| | | | | | | | | | | | | | | | | | | | | | |
|---|---|---|---|---|---|---|---|---|---|---|---|---|---|---|---|---|---|---|---|---|---|
| 403(D) | 286 | −2477 | 2128 | 1000 | −2797 | −1001 | −633 | −2548 | 308 | −2493 | −1568 | −601 | 199 | 1422 | −727 | 187 | −166 | −2099 | −2661 | −1976 | 458 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 404(W) | −204 | 887 | 46 | 246 | −204 | −619 | 891 | −475 | 338 | −941 | 659 | 291 | −334 | 598 | 147 | −143 | 7 | −471 | 1260 | 199 | 459 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 405(I) | −1225 | −1056 | −3499 | −2876 | 1632 | 939 | −1661 | 2615 | −2494 | −822 | 1196 | −2403 | −126 | −2131 | −2324 | −1865 | −1168 | 223 | −1539 | −1195 | 460 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −183 | −8312 | −3109 | −894 | −1115 | −701 | −1378 | * | * | | | | | | | | | | | | |
| 406(E) | −156 | −1264 | −2093 | 2168 | −1299 | −2445 | −1234 | 765 | −347 | 105 | −458 | −1568 | −2508 | −1200 | −1588 | −1457 | −1033 | 1607 | −1750 | −1344 | 461 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8137 | −9179 | −894 | −1115 | −1458 | −653 | * | * | | | | | | | | | | | | |
| 407(E) | 360 | −2380 | 448 | 1932 | −2699 | −673 | −533 | −2451 | 240 | −2395 | −1470 | 1122 | −1965 | 522 | −630 | 837 | −34 | −2001 | −2563 | −1878 | 462 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8137 | −9179 | −894 | −1115 | −373 | −2136 | * | * | | | | | | | | | | | | |
| 408(G) | −306 | −1754 | −2167 | −1874 | −1807 | 2904 | −1682 | −1676 | −1831 | −397 | −1274 | −3 | −2773 | −1677 | −2075 | −1633 | −1459 | −1477 | −2248 | 1794 | 463 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 409(K) | 356 | −2456 | −833 | 230 | −2777 | −1959 | 716 | −2527 | 2040 | −2472 | −1546 | 519 | −2052 | 1143 | 415 | 499 | 717 | −2078 | −2639 | −1958 | 464 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 410(A) | 1615 | −2218 | 495 | 834 | −2445 | −2009 | 454 | −2132 | −307 | −625 | 696 | −690 | −2100 | −258 | −151 | −93 | 780 | −5 | −2460 | −1840 | 465 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 411(D) | −1190 | −2605 | 1765 | 410 | −2890 | −2073 | −813 | −2627 | −455 | 475 | −1718 | 532 | −2218 | −375 | −974 | 1045 | 1564 | −2211 | −2813 | −2132 | 466 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 412(F) | −2934 | −2588 | −5133 | −4524 | 2606 | −4635 | −3270 | −872 | −262 | 2523 | 1205 | −4222 | −4303 | −3468 | −3837 | −3796 | −2830 | −1448 | −2581 | −2349 | 467 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 413(E) | 1449 | −2456 | −323 | 1515 | −2776 | −1957 | 1150 | −2526 | 1493 | −2471 | −1545 | 270 | −1061 | −157 | −422 | −422 | 54 | −2077 | −2639 | −1957 | 468 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 414(D) | −185 | −2555 | 2037 | 1092 | −2872 | −2002 | −694 | −2626 | 851 | −2570 | −1649 | −635 | −2118 | 444 | −809 | 1514 | −290 | −2176 | −2739 | −2048 | 469 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 415(L) | −76 | −1139 | −2558 | −1967 | −1115 | −2532 | −1344 | −133 | −1691 | 2129 | −330 | −1845 | −2594 | 221 | 1015 | −484 | −1055 | 439 | −1577 | −1205 | 470 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 416(E) | 1511 | 1129 | −1595 | 1751 | −1576 | −2259 | −999 | −1157 | −900 | −416 | −704 | −1196 | −2339 | −797 | −1260 | 687 | −49 | −278 | −1911 | 36 | 471 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 417(K) | 1530 | −2471 | −17 | 1044 | −2791 | −1963 | −628 | −2542 | 1572 | −2487 | −1561 | 676 | −2060 | 1100 | −720 | −173 | −45 | −2093 | −2654 | −1971 | 472 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 418(Y) | −3642 | −3323 | −4353 | −3980 | 2403 | −4454 | 1728 | −3120 | −855 | −2839 | −2606 | −3260 | −4404 | −2976 | 133 | −3614 | −3524 | −3122 | −870 | 4083 | 473 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 419(A) | 2435 | −1847 | −629 | 808 | −1986 | −901 | −1033 | 1094 | −847 | −1803 | −1059 | −1095 | −2363 | −746 | −1268 | −1239 | −1109 | −542 | −2252 | −1747 | 474 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |

TABLE 3-continued

| | | | | | | | | | | | | | | | | | | | | | |
|---|---|---|---|---|---|---|---|---|---|---|---|---|---|---|---|---|---|---|---|---|---|
| 420(E) | 67 | −2239 | 224 | 1346 | −452 | −709 | −673 | 230 | 575 | 996 | −1351 | −680 | −2095 | 263 | −785 | −91 | −453 | −1814 | −2476 | −1850 | 475 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 421(D) | −160 | −2437 | 1202 | 1064 | 1123 | −1958 | −618 | −2495 | 267 | −897 | −1528 | 1077 | −2052 | 1118 | −708 | 595 | −921 | −2054 | −2625 | −70 | 476 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 422(H) | −986 | −2410 | 1343 | −303 | −2711 | −1966 | 2413 | −86 | 1142 | −644 | −1505 | 1346 | 594 | −174 | −432 | −876 | −284 | −2021 | −2605 | −1935 | 477 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −72 | −8312 | −4460 | −894 | −1115 | −701 | −1378 | * | * | | | | | | | | | | | | |
| 423(N) | 209 | −2403 | −80 | 227 | −2718 | 589 | 404 | −2465 | 586 | −861 | 708 | 808 | 710 | 802 | −666 | 242 | −2 | −673 | −2589 | −1910 | 478 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −110 | −8247 | −3828 | −894 | −1115 | −1040 | −961 | * | * | | | | | | | | | | | | |
| 424(Q) | −887 | −2330 | 1492 | 1492 | −2638 | −585 | 686 | −431 | −111 | −450 | −1423 | −504 | −1958 | 1578 | −617 | −233 | 439 | −1945 | −2521 | −1846 | 479 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −848 | −8144 | −1181 | −894 | −1115 | −1434 | −667 | * | * | | | | | | | | | | | | |
| 425(A) | 2076 | −2279 | 957 | 892 | −2676 | −1567 | −534 | −2428 | −295 | −2418 | −1560 | −263 | −1843 | −126 | −852 | 1085 | −887 | −1985 | −2630 | −1917 | 480 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −942 | −7310 | −1080 | −894 | −1115 | −2709 | −239 | * | * | | | | | | | | | | | | |
| 426(E) | −381 | −1604 | 25 | 1852 | −1759 | −1234 | 69 | −1535 | 1212 | −1562 | −736 | 96 | −1382 | 470 | 131 | −287 | −318 | −1195 | −1742 | 1116 | 481 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −246 | −6394 | −2788 | −894 | −1115 | −3145 | −173 | * | * | | | | | | | | | | | | |
| 427(L) | −1340 | −1019 | −3303 | −2788 | −110 | −3122 | −2028 | 1936 | −2461 | 2161 | 988 | −2637 | −2874 | −2038 | −2380 | −2319 | −1277 | 781 | −1493 | −1288 | 482 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −30 | −6178 | −7220 | −894 | −1115 | −1475 | −643 | * | * | | | | | | | | | | | | |
| 428(A) | 996 | −971 | −924 | 841 | −1028 | −1637 | −368 | 796 | −239 | −251 | −142 | 675 | −1717 | −142 | −613 | −33 | −383 | 557 | −1348 | −882 | 483 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −15 | −7202 | −8244 | −894 | −1115 | −137 | −3462 | * | * | | | | | | | | | | | | |
| 429(I) | 1151 | −1159 | −2438 | −631 | 77 | −2505 | −1313 | 1901 | −92 | −1018 | −354 | −1776 | 1747 | −1430 | −1772 | −1536 | −1043 | 561 | −1598 | −1219 | 484 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 430(Q) | 1025 | −2430 | −838 | 1164 | −2741 | −144 | −619 | −1061 | 878 | −2442 | −1522 | 203 | −2052 | 1476 | 325 | −866 | −41 | −346 | −2620 | 236 | 485 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 431(N) | 351 | −2447 | 158 | 275 | −2764 | −782 | 1793 | −2512 | −198 | −80 | −1537 | 1907 | −2050 | 1346 | −99 | −864 | 569 | −2067 | −2632 | −1952 | 486 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 432(K) | −983 | −2449 | 67 | 142 | −2768 | −1958 | 1110 | −2516 | 1671 | −360 | −1539 | −594 | −622 | 1599 | 1436 | −865 | 334 | −883 | −2634 | −1953 | 487 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 433(S) | −1458 | −2150 | −2472 | −2476 | −3880 | 1432 | −2696 | −3646 | −2704 | −880 | −3001 | 42 | −2954 | −2482 | −2971 | 3040 | −1805 | −2869 | −4076 | −3665 | 488 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 434(G) | −1089 | 904 | 851 | −1707 | 768 | 2205 | −1253 | −740 | −1503 | −279 | 1286 | −92 | −2527 | −1318 | −1686 | −1483 | −1029 | −632 | −1617 | 645 | 489 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 435(H) | 818 | −2554 | −999 | −433 | −2894 | −123 | 2729 | −2621 | 956 | −2556 | −1648 | −726 | −235 | 755 | 1964 | −1012 | −1059 | −2189 | −2708 | −2066 | 490 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 436(Q) | −344 | −1587 | −3692 | −3091 | 1883 | −3276 | −2091 | 243 | −2760 | 1475 | −247 | −2787 | −3253 | 2905 | −2674 | −2360 | −1672 | −801 | −1929 | −1608 | 491 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |

TABLE 3-continued

| | | | | | | | | | | | | | | | | | | | | |
|---|---|---|---|---|---|---|---|---|---|---|---|---|---|---|---|---|---|---|---|---|
| 437(E) | −2248 | −2420 | −2316 | 3407 | −2671 | −3394 | −2628 | 379 | −2488 | −1817 | −1617 | −2456 | −3632 | −2387 | −2824 | −2708 | −2279 | 738 | −3560 | −3048 | 492 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 438(R) | 204 | −2356 | −880 | 414 | −2634 | −1980 | 1194 | −2355 | 610 | 446 | −1456 | −633 | −2072 | 1010 | 1766 | −263 | −928 | −735 | −2564 | 773 | 493 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 439(L) | −358 | −1562 | −4144 | −3535 | −1264 | −3440 | −2330 | 1655 | −3166 | 2331 | −351 | −3080 | −3407 | −2740 | −2969 | −2549 | −1736 | 200 | −2069 | 1544 | 494 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 440(K) | −1751 | −3345 | 1209 | 2128 | −3630 | −2309 | −1249 | −3421 | 2410 | −3341 | −2478 | 882 | −2595 | 337 | −1587 | −1558 | −1726 | −2954 | −3510 | −2742 | 495 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 441(Q) | 854 | −2432 | 264 | −308 | −2743 | −1971 | −641 | −2483 | −231 | −2448 | 681 | 1414 | −2070 | 2317 | −737 | 1098 | −280 | −2050 | −2632 | −1958 | 496 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 442(L) | −1684 | −1481 | −3911 | −3303 | −1234 | −3289 | −2179 | 1310 | −2938 | 2230 | −330 | −2893 | −3277 | −217 | −2785 | −2389 | 1516 | 294 | −1986 | −1687 | 497 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 443(I) | 1388 | −1660 | −4350 | −3774 | 339 | −3691 | −2667 | 1898 | −3436 | 1384 | −620 | −3337 | −3648 | −3052 | −3269 | −2821 | −1888 | 1594 | −2412 | −2096 | 498 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 444(N) | −429 | −1301 | −2255 | −1692 | −1310 | −2510 | −1317 | 965 | −1486 | −1142 | 1274 | 3200 | −2583 | 280 | −1696 | −1534 | −1102 | 282 | −1758 | −1363 | 499 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 445(H) | −989 | −2462 | 1140 | 1287 | −2782 | −1959 | 2073 | −2533 | −202 | −2477 | 1021 | 761 | −2054 | 1813 | 414 | 304 | −929 | −2083 | −2645 | −1962 | 500 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 446(Y) | −570 | −3515 | −4109 | −4216 | −224 | −4378 | 3141 | −3593 | −3871 | −3148 | −3048 | −3397 | −4538 | −3440 | −3721 | −3699 | −3833 | −3587 | −932 | 4339 | 501 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8312 | −9354 | −894 | −1115 | −701 | −1378 | * | * | | | | | | | | | | | | |
| 447(L) | −2249 | 853 | −4575 | −3952 | −1251 | −3905 | −2751 | 1774 | −3586 | 2535 | 1585 | −3549 | −3766 | −365 | −3344 | −3026 | −2171 | −949 | −2320 | −2132 | 502 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −183 | −8312 | −3108 | −894 | −1115 | −701 | −1378 | * | * | | | | | | | | | | | | |
| 448(F) | −1766 | −1521 | −4129 | −3513 | 1880 | −3413 | −2296 | 1109 | −3142 | 1880 | 1149 | −3061 | −3355 | −2682 | −2926 | −2524 | −64 | 1400 | −1992 | −1730 | 503 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −152 | −8137 | −3370 | −894 | −1115 | −1459 | −652 | * | * | | | | | | | | | | | | |
| 449(G) | −169 | −2301 | 1066 | 908 | −2620 | 1545 | −453 | −2372 | 447 | −2316 | −1391 | 848 | −1885 | 582 | 351 | 31 | −765 | −1922 | −2484 | −1799 | 504 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −149 | −7993 | −3412 | −894 | −1115 | −1838 | −473 | * | * | | | | | | | | | | | | |
| 450(A) | 1384 | −1474 | −1057 | 562 | −1568 | −1895 | −607 | −94 | 456 | −1390 | −635 | −723 | −1980 | −310 | −804 | −19 | 849 | 1219 | −1821 | −1317 | 505 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −253 | −7853 | −2678 | −894 | −1115 | −2104 | −382 | * | * | | | | | | | | | | | | |
| 451(R) | −58 | 1062 | −1873 | −1289 | −813 | −2052 | −847 | 394 | −1021 | 1151 | −9 | 206 | −2122 | −888 | 2151 | −1078 | −635 | −237 | −1248 | −861 | 506 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −368 | −7612 | −2186 | −894 | −1115 | −2433 | −295 | * | * | | | | | | | | | | | | |
| 452(G) | 887 | −1428 | −559 | −11 | −1592 | 1139 | −219 | −1235 | 94 | −486 | −578 | 661 | −1615 | 151 | 428 | 120 | −400 | −968 | −1734 | 343 | 507 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −296 | −7258 | −2484 | −894 | −1115 | −2747 | −233 | * | * | | | | | | | | | | | | |
| 453(K) | 359 | −1852 | −165 | 1529 | −2167 | −1348 | −26 | −1905 | 1558 | −1860 | −953 | 11 | −1461 | 1054 | −76 | 506 | −357 | −1473 | −2035 | −1367 | 508 |
| — | −147 | −500 | 233 | 43 | −381 | 398 | 105 | −626 | 210 | −465 | −721 | 275 | 394 | 45 | 96 | 359 | 117 | −369 | −295 | −250 | |
| — | −1078 | −936 | −8022 | −95 | −3976 | −125 | −3592 | * | * | | | | | | | | | | | | |

TABLE 3-continued

| | | | | | | | | | | | | | | | | | | | | | |
|---|---|---|---|---|---|---|---|---|---|---|---|---|---|---|---|---|---|---|---|---|---|
| 454(W) | −204 | 887 | 46 | 246 | −204 | −619 | 891 | −475 | 338 | −941 | 659 | 291 | −334 | 598 | 147 | −143 | 7 | −471 | 1260 | 199 | 510 |
| — | −148 | −500 | 233 | 43 | −381 | 399 | 107 | −627 | 211 | −466 | −721 | 276 | 394 | 45 | 96 | 359 | 118 | −369 | −295 | −250 | |
| — | −166 | −3224 | −9354 | −1658 | −550 | −701 | −1378 | * | * | | | | | | | | | | | | |
| 455(W) | −204 | 887 | 46 | 246 | −204 | −619 | 891 | −475 | 338 | −941 | 659 | 291 | −334 | 598 | 147 | −143 | 7 | −471 | 1260 | 199 | 518 |
| — | * | * | * | * | * | * | * | * | * | * | * | * | * | * | * | * | * | * | * | * | |
| — | * | * | * | * | * | * | * | * | 0 | | | | | | | | | | | | |

[1]Program name and version
[2]Name of the input sequence alignment file
[3]Length of the alignment: include indels
[4]Type of residues
[5]Map of the match states to the columns of the alignment
[6]Commands used to generate the file: this one means that hmmbuild (default parameters) was applied to the alignment file
[7]Commands used to generate the file: this one means that hmmcalibrate (default parameters) was pplied to the hmm profile
[8]Number of sequences in the alignment
[9]When the file was generated
[10]The trasition probability distribution for the null model (single G state).
[11]The symbol emission probability distribution for the null model (G tate); consists of K integers. The null probability used to convert these back to model probabilities is 1/K.
[12]The extreme value distribution parameters μ and lambda respectively, both floating point values. Lambda is positive and nonzero. These values are set when the model is calibrated with hmmcalibrate.

TABLE 4

HMMER2.0 [2.2 g][1]
NAME rpiA__exp__ver__seqs__aln__new[2]
LENG 253[3]
ALPH Amino[4]
MAP yes[5]
COM /app/public/hmmer/current/bin/hmmbuild rpiA__exp__ver__seqs__aln__new__hmm rpiA__exp__ver__seqs__aln__new.aln[6]
COM /app/public/hmmer/current/bin/hmmcalibrate rpiA__exp__ver__seqs__aln__new__hmm[7]
NSEQ 15[8]
DATE Sat Jan 16 09:55:05 2010[9]
XT −8455 −4 −1000 −1000 −8455 −4 −8455 −4
NULT −4 −8455[10]
NULE 595 −1558 85 338 −294 453 −1158 197 249 902 −1085 −142 −21 −313 45 531 201 384 −1998 −644[11]
EVD −207.921417 0.159331[12]

| HMM | A<br>m->m | C<br>m->i | D<br>m->d | E<br>i->m | F<br>i->i | G<br>d->m | H<br>d->d | I<br>b->m | K<br>m->e | L | M | N | P | Q | R | S | T | V | W | Y | |
|---|---|---|---|---|---|---|---|---|---|---|---|---|---|---|---|---|---|---|---|---|---|
| | −230 | * | −2761 | | | | | | | | | | | | | | | | | | |
| 1(P) | −737 | −726 | −2336 | −1756 | −665 | −2165 | −1015 | −235 | −1488 | 712 | 69 | −1565 | 2093 | −1249 | −1544 | 305 | −688 | 847 | −1150 | 1747 | 1 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −11 | −7657 | −8699 | −894 | −1115 | −701 | −1378 | −230 | * | | | | | | | | | | | | |
| 2(E) | −896 | −2357 | −337 | 1937 | −2694 | 686 | −508 | −2450 | −163 | −2405 | −1508 | −359 | 1381 | 1232 | −689 | 490 | −857 | −2002 | −2585 | −1884 | 2 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −11 | −7657 | −8699 | −894 | −1115 | −701 | −1378 | * | * | | | | | | | | | | | | |
| 3(T) | 776 | −1568 | −848 | −299 | −1788 | −1722 | −484 | −1424 | −182 | −181 | −788 | −539 | 400 | −126 | 1155 | 829 | 1334 | −1155 | −1948 | −1403 | 3 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −164 | −7657 | −3284 | −894 | −1115 | −701 | −1378 | * | * | | | | | | | | | | | | |
| 4(M) | −722 | −907 | −1742 | 801 | −904 | −2057 | −841 | −449 | −989 | 571 | 2667 | −1198 | 409 | −831 | −1222 | 254 | −664 | 1036 | −1329 | −929 | 4 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −470 | −1847 | * | * | | | | | | | | | | | | |
| 5(M) | −854 | −1678 | −1050 | 768 | −1792 | 350 | −656 | −1412 | −393 | 839 | 1786 | 1317 | −2043 | 938 | −829 | −899 | −793 | 175 | −2001 | −1473 | 5 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8026 | −9069 | −894 | −1115 | −701 | −1378 | * | * | | | | | | | | | | | | |
| 6(M) | 1489 | −1440 | −2497 | −1913 | −1434 | −2652 | −1456 | −980 | −1560 | 1063 | 3173 | 713 | −2731 | −1485 | 475 | −1692 | −1258 | −881 | −1874 | −1492 | 6 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8494 | −9536 | −894 | −1115 | −701 | −1378 | * | * | | | | | | | | | | | | |
| 7(P) | −1584 | −2285 | −2925 | −2913 | −4391 | −2437 | −3074 | −4165 | −3104 | −4334 | −3436 | 781 | 2689 | −2852 | −3344 | 1622 | 2304 | −3192 | −4531 | −4184 | 7 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8494 | −9536 | −894 | −1115 | −701 | −1378 | * | * | | | | | | | | | | | | |
| 8(Q) | −1529 | −1399 | −3529 | −2918 | −1266 | −3053 | −1906 | 710 | −2581 | 1247 | 2483 | 397 | −3086 | 2619 | −2501 | −2127 | −1468 | 501 | −1851 | −1517 | 8 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 9(D) | −3187 | −5226 | 2990 | 2718 | −5370 | −2929 | −2384 | −5371 | −2804 | −5200 | −4638 | −1518 | 637 | −2077 | −3812 | −2793 | −3290 | −4804 | −5388 | −4266 | 9 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 10(E) | −2442 | −4166 | 1948 | 2627 | −4408 | 189 | −1849 | −4252 | −1830 | −4154 | −3356 | −1303 | −3115 | 1028 | −2521 | 981 | −2456 | −3759 | −4336 | −3463 | 10 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 11(M) | 943 | −1386 | −3607 | −2981 | −1221 | −3043 | −1881 | −775 | −2556 | 2149 | 2228 | −2596 | −3078 | −2268 | 405 | −2123 | −1463 | −762 | −1801 | 1047 | 11 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |

TABLE 4-continued

| | | | | | | | | | | | | | | | | | | | | | |
|---|---|---|---|---|---|---|---|---|---|---|---|---|---|---|---|---|---|---|---|---|---|
| 12(K) | 169 | -3490 | -3589 | -3166 | -5083 | -3480 | -2618 | -4660 | 3794 | -4506 | -3835 | -2964 | -3899 | -2271 | -1432 | -2981 | -3039 | -4100 | -4333 | -4249 | 12 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -6 | -8606 | -9649 | -894 | -1115 | -701 | -1378 | * | * | | | | | | | | | | | | |
| 13(K) | -3239 | -3946 | -3896 | -2586 | -4772 | 115 | -1733 | -4104 | 3369 | -455 | -3105 | -2492 | -3753 | -1313 | 1582 | -3127 | -2940 | -3870 | -3649 | -3533 | 13 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -6 | -8606 | -9649 | -894 | -1115 | -701 | -1378 | * | * | | | | | | | | | | | | |
| 14(I) | 1509 | -2463 | -1132 | 514 | -2708 | -35 | -865 | 1583 | 582 | -861 | -1574 | -873 | -2292 | 670 | 608 | -1119 | -1135 | -2044 | -2692 | -2064 | 14 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -6 | -8606 | -9649 | -894 | -1115 | -701 | -1378 | * | * | | | | | | | | | | | | |
| 15(A) | 3213 | -2363 | -4869 | -5046 | -4146 | -2886 | -4289 | -2125 | -4791 | -3574 | -3168 | -3587 | -3630 | -4386 | -4544 | -2261 | -2328 | 1716 | -4821 | -4601 | 15 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -6 | -8606 | -9649 | -894 | -1115 | -701 | -1378 | * | * | | | | | | | | | | | | |
| 16(A) | 3284 | -2506 | -4607 | -4949 | -5111 | 1562 | -4350 | -4970 | -4949 | -5213 | -4291 | -3502 | -3559 | -4436 | -4658 | -2168 | -2389 | -3707 | -5210 | -5250 | 16 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -6 | -8606 | -9649 | -894 | -1115 | -701 | -1378 | * | * | | | | | | | | | | | | |
| 17(W) | -1293 | -1726 | -1890 | -43 | 736 | -2518 | 1428 | -1343 | 1054 | -1609 | -900 | -1471 | -2593 | -1075 | -1526 | 156 | -1233 | 353 | 3270 | 2559 | 17 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -6 | -8606 | -9649 | -894 | -1115 | -701 | -1378 | * | * | | | | | | | | | | | | |
| 18(K) | 1539 | -2931 | -1365 | 1110 | -3311 | 17 | -1038 | -3017 | 2042 | -2929 | -2039 | -1095 | -2543 | -588 | 1487 | -1418 | -1461 | -2592 | -3051 | -2448 | 18 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -6 | -8606 | -9649 | -894 | -1115 | -701 | -1378 | * | * | | | | | | | | | | | | |
| 19(A) | 3342 | 2232 | -4964 | -5274 | -4911 | 359 | -4286 | -4696 | -4933 | -4984 | -4038 | -3392 | -3380 | -4389 | -4561 | -1937 | -2154 | -3450 | -5135 | -5108 | 19 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -6 | -8606 | -9649 | -894 | -1115 | -701 | -1378 | * | * | | | | | | | | | | | | |
| 20(V) | 116 | -1749 | -4396 | -3834 | -1888 | 940 | -2760 | 904 | -3499 | 980 | -991 | -3381 | -3735 | -3170 | -3361 | -2847 | -1962 | 2618 | -2595 | -2237 | 20 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -6 | -8606 | -9649 | -894 | -1115 | -701 | -1378 | * | * | | | | | | | | | | | | |
| 21(K) | 96 | -2683 | 1087 | 1620 | -3002 | -25 | -837 | -2753 | 1918 | -468 | -1775 | -799 | -2267 | 841 | -934 | -1087 | -1150 | -2304 | -2867 | -2182 | 21 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -6 | -8606 | -9649 | -894 | -1115 | -701 | -1378 | * | * | | | | | | | | | | | | |
| 22(Y) | -1358 | -1336 | -2944 | -2345 | 1772 | -2797 | -1583 | -854 | 291 | -31 | 1632 | -2161 | -2854 | -1821 | 421 | -327 | -1297 | -762 | -1716 | 3221 | 22 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -6 | -8606 | -9649 | -894 | -1115 | -701 | -1378 | * | * | | | | | | | | | | | | |
| 23(V) | 49 | -2304 | -5310 | -4886 | 865 | -4900 | -4331 | 1688 | -4706 | -1790 | -1614 | -4565 | -4771 | -4499 | -4702 | -4149 | -2706 | 3181 | -3977 | -3543 | 23 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -6 | -8606 | -9649 | -894 | -1115 | -701 | -1378 | * | * | | | | | | | | | | | | |
| 24(Q) | -2247 | -3872 | 861 | 1799 | -4155 | -2664 | -1668 | -3953 | 1967 | -3853 | -3025 | -1269 | -3002 | 3006 | -1994 | -2025 | -2231 | -3484 | -4010 | -3228 | 24 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -6 | -8606 | -9649 | -894 | -1115 | -701 | -1378 | * | * | | | | | | | | | | | | |
| 25(D) | -2501 | -4054 | 2742 | -1070 | -4562 | -2747 | -2018 | -4408 | 73 | -4325 | -3550 | -1429 | 282 | -1657 | -2695 | 2457 | -2567 | -3871 | -4505 | -3648 | 25 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -6 | -8606 | -9649 | -894 | -1115 | -701 | -1378 | * | * | | | | | | | | | | | | |
| 26(G) | -3037 | -4879 | 844 | -1122 | -5169 | 3241 | 1798 | -5175 | -2686 | -5034 | -4423 | 896 | -3469 | -2028 | -3602 | -2695 | -3147 | -4601 | -5204 | -4139 | 26 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -6 | -8606 | -9649 | -894 | -1115 | -701 | -1378 | * | * | | | | | | | | | | | | |
| 27(M) | -1469 | 2013 | -3003 | -2471 | -2046 | -2661 | -1984 | -1596 | 409 | -1917 | 4312 | -2265 | -2961 | -2007 | -2198 | -161 | 1213 | -1418 | -2455 | -2088 | 27 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -6 | -8606 | -9649 | -894 | -1115 | -701 | -1378 | * | * | | | | | | | | | | | | |
| 28(V) | -2412 | -2097 | -4795 | -4276 | -2457 | -4302 | -3498 | 2310 | -3835 | -1736 | -1426 | -3927 | -4279 | -3728 | 1385 | -3488 | 351 | 2653 | -3372 | -2980 | 28 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -6 | -8606 | -9649 | -894 | -1115 | -701 | -1378 | * | * | | | | | | | | | | | | |

TABLE 4-continued

| | | | | | | | | | | | | | | | | | | | | | |
|---|---|---|---|---|---|---|---|---|---|---|---|---|---|---|---|---|---|---|---|---|---|
| 29(I) | −2696 | −2288 | −5253 | −4805 | −2613 | 12 | −4162 | 2603 | −4599 | 965 | −1484 | −4475 | −4685 | −4347 | −4561 | −4044 | −2671 | 2370 | −3804 | −3421 | 29 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 30(G) | −5249 | −4846 | −5805 | −6182 | −6521 | 3848 | −5650 | −7348 | −6455 | −6931 | −6666 | −5891 | −5413 | −6249 | −6011 | −5566 | −5614 | −6629 | −5452 | −6497 | 30 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 31(L) | 37 | −2467 | −5417 | −4944 | −2323 | −4975 | −4218 | 1048 | −4726 | 2497 | −1169 | −4643 | −4761 | −4320 | −4618 | −4207 | −2845 | 1769 | −3670 | −3419 | 31 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 32(G) | −5249 | −4846 | −5805 | −6182 | −6521 | 3848 | −5650 | −7348 | −6455 | −6931 | −6666 | −5891 | −5413 | −6249 | −6011 | −5566 | −5614 | −6629 | −5452 | −6497 | 32 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 33(T) | −1742 | −2395 | −3358 | −3587 | −4782 | −2578 | −3671 | −4600 | −3940 | −4815 | −3908 | 840 | −3343 | −3566 | −4000 | 1239 | 3538 | −3465 | −4970 | −4726 | 33 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 34(G) | −2161 | −2733 | −4416 | −4762 | −5231 | 3632 | −4392 | −5148 | −4912 | −5359 | −4485 | −3619 | −3739 | −4472 | −4692 | −2409 | 608 | −3930 | −5223 | −5307 | 34 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 35(S) | −2873 | −3334 | −4781 | −5130 | −5373 | −3522 | −4723 | −5714 | −5297 | −5786 | −5056 | −4198 | −4255 | −4941 | −5056 | 3723 | −3329 | −4590 | −5178 | −5309 | 35 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 36(T) | −3493 | −3798 | −5272 | −5603 | −5670 | −3975 | −5053 | −5807 | −5594 | −5903 | −5378 | −4752 | −4656 | −5368 | −5298 | −3760 | 4069 | −4969 | −5264 | −5668 | 36 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 37(A) | 2501 | −2145 | −4938 | −4524 | −2662 | −4096 | −3781 | 1043 | −4277 | −1902 | −1607 | −4013 | −4259 | −4022 | −4221 | −3341 | 283 | 2230 | −3629 | −3236 | 37 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 38(A) | 1970 | 1799 | −1743 | −1181 | 624 | −2445 | −1173 | −1434 | 1352 | −1689 | −962 | 288 | −2526 | −945 | 436 | −1413 | −1196 | 338 | −2161 | −1697 | 38 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 39(H) | −4508 | −3790 | −5387 | −5470 | 1683 | −5200 | 3664 | −3594 | −5055 | −299 | −3093 | −3993 | 617 | −4051 | −4592 | −4400 | −4398 | −3664 | −1018 | 3609 | 39 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 40(F) | 1988 | −1682 | −4234 | −3615 | 2416 | −3501 | −2380 | −678 | −3235 | 314 | 1738 | −3145 | −3486 | −2808 | −3032 | −2603 | −1835 | 1303 | −2141 | −1841 | 40 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 41(V) | 101 | −2050 | −4873 | −4368 | −2350 | −4322 | −3494 | 2224 | −4095 | −23 | −1334 | −3975 | 459 | −3818 | −4011 | −3497 | −2359 | 2700 | −3265 | −2882 | 41 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 42(D) | −199 | −2647 | 1670 | 1649 | −2967 | −2145 | −806 | −2718 | 613 | −586 | −1737 | 777 | −2240 | −347 | 505 | 732 | −1114 | −2269 | −2831 | −2148 | 42 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 43(R) | 551 | −2283 | −1313 | 1080 | −2461 | −2298 | −969 | −2110 | −600 | −480 | −1419 | −1024 | −2387 | −583 | 2635 | −1234 | 447 | −1829 | −2558 | 937 | 43 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 44(I) | −4159 | −3553 | −6565 | −5989 | −1742 | −6358 | −5051 | 2598 | −5794 | 2452 | 1878 | −6079 | −5396 | −4572 | −5288 | −5733 | −4007 | −1733 | −3572 | −3789 | 44 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 45(G) | 946 | −3028 | 669 | −1058 | −3786 | 2588 | −1624 | −3558 | 551 | −3534 | −2655 | −1340 | −2817 | −1217 | −1911 | 814 | −1831 | −3015 | −3719 | −3026 | 45 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |

TABLE 4-continued

| | | | | | | | | | | | | | | | | | | | | | |
|---|---|---|---|---|---|---|---|---|---|---|---|---|---|---|---|---|---|---|---|---|---|
| 46(Q) | −1298 | −2751 | −1122 | 1954 | −3088 | −2248 | −885 | −2826 | 726 | −2758 | −1843 | 1435 | −2342 | 2103 | 593 | −1176 | 850 | −2383 | −2910 | −2251 | 46 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −185 | −8606 | −3083 | −894 | −1115 | −701 | −1378 | * | * | | | | | | | | | | | | |
| 47(R) | 283 | −1953 | −1693 | −1097 | −2055 | 115 | −1074 | −1648 | 625 | 1378 | −1117 | −1278 | −2505 | −786 | 1948 | −1413 | −1239 | −1458 | −2268 | 1170 | 47 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8427 | −9469 | −894 | −1115 | −1600 | −578 | * | * | | | | | | | | | | | | |
| 48(L) | −2911 | −2569 | −5151 | 303 | 1149 | −4652 | −3420 | 1605 | −4248 | 2578 | −352 | −4269 | −4351 | −3576 | −3981 | −3811 | −2817 | −1280 | −2759 | −2609 | 48 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8427 | −9469 | −894 | −1115 | −1600 | −578 | * | * | | | | | | | | | | | | |
| 49(K) | −1564 | −2916 | −1478 | 645 | −3330 | −2470 | 1776 | −3006 | 2205 | −2887 | −2013 | −1109 | −2537 | 1193 | 2170 | −71 | −1467 | −2594 | −2975 | −2424 | 49 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8427 | −9469 | −894 | −1115 | −333 | −2277 | * | * | | | | | | | | | | | | |
| 50(M) | 651 | −2637 | 567 | 1694 | −2956 | −2140 | −799 | −2706 | −380 | −2652 | 1818 | 777 | −2234 | 670 | 506 | 212 | 437 | −2258 | −2821 | −2139 | 50 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 51(W) | −246 | 982 | 39 | 198 | −144 | −596 | 928 | −456 | 289 | −954 | 709 | 281 | −285 | 575 | 131 | −180 | −17 | −477 | 1369 | 255 | 51 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 52(G) | −1840 | −3290 | −1005 | 1266 | −3716 | 2571 | −1423 | −3480 | 1230 | −3415 | −2544 | −1185 | 523 | −1002 | −1594 | −140 | −1825 | −3009 | −3580 | −2871 | 52 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 53(K) | −2019 | −3475 | −1064 | 1977 | −3902 | 872 | −1515 | −3655 | 2684 | −3564 | −2713 | −1281 | −2892 | −1099 | −1547 | 214 | −1995 | −3192 | −3702 | −3015 | 53 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 54(L) | −2125 | −1933 | −4188 | −360 | 979 | −3693 | −2514 | 1391 | −3240 | 2496 | −450 | −3247 | −3638 | 472 | −3100 | −2790 | −2053 | −1108 | −2268 | −1993 | 54 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 55(K) | 169 | −2564 | −1050 | 285 | −2852 | −2157 | 1513 | 583 | 1919 | −2566 | −1662 | −805 | −2249 | 692 | −913 | 147 | 883 | −2168 | −2767 | 905 | 55 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −452 | −8606 | −1909 | −894 | −1115 | −701 | −1378 | * | * | | | | | | | | | | | | |
| 56(D) | −2633 | −4616 | 2798 | 1104 | −4766 | 1497 | −1872 | −4720 | −2192 | −4570 | −3939 | 2177 | −3037 | −1549 | −3116 | −2268 | −2714 | −4175 | −4770 | −3697 | 56 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8162 | −9204 | −894 | −1115 | −201 | −2945 | * | * | | | | | | | | | | | | |
| 57(I) | −1788 | −1923 | −2876 | −34 | −2012 | −3091 | −1729 | 2383 | 146 | −1745 | −1130 | −2188 | −3132 | −1628 | 630 | −2165 | −1708 | 2312 | −2394 | −2024 | 57 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 58(V) | 950 | −1303 | −3775 | −3161 | 749 | 481 | −1956 | 1236 | −2782 | −1142 | −531 | −2677 | −3091 | −2425 | −2614 | −2126 | 478 | 2311 | −1840 | −1493 | 58 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −254 | −8606 | −2657 | −894 | −1115 | −701 | −1378 | * | * | | | | | | | | | | | | |
| 59(G) | 1097 | 2397 | −4641 | −4884 | −4602 | 3072 | −3964 | −4394 | −4563 | −4663 | −3717 | −3098 | −3108 | −4043 | −4241 | 663 | −1876 | −3167 | −4840 | −4782 | 59 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8359 | −9402 | −894 | −1115 | −282 | −2492 | * | * | | | | | | | | | | | | |
| 60(V) | −3033 | −2523 | −5726 | −5424 | −3217 | −5556 | −5669 | 2753 | −5400 | −1961 | −1904 | −5240 | −5307 | −5371 | −5582 | −4951 | −3030 | 3063 | −5010 | −4474 | 60 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 61(P) | −2379 | −3335 | −1479 | 534 | −4966 | −2801 | −2763 | −4855 | −2948 | −4880 | −4125 | −2019 | 3631 | −2490 | −3505 | 1442 | −2680 | −4001 | −5009 | −4336 | 61 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 62(T) | −1747 | −2400 | −3347 | −3588 | −4790 | −2581 | −3681 | −4611 | −3958 | −4826 | −3921 | 841 | −3347 | −3581 | −4014 | 849 | 3623 | −3472 | −4980 | −4736 | 62 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |

TABLE 4-continued

| | | | | | | | | | | | | | | | | | | | | | |
|---|---|---|---|---|---|---|---|---|---|---|---|---|---|---|---|---|---|---|---|---|---|
| 63(S) | −1904 | −2581 | −2882 | −3144 | −4596 | 354 | 1785 | −4698 | −3630 | −4845 | −3985 | −2780 | −3416 | −3330 | −3787 | 3370 | −2324 | −3611 | −4803 | −4364 | 63 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 64(W) | −1305 | −1269 | −49 | −2357 | 2148 | −2761 | −1589 | 1112 | 541 | −1124 | −466 | −2157 | −2819 | −1834 | 306 | −1811 | 53 | 1055 | 2259 | 963 | 64 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 65(Q) | 1055 | −2636 | 499 | 528 | −2956 | −2140 | −799 | −2705 | 391 | −500 | −1725 | −776 | −2233 | 1686 | 1507 | 253 | 37 | −2257 | −2820 | −2138 | 65 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 66(T) | 1634 | −2258 | −4701 | −4919 | −4847 | −2541 | −4146 | −4631 | −4680 | −4902 | −3957 | −3298 | −3344 | −4195 | −4415 | 1536 | 3130 | −3409 | −5076 | −5002 | 66 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 67(K) | −171 | −2654 | −1044 | 1165 | −2977 | −2164 | 1013 | −2723 | 1667 | −2667 | −1744 | −800 | −2256 | 668 | 1361 | −1073 | 1426 | −2278 | −2833 | 365 | 67 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 68(E) | −1375 | −2585 | −1158 | 2308 | −2791 | −2325 | −1026 | −2474 | −645 | 884 | 1250 | 799 | −2444 | 1760 | −1110 | −1302 | −1316 | −2150 | −2817 | −2202 | 68 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 69(Q) | −2625 | −3132 | −3243 | −2304 | −2997 | −3502 | −1672 | −2796 | 1761 | 1816 | −2138 | −2292 | −3490 | 2657 | −650 | −2681 | −2442 | −2718 | 2444 | −2596 | 69 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 70(A) | 2473 | 2023 | −4541 | −3996 | −1860 | −3722 | −2896 | 1588 | −3650 | 1105 | −917 | −3494 | −3791 | −3269 | −3484 | −2883 | −2090 | −455 | −2677 | −2364 | 70 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 71(M) | −163 | −1413 | −2467 | −184 | −1401 | −2662 | −1451 | 1231 | 941 | 1253 | 1459 | −1863 | −2726 | −1500 | 1249 | −1682 | −1234 | 130 | −1839 | −1450 | 71 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 72(S) | −132 | −2663 | 576 | 1175 | −2984 | −2154 | −818 | −2735 | 664 | −2679 | −1753 | −789 | −2251 | 1678 | 545 | 1847 | −1129 | −2285 | −2845 | −2162 | 72 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 73(L) | −1356 | −2091 | −1474 | 385 | −2077 | −2434 | 1400 | −1797 | −948 | 1932 | −1251 | 741 | −2540 | −869 | −1365 | 189 | −1298 | −1590 | −2351 | 1829 | 73 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 74(G) | −3022 | −4956 | 843 | 559 | −5144 | 3241 | −2261 | −5081 | 488 | −4930 | −4294 | −1476 | −3437 | −1936 | −3360 | −2665 | −3099 | −4543 | −5117 | −4079 | 74 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 75(I) | −3760 | −3207 | −6240 | −5795 | −2030 | −6009 | −5114 | 3491 | −5625 | 1544 | −811 | −5748 | −5357 | −4747 | −5322 | −5422 | −3681 | −963 | −3819 | −3848 | 75 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 76(P) | −2101 | −3282 | −1794 | −1339 | −3744 | −2873 | 578 | −3375 | 489 | −3279 | −2468 | −1559 | 3420 | 1078 | −804 | −1992 | 838 | −3013 | −3367 | −2886 | 76 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 77(L) | −3556 | −3020 | −6109 | −5654 | −2129 | −5886 | −5095 | 1390 | −5518 | 2765 | −891 | −5573 | −5293 | −4749 | −5286 | −5238 | −3487 | 1330 | −3904 | −3921 | 77 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 78(S) | 637 | −1674 | −2006 | −1449 | 1219 | 13 | −1333 | −1332 | 426 | −1615 | −906 | −1557 | −2615 | −1182 | −1625 | 1757 | 430 | 993 | −2120 | −1685 | 78 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 79(D) | −1806 | −3240 | 2835 | 629 | −3592 | −2475 | −1415 | −3345 | −1173 | −3327 | −2466 | −1143 | −2741 | −1003 | −1736 | 964 | 1574 | −398 | −3534 | −2811 | 79 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |

TABLE 4-continued

| | | | | | | | | | | | | | | | | | | | | | |
|---|---|---|---|---|---|---|---|---|---|---|---|---|---|---|---|---|---|---|---|---|---|
| 80(L) | −3783 | 1558 | −6171 | −5577 | −1700 | −5769 | −4529 | 789 | −5319 | 2913 | 1869 | −5467 | −5104 | −4311 | −4901 | −5031 | −3656 | −1664 | −3378 | −3488 | 80 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 81(D) | −2988 | −4951 | 3191 | 1435 | −5107 | 233 | −2239 | −5050 | −2530 | −4905 | −4255 | 1432 | 516 | −1912 | −3432 | −2631 | −3062 | −4510 | −5103 | −4047 | 81 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 82(E) | −199 | −2647 | 182 | 1998 | −2968 | −2144 | −805 | −2719 | 666 | −2663 | −1736 | −779 | 233 | 1687 | 617 | 713 | −1113 | −2269 | −2830 | −2147 | 82 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 83(H) | −1636 | −2253 | −1701 | 345 | −1931 | −2676 | 3730 | −1933 | −1146 | −2136 | −1426 | −1506 | −2794 | 509 | −1481 | −1727 | −1574 | 1746 | −2290 | 1947 | 83 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 84(P) | −130 | −2884 | 1913 | −1849 | −4557 | 177 | −2566 | −4373 | −2611 | −4425 | −3568 | −1983 | 3043 | −2250 | −3137 | 1124 | −2248 | −3531 | −4610 | −3997 | 84 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −228 | −8606 | −2799 | −894 | −1115 | −701 | −1378 | * | * | | | | | | | | | | | | |
| 85(H) | 205 | −2492 | −882 | 1369 | −2809 | −2006 | 1655 | −2556 | 559 | −2506 | −1583 | 870 | −2099 | −206 | 1522 | 468 | −970 | 403 | −2677 | −1998 | 85 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8385 | −9427 | −894 | −1115 | −299 | −2417 | * | * | | | | | | | | | | | | |
| 86(I) | −3224 | −2707 | −5857 | −5478 | −2594 | −5663 | −5269 | 2819 | −5394 | 1787 | −1334 | −5328 | −5265 | −4992 | −5371 | −5020 | −3192 | 1785 | −4337 | −4130 | 86 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 87(D) | −3875 | −4833 | 4046 | −2276 | −5882 | −17 | −3426 | −6149 | −3929 | −5938 | −5452 | −2631 | −4258 | −3213 | −4722 | −3665 | −4079 | −5478 | −5444 | −5121 | 87 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 88(I) | −3346 | −2848 | −5896 | −5433 | −2183 | −5600 | −4817 | 2575 | −5270 | 1760 | 1774 | −5271 | −5138 | −4629 | −5085 | −4902 | −3286 | 1748 | −3845 | −3780 | 88 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 89(A) | 2412 | 2004 | −3508 | −2967 | −1606 | −2730 | −2026 | −1145 | −2653 | −1500 | −839 | −2515 | −2981 | −2346 | −2595 | 433 | 476 | 526 | −2086 | 1664 | 89 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 90(I) | −3029 | −2537 | −5660 | −5302 | 1731 | −5418 | −4966 | 3297 | −5207 | −1645 | −1625 | −5066 | −5155 | −4983 | −5255 | −4749 | −3011 | 1800 | −4310 | −3807 | 90 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 91(D) | −5403 | −5247 | 4201 | −3898 | −6360 | −4647 | −4682 | −7143 | −5306 | −6710 | −6481 | −4228 | −5165 | −4724 | −5628 | −5311 | −5571 | −6677 | −5444 | −5968 | 91 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 92(G) | −5249 | −4846 | −5805 | −6182 | −6521 | 3848 | −5650 | −7348 | −6455 | −6931 | −6666 | −5891 | −5413 | −6249 | −6011 | −5566 | −5614 | −6629 | −5452 | −6497 | 92 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 93(A) | 3485 | −2326 | −4694 | −5003 | −4905 | −2605 | −4239 | −4596 | −4794 | −4945 | −4047 | −3372 | −3411 | −4314 | −4490 | −1981 | 567 | −3438 | −5129 | −5076 | 93 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 94(D) | −5403 | −5247 | 4201 | −3898 | −6360 | −4647 | −4682 | −7143 | −5306 | −6710 | −6481 | −4228 | −5165 | −4724 | −5628 | −5311 | −5571 | −6677 | −5444 | −5968 | 94 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 95(E) | −5429 | −5227 | −3611 | 3948 | −6343 | −4680 | −4698 | −7062 | −5156 | −6644 | −6413 | −4312 | −5188 | −4740 | −5393 | −5360 | −5587 | −6630 | −5420 | −5964 | 95 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 96(V) | −3033 | −2523 | −5726 | −5424 | −3217 | −5555 | −5668 | 2643 | −5400 | −1961 | −1904 | −5239 | −5306 | −5370 | −5581 | −4949 | −3030 | 3136 | −5009 | −4473 | 96 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |

TABLE 4-continued

| | | | | | | | | | | | | | | | | | | | | | |
|---|---|---|---|---|---|---|---|---|---|---|---|---|---|---|---|---|---|---|---|---|---|
| 97(D) | −6 | −5112 | 3589 | 565 | −5264 | −2894 | −2320 | −5237 | −2694 | −5079 | −4481 | 1439 | −3470 | −2006 | −3663 | −2720 | −3193 | −4680 | −5282 | −4176 | 97 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 98(P) | 804 | −2571 | −1486 | 1220 | −3189 | 876 | −1637 | −2859 | −1407 | −376 | −2177 | −1471 | 2820 | −1281 | −1874 | −1625 | −1682 | −2469 | −3304 | −2730 | 98 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 99(N) | −205 | −2652 | 1485 | −493 | −105 | −114 | 1258 | −2705 | −428 | −2663 | −1746 | 2523 | −2265 | 1041 | −936 | −1085 | 326 | −2268 | −2842 | −2164 | 99 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 100(L) | −3639 | −3200 | −5894 | −5269 | 1023 | −5456 | −4056 | −1167 | −4824 | 2795 | 1608 | −5071 | −4913 | −4047 | 1212 | −4670 | −3510 | −1887 | −3119 | −3039 | 100 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 101(N) | 92 | −2719 | 216 | 355 | 350 | −2197 | −889 | −2773 | −493 | −2730 | −1816 | 2867 | −2312 | 1644 | −1006 | −1141 | 440 | −2334 | −2909 | −2225 | 101 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 102(W) | −246 | 982 | 39 | 198 | −144 | −596 | 928 | −456 | 289 | −954 | 709 | 281 | −285 | 575 | 131 | −180 | −17 | −477 | 1369 | 255 | 102 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 103(L) | −3490 | 2064 | −5882 | −5291 | −1694 | −5373 | −4208 | −978 | −5002 | 2833 | 2334 | −5074 | −4889 | −4137 | −4644 | −4594 | −3387 | 66 | −3257 | −3288 | 103 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 104(I) | −3039 | −2533 | −5727 | −5426 | −3184 | −5538 | −5636 | 3576 | −5395 | −1926 | −1879 | −5235 | −5297 | −5348 | −5564 | −4933 | −3037 | 1922 | −4967 | −4448 | 104 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 105(K) | −5328 | −4974 | −5211 | −4878 | −6129 | −4874 | −4145 | −6424 | 4029 | −5979 | −5562 | −4797 | −5200 | −3978 | −3061 | −5417 | −5268 | −6124 | −5037 | −5529 | 105 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 106(G) | −5249 | −4846 | −5805 | −6182 | −6521 | 3848 | −5650 | −7348 | −6455 | −6931 | −6666 | −5891 | −5413 | −6249 | −6011 | −5566 | −5614 | −6629 | −5452 | −6497 | 106 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 107(R) | −2636 | −3198 | −3874 | −3158 | −4390 | 2550 | −2437 | −4040 | −1266 | −3942 | 1570 | −2880 | −3743 | −2106 | 3016 | −2763 | −2767 | −3611 | −3984 | −3796 | 107 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 108(G) | −5249 | −4846 | −5805 | −6182 | −6521 | 3848 | −5650 | −7348 | −6455 | −6931 | −6666 | −5891 | −5413 | −6249 | −6011 | −5566 | −5614 | −6629 | −5452 | −6497 | 108 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 109(G) | 2252 | −2525 | −4568 | −4913 | −5126 | 3079 | −4351 | −4991 | −4948 | −5230 | −4310 | −3506 | −3573 | −4435 | −4665 | −2186 | −2407 | −3727 | −5216 | −5259 | 109 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 110(C) | 2793 | 4147 | −4964 | −5261 | −4862 | −2544 | −4256 | −4638 | −4898 | −4930 | −3986 | −3366 | −3355 | −4357 | −4530 | 672 | −2123 | −3409 | −5104 | −5057 | 110 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 111(L) | −4311 | −3952 | −5060 | −5019 | −1868 | −5013 | 2699 | −2439 | −4294 | 3063 | −1762 | −4672 | −5079 | −4226 | −4142 | −4791 | −4305 | −3086 | −2839 | −2000 | 111 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 112(T) | 164 | −1449 | −3931 | −3315 | 932 | −3182 | −2099 | −660 | −2935 | 1773 | −491 | −2835 | −3223 | −2550 | −2754 | −2281 | 2260 | 597 | −1938 | −1612 | 112 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 113(R) | −2890 | −3436 | −3581 | −2475 | −3522 | −3676 | −1754 | −3027 | −525 | −186 | 1460 | −2430 | −3634 | 2800 | 3084 | −2906 | −2666 | −3028 | −3334 | −3116 | 113 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |

TABLE 4-continued

| | | | | | | | | | | | | | | | | | | | | | |
|---|---|---|---|---|---|---|---|---|---|---|---|---|---|---|---|---|---|---|---|---|---|
| 114(E) | −5429 | −5227 | −3611 | 3948 | −6343 | −4680 | −4698 | −7062 | −5156 | −6644 | −6413 | −4312 | −5188 | −4740 | −5393 | −5360 | −5587 | −6630 | −5420 | −5964 | 114 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 115(K) | −5328 | −4974 | −5211 | −4878 | −6129 | −4874 | −4145 | −6424 | 4029 | −5979 | −5562 | −4797 | −5200 | −3978 | −3061 | −5417 | −5268 | −6124 | −5037 | −5529 | 115 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 116(I) | −3952 | −3380 | −6396 | −5850 | −1816 | −6157 | −4982 | 3216 | −5657 | 1173 | 3054 | −5863 | −5334 | −4575 | −5231 | −5508 | −3828 | −1412 | −3614 | −3770 | 116 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 117(V) | −3031 | −2523 | −5722 | −5421 | −3211 | −5544 | −5655 | 2189 | −5395 | −1957 | −1901 | −5233 | −5300 | −5363 | −5573 | −4938 | −3029 | 3361 | −4999 | −4465 | 117 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 118(E) | 1970 | −3440 | 671 | 2293 | −3739 | −2490 | −1412 | −3525 | −1174 | −3457 | −2584 | −1111 | −2758 | 1033 | −1753 | 247 | −1851 | −3060 | −3634 | −2874 | 118 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 119(Y) | 479 | −1939 | −1580 | −1027 | −2064 | 986 | −1121 | −1671 | −906 | −1890 | 979 | −1235 | −2471 | −829 | 456 | 1294 | 1228 | −1462 | −2320 | 1715 | 119 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 120(M) | 1611 | −1324 | −2720 | −2134 | −1301 | −2713 | −1527 | 300 | −1897 | −1184 | 1616 | 422 | −2775 | −1681 | 273 | 867 | −1236 | 1045 | −1761 | 1090 | 120 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 121(A) | 2919 | −2259 | −4733 | −4972 | −4875 | −2541 | −4174 | −4667 | −4727 | −4936 | −3986 | −3309 | −3346 | −4229 | −4444 | 1993 | 632 | −3423 | −5102 | −5039 | 121 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 122(K) | −208 | −2868 | 1748 | 32 | −3182 | −119 | −979 | −2941 | 2184 | −2882 | −1967 | 693 | −2391 | −529 | −1126 | 931 | −1319 | −2488 | −3051 | −2350 | 122 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 123(K) | −1319 | −2748 | −1178 | 1128 | −3085 | −2275 | −895 | −2813 | 2147 | −527 | −1841 | 1533 | −2363 | −440 | 682 | −1201 | 1137 | −2380 | −2902 | −2257 | 123 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 124(F) | −5282 | −4222 | −5670 | −6022 | 4365 | −5536 | −1776 | −4163 | −5588 | −3467 | −3566 | −4190 | −5408 | −4327 | −4958 | −4815 | −5143 | −4332 | −1023 | 1795 | 124 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 125(I) | −2903 | −2437 | −5499 | −5129 | −2762 | −5200 | −4596 | 3199 | −4992 | −1834 | −1726 | −4835 | −5012 | −4813 | −5032 | −4497 | −2886 | 2318 | −4089 | 1137 | 125 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 126(V) | −2960 | 3127 | −5650 | −5327 | −3175 | −5388 | −5384 | 1758 | −5271 | −1976 | −1886 | −5095 | −5193 | −5212 | −5414 | −4747 | −2959 | 3177 | −4838 | −4319 | 126 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 127(I) | −3151 | −2634 | −5806 | −5453 | −2784 | −5630 | −5388 | 3436 | −5389 | 727 | −1511 | −5292 | −5279 | −5110 | −5436 | −4998 | −3128 | 1449 | −4536 | −4235 | 127 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 128(A) | 2586 | −2237 | −4702 | −4879 | −4297 | 267 | −4054 | −3146 | −4639 | −4101 | −3401 | −3348 | −3405 | −4170 | −4370 | −1993 | −2139 | 2577 | −4712 | −4545 | 128 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 129(D) | −5403 | −5247 | 4201 | −3898 | −6360 | −4647 | −4682 | −7143 | −5306 | −6710 | −6481 | −4228 | −5165 | −4724 | −5628 | −5311 | −5571 | −6677 | −5444 | −5968 | 129 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 130(E) | −30 | −2617 | 1256 | 1786 | 485 | −421 | 1430 | −2656 | −420 | −2624 | −1712 | −802 | −2257 | −375 | −925 | 940 | −1128 | −2228 | −2811 | 881 | 130 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |

TABLE 4-continued

| | | | | | | | | | | | | | | | | | | | | | |
|---|---|---|---|---|---|---|---|---|---|---|---|---|---|---|---|---|---|---|---|---|---|
| 131(S) | −1461 | −2264 | −2052 | −1528 | −2919 | 128 | −1620 | −2558 | −1253 | −285 | −1920 | −1643 | −2754 | −1284 | 1946 | 2096 | 1496 | −2197 | −3053 | −2562 | 131 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 132(K) | −5328 | −4974 | −5211 | −4878 | −6129 | −4874 | −4145 | −6424 | 4029 | −5979 | −5562 | −4797 | −5200 | −3978 | −3061 | −5417 | −5268 | −6124 | −5037 | −5529 | 132 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 133(L) | 684 | −2365 | 1274 | −665 | −2565 | −2248 | −924 | −2233 | 1265 | 1502 | 818 | −946 | −2341 | 793 | −1026 | −1179 | −1166 | −1922 | −2623 | −2025 | 133 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 134(V) | −1773 | 2120 | −4891 | −4942 | −3801 | −2776 | −3984 | −2112 | −4590 | −3422 | −2885 | −3451 | −3498 | −4162 | −4326 | 1728 | −2163 | 3177 | −4388 | −4131 | 134 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −254 | −8606 | −2657 | −894 | −1115 | −701 | −1378 | * | * | | | | | | | | | | | | |
| 135(D) | −1208 | −2701 | 2036 | 489 | −3015 | −2087 | −811 | −2772 | 1571 | −2713 | −1799 | −717 | 1406 | 1207 | −945 | −1073 | 556 | −2321 | −2881 | −2183 | 135 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8359 | −9402 | −894 | −1115 | −282 | −2492 | * | * | | | | | | | | | | | | |
| 136(K) | −1197 | −2365 | −1180 | −629 | −2575 | 284 | 1001 | −107 | 2043 | −2332 | −1485 | 700 | −2311 | 1006 | −996 | −1142 | −1135 | 636 | −2616 | 1441 | 136 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 137(H) | −1429 | −1419 | −2861 | −2369 | −1354 | −75 | 2475 | 852 | −2094 | 2161 | −613 | 587 | −2915 | −1899 | −2147 | −1910 | −1379 | −840 | −1840 | −1448 | 137 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 138(G) | −2094 | 2048 | −4883 | −4935 | −3577 | 2953 | −3965 | −3084 | −4561 | 1742 | −2783 | −3648 | −3705 | −4191 | −4306 | −2408 | −2479 | −2819 | −4182 | −3948 | 138 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −310 | −8606 | −2390 | −894 | −1115 | −701 | −1378 | * | * | | | | | | | | | | | | |
| 139(G) | −2035 | −3386 | −760 | 751 | −3993 | 2992 | −1663 | −3772 | −1503 | −3736 | −2940 | −1204 | −2871 | 1135 | −2038 | −1880 | 718 | −3272 | −3927 | −3185 | 139 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −461 | −8303 | −1886 | −894 | −1115 | −1966 | −427 | * | * | | | | | | | | | | | | |
| 140(D) | −940 | −2299 | 1878 | −180 | −2604 | −1821 | −574 | −2327 | 1163 | −2325 | 1838 | −487 | −1974 | −143 | −692 | 1766 | −894 | −1924 | −2537 | −1874 | 140 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −930 | −7851 | −1087 | −894 | −1115 | −2707 | −240 | * | * | | | | | | | | | | | | |
| 141(Q) | −938 | −2159 | −672 | −169 | −2594 | −1727 | −223 | −2242 | 616 | −2123 | −1305 | 1962 | −1829 | 2203 | 2006 | −820 | −833 | −1874 | −2189 | −1702 | 141 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −18 | −6939 | −7981 | −894 | −1115 | −3303 | −154 | * | * | | | | | | | | | | | | |
| 142(W) | −3267 | −2487 | −3870 | −3996 | 1146 | −3755 | −293 | −2351 | −3496 | −1826 | −1813 | −2554 | −3686 | −2607 | −3080 | −3042 | −3163 | −2460 | 5179 | 3293 | 142 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −18 | −6939 | −7981 | −894 | −1115 | −94 | −3981 | * | * | | | | | | | | | | | | |
| 143(K) | −1377 | −2796 | −1249 | −677 | −3147 | −515 | 1562 | −2869 | 2277 | −2795 | −1891 | −19 | 370 | −473 | 1735 | −1258 | 973 | −2437 | −2936 | −2306 | 143 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 144(F) | −1269 | −1674 | −1906 | −1343 | 2267 | 740 | −1243 | −1281 | 445 | 884 | 1381 | 644 | −2580 | 894 | −1502 | −1486 | −1208 | −1134 | −2059 | −1617 | 144 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −124 | −8606 | −3645 | −894 | −1115 | −701 | −1378 | * | * | | | | | | | | | | | | |
| 145(P) | 2399 | −2218 | −4242 | −4533 | −4827 | 1387 | −4028 | −4645 | −4562 | −4894 | −3951 | −3166 | 2828 | −4060 | −4339 | −1852 | −2073 | −3390 | −5022 | −4957 | 145 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8488 | −9530 | −894 | −1115 | −402 | −2040 | * | * | | | | | | | | | | | | |
| 146(V) | −3180 | −2691 | −5763 | −5333 | −2397 | −5475 | −4843 | 1633 | −5189 | 1010 | 2091 | −5138 | −5106 | −4711 | −5091 | −4778 | −3137 | 2910 | −4012 | −3842 | 146 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 147(P) | −5672 | −5016 | −5908 | −6280 | −6507 | −5021 | −5699 | −7438 | −6489 | −6950 | −6782 | −6096 | 4323 | −6350 | −6037 | −6019 | −5995 | −6875 | −5439 | −6461 | 147 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |

TABLE 4-continued

| | | | | | | | | | | | | | | | | | | | | | |
|---|---|---|---|---|---|---|---|---|---|---|---|---|---|---|---|---|---|---|---|---|---|
| 148(V) | −3064 | −2549 | −5744 | −5416 | −3044 | −5587 | −5526 | 2767 | −5376 | 28 | −1748 | −5243 | −5290 | −5253 | −5507 | −4963 | −3050 | 2845 | −4804 | −4365 | 148 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 149(E) | −5429 | −5227 | −3611 | 3948 | −6343 | −4680 | −4698 | −7062 | −5156 | −6644 | −6413 | −4312 | −5188 | −4740 | −5393 | −5360 | −5587 | −6630 | −5420 | −5964 | 149 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 150(V) | −3034 | −2523 | −5726 | −5424 | −3217 | −5557 | −5670 | 2853 | −5401 | −1960 | −1903 | −5240 | −5307 | −5371 | −5582 | −4951 | −3030 | 2987 | −5010 | −4474 | 150 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 151(I) | −3098 | −2584 | −5765 | −5423 | −2910 | −5595 | −5432 | 2858 | −5369 | 805 | −1628 | −5253 | −5275 | −5169 | −5457 | −4964 | −3080 | 2522 | −4655 | −4287 | 151 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 152(P) | −2100 | −2801 | −2590 | −2765 | −4693 | −2808 | −3070 | −4508 | −2721 | −4590 | −3817 | −2613 | 3846 | 1368 | −2863 | −2250 | 500 | −3643 | −4688 | −4333 | 152 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 153(W) | −246 | 982 | 39 | 198 | −144 | −596 | 928 | −456 | 289 | −954 | 709 | 281 | −285 | 575 | 131 | −180 | −17 | −477 | 1369 | 255 | 153 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 154(M) | −1341 | −1294 | −3042 | −2451 | 2731 | −39 | −1637 | −803 | −2166 | 94 | 2746 | −2223 | −2861 | 603 | −2187 | 830 | −1285 | −718 | −1726 | −1352 | 154 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 155(C) | 2726 | 3556 | −4940 | −5212 | −4865 | 1173 | −4237 | −4662 | −4867 | −4931 | −3980 | −3353 | −3349 | −4328 | −4516 | 426 | −2116 | −3416 | −5102 | −5057 | 155 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 156(W) | 196 | 1347 | −3336 | −2725 | −1130 | −2867 | 1000 | 667 | −2371 | −1106 | −459 | −2376 | −2920 | −2077 | 889 | −1936 | −1310 | −678 | 3362 | 3169 | 156 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 157(K) | 166 | −2638 | 141 | 579 | −2958 | −2143 | −801 | −2708 | 1684 | −2654 | −1728 | −778 | −2236 | 1044 | 1226 | 619 | −1108 | 845 | −2822 | −2141 | 157 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 158(Y) | 1212 | −1470 | −2316 | −1741 | 1052 | −2622 | −1397 | −1026 | 300 | −1339 | −658 | −1763 | 1264 | −1389 | 476 | −1632 | −1227 | 1091 | −1884 | 1942 | 158 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 159(V) | −2101 | −1824 | −4475 | −3923 | −2016 | −3881 | −2921 | 1555 | −3607 | 44 | −1092 | 18 | −3873 | −3304 | −3498 | −3016 | 1758 | 2629 | −2759 | −2390 | 159 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 160(I) | 972 | −1454 | −2361 | −1785 | −1451 | −2633 | −1415 | 1648 | 368 | 1218 | −644 | −1793 | −2701 | −1422 | −48 | 121 | 475 | −891 | −1875 | −1479 | 160 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 161(R) | −1557 | −2965 | −1351 | 1883 | −3340 | −504 | −1043 | −3048 | 1177 | −2952 | −2061 | 809 | −2552 | 675 | 2434 | −1431 | −1477 | −2620 | −3069 | −2464 | 161 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −254 | −8606 | −2657 | −894 | −1115 | −701 | −1378 | * | * | | | | | | | | | | | | |
| 162(R) | 903 | −2511 | 733 | 684 | −2833 | −2001 | −664 | −2583 | 1048 | −2526 | −1601 | 891 | −2099 | 1582 | 1672 | −916 | −977 | −2134 | −2692 | −2010 | 162 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8359 | −9402 | −894 | −1115 | −282 | −2492 | * | * | | | | | | | | | | | | |
| 163(L) | 145 | −1585 | −4123 | −3529 | −1544 | −3387 | −2364 | 775 | −3163 | 2487 | −687 | −3055 | −3428 | −2796 | −2997 | 41 | −1740 | 743 | −2201 | −1870 | 163 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 164(V) | 623 | −2039 | −1412 | 108 | −2154 | −2315 | −1012 | 280 | 569 | 456 | −1187 | −1099 | −2400 | 576 | 118 | 778 | −1150 | 1235 | −2361 | −1832 | 164 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |

TABLE 4-continued

| | | | | | | | | | | | | | | | | | | | | | |
|---|---|---|---|---|---|---|---|---|---|---|---|---|---|---|---|---|---|---|---|---|---|
| 165(K) | −1216 | −2691 | 495 | 1744 | −3009 | −2168 | −843 | −69 | 1908 | −2706 | −1783 | 414 | 339 | −385 | −943 | 718 | −1157 | −2312 | −2875 | −2189 | 165 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 166(L) | −1936 | −1746 | −4126 | −3499 | 807 | −3503 | −2344 | 1202 | −3118 | 2065 | 1628 | −3097 | −3473 | 1712 | 416 | −2594 | −1866 | −1010 | −2120 | −1846 | 166 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −764 | −8606 | −1291 | −894 | −1115 | −701 | −1378 | * | * | | | | | | | | | | | | |
| 167(F) | 691 | −862 | −2216 | −1632 | 1624 | −2234 | −1030 | −388 | 779 | 1008 | −53 | −1526 | 340 | −1183 | −1510 | −1269 | −765 | −290 | −1267 | 1539 | 167 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −9 | −7851 | −8893 | −894 | −1115 | −2707 | −240 | * | * | | | | | | | | | | | | |
| 168(H) | −775 | −2159 | −652 | 1820 | 958 | −1752 | 2010 | −2178 | 869 | −2157 | −1258 | −401 | −1844 | 47 | 694 | −670 | 847 | −1769 | −2349 | −1698 | 168 |
| — | −149 | −500 | 234 | 44 | −381 | 399 | 105 | −627 | 210 | −465 | −721 | 275 | 393 | 45 | 96 | 359 | 117 | −368 | −295 | −250 | |
| — | −3016 | −1080 | −1310 | −59 | −4631 | −2707 | −240 | * | * | | | | | | | | | | | | |
| 169(K) | −541 | −1272 | −806 | −243 | −1261 | −1631 | −278 | −993 | 1962 | 241 | −435 | −447 | −1715 | 16 | −261 | 651 | −475 | −788 | −1498 | 1368 | 170 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −16 | −7111 | −8154 | −894 | −1115 | −99 | −3908 | * | * | | | | | | | | | | | | |
| 170(G) | 388 | −2469 | −3206 | −3555 | −4977 | 3463 | −3801 | −4826 | −4249 | −5038 | −4124 | 688 | −3400 | −3725 | −4295 | −2031 | −2269 | −3602 | −5156 | −4941 | 171 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 171(C) | 239 | 3977 | −3406 | 371 | −4560 | 2817 | −3588 | −4292 | −3864 | −4544 | −3674 | −2915 | −3327 | −3491 | −3939 | −1950 | −2149 | −3315 | −4780 | −4534 | 172 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 172(E) | −1178 | −2643 | 222 | 2198 | −2961 | −2149 | −810 | −2709 | 1271 | −2657 | −1733 | −785 | −2244 | −351 | 406 | 253 | 392 | 577 | −2828 | −2147 | 173 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 173(C) | 1981 | 2011 | −3741 | −3203 | −1581 | −2800 | −2105 | −1042 | −2847 | −1469 | −825 | −2650 | 1660 | −2506 | −2717 | −1959 | −1483 | 1766 | −2081 | 1103 | 174 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 174(K) | −1192 | 1182 | 577 | 1872 | −2980 | −2156 | −821 | −2729 | 2052 | −2676 | −1752 | 374 | −2254 | 1044 | −912 | −1072 | −1132 | −141 | −2845 | −2163 | 175 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 175(L) | −3000 | −2617 | −5418 | −4862 | −1799 | −4884 | −3769 | 2006 | −4568 | 2395 | −719 | −4533 | −4605 | −3952 | −4324 | −4068 | −2927 | 662 | −3117 | 1709 | 176 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 176(R) | −5677 | −5058 | −5817 | −5522 | −6223 | −5022 | −4626 | −6808 | −3755 | −6307 | −5975 | −5374 | −5388 | −4598 | 4244 | −5871 | −5687 | −6494 | −5162 | −5792 | 177 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 177(M) | −1747 | −2635 | −1848 | 98 | −2811 | −2728 | −1267 | −2408 | 687 | 200 | 3892 | −1465 | −2798 | 2232 | −853 | −1743 | −1654 | −2188 | −2826 | −2358 | 178 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −79 | −8606 | −4299 | −894 | −1115 | −701 | −1378 | * | * | | | | | | | | | | | | |
| 178(G) | 922 | −2759 | 587 | 373 | −3075 | 2180 | −884 | −2829 | 383 | −2772 | −1855 | 470 | −2305 | −432 | 613 | −1143 | −1217 | −2379 | −2940 | −2247 | 179 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −1034 | −8533 | −975 | −894 | −1115 | −477 | −1829 | * | * | | | | | | | | | | | | |
| 179(G) | −790 | −1342 | −3029 | −2997 | −3043 | 2428 | −2604 | −2480 | −2911 | −2963 | −2201 | −2139 | −2429 | −2602 | −2908 | 1256 | −1178 | 2138 | −3389 | −3113 | 180 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −11 | −7657 | −8699 | −894 | −1115 | −1036 | −965 | * | * | | | | | | | | | | | | |
| 180(N) | 461 | −2422 | 1127 | 1087 | −2741 | 255 | −569 | −2493 | 973 | −2437 | −1513 | 1736 | −1998 | −111 | 780 | −820 | −885 | −2043 | −2604 | −1918 | 181 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8163 | −9206 | −894 | −1115 | −792 | −1243 | * | * | | | | | | | | | | | | |
| 181(K) | −1687 | −3170 | −887 | 367 | −3526 | 141 | −1200 | −3278 | 3100 | −3197 | −2324 | 933 | −2601 | −772 | −1257 | −55 | −1646 | −2827 | −3347 | −2656 | 182 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −94 | −8427 | −4055 | −894 | −1115 | −1600 | −578 | * | * | | | | | | | | | | | | |

TABLE 4-continued

| | | | | | | | | | | | | | | | | | | | | | |
|---|---|---|---|---|---|---|---|---|---|---|---|---|---|---|---|---|---|---|---|---|---|
| 182(C) | 1482 | 2044 | 1980 | −748 | −2923 | 825 | −1048 | −2641 | −684 | −2673 | −1786 | −989 | −2306 | −625 | 668 | 105 | −1157 | −2179 | −2898 | −2278 | 183 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −100 | −8340 | −3967 | −894 | −1115 | −1870 | −461 | * | * | | | | | | | | | | | | |
| 183(G) | −71 | −3298 | −742 | 1596 | −3878 | 2844 | −1523 | −3647 | 365 | −3594 | −2781 | −1128 | −2775 | −1140 | −1774 | −1771 | −1968 | −3153 | −3766 | −3044 | 184 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8247 | −9289 | −894 | −1115 | −928 | −1076 | * | * | | | | | | | | | | | | |
| 184(P) | −110 | −1791 | −3943 | −3559 | 992 | −2983 | −2522 | 779 | −3255 | −1495 | −1119 | −2960 | 3564 | −2915 | −3152 | −2210 | −1838 | −1020 | −2439 | −1945 | 185 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8427 | −9469 | −894 | −1115 | −333 | −2277 | * | * | | | | | | | | | | | | |
| 185(V) | −324 | −1581 | −4163 | −3574 | 1465 | −3444 | −2271 | 858 | −3201 | −1285 | −779 | −3069 | −3463 | −2829 | −3021 | −2550 | −1757 | 2742 | −2054 | 2219 | 186 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 186(V) | −3012 | −2513 | −5669 | −5326 | 736 | −5459 | −5193 | 2647 | −5256 | −1783 | −1738 | −5111 | −5200 | −5109 | −5353 | −4805 | −2998 | 2946 | −4562 | −4059 | 187 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 187(T) | −1742 | −2352 | −4396 | −4706 | −4890 | −2611 | −4150 | −4724 | −4630 | −4997 | −4079 | −3309 | −3413 | −4199 | −4395 | 385 | 3854 | −3505 | −5101 | −4993 | 188 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 188(D) | −5403 | −5247 | 4201 | −3898 | −6360 | −4647 | −4682 | −7143 | −5306 | −6710 | −6481 | −4228 | −5165 | −4724 | −5628 | −5311 | −5571 | −6677 | −5444 | −5968 | 189 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 189(N) | −1971 | −2698 | −2354 | −2707 | −4989 | 227 | −3384 | −4887 | −3747 | −5029 | −4165 | 4036 | −3410 | −3211 | −4065 | 339 | −2390 | −3740 | −5140 | −4724 | 190 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 190(G) | −1970 | −3190 | −1651 | −1272 | −3823 | 2887 | −1466 | −3495 | 690 | −3390 | −2549 | 837 | −2933 | −1041 | 348 | 520 | −1935 | −3053 | −3480 | −2950 | 191 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 191(N) | −3572 | −4363 | −2064 | −2403 | −3700 | −3611 | 1730 | −5474 | −3143 | −5200 | −4750 | 4219 | −4166 | −2994 | −3470 | −3447 | −3764 | −4934 | −4032 | −3152 | 192 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 192(Y) | −2601 | −2317 | −4832 | −4277 | 2774 | −4169 | −2557 | −1161 | −3899 | 976 | 1646 | −3718 | −4055 | −3312 | −3626 | −3291 | −2522 | 912 | −2037 | 2952 | 193 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 193(I) | −3062 | −2579 | −5722 | −5432 | −3070 | −5435 | −5500 | 3834 | −5371 | −1812 | −1799 | −5204 | −5248 | −5259 | −5489 | −4839 | −3069 | 763 | −4808 | −4338 | 194 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 194(I) | 887 | −2367 | −5400 | −4982 | −2747 | −5034 | −4493 | 2447 | −4817 | 1065 | −1570 | −4691 | −4862 | −4594 | −4817 | −4295 | −2785 | 2222 | −4070 | −3675 | 195 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 195(D) | −5403 | −5247 | 4201 | −3898 | −6360 | −4647 | −4682 | −7143 | −5306 | −6710 | −6481 | −4228 | −5165 | −4724 | −5628 | −5311 | −5571 | −6677 | −5444 | −5968 | 196 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 196(W) | 1374 | 1831 | −3697 | −3062 | 844 | −2906 | −1776 | −647 | −2659 | 765 | 1206 | −2550 | −2953 | −2280 | −2460 | −1991 | −1296 | 1458 | 3242 | −1297 | 197 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −110 | −8606 | −3817 | −894 | −1115 | −701 | −1378 | * | * | | | | | | | | | | | | |
| 197(Y) | −1155 | −2581 | 629 | −465 | 498 | −2127 | 2018 | −2629 | 1786 | −2586 | −1675 | −768 | −2218 | 1110 | 633 | −1041 | −1091 | −2200 | −2747 | 2249 | 198 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8502 | −9544 | −894 | −1115 | −422 | −1978 | * | * | | | | | | | | | | | | |
| 198(F) | −2529 | −2378 | −4709 | −4312 | 3957 | 634 | −2487 | −1330 | −3952 | −208 | −1164 | −3613 | −4025 | −3430 | −3724 | −3098 | −2553 | 37 | −1994 | −1161 | 199 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |

TABLE 4-continued

| | | | | | | | | | | | | | | | | | | | | | |
|---|---|---|---|---|---|---|---|---|---|---|---|---|---|---|---|---|---|---|---|---|---|
| 199(M) | 167 | −2600 | 543 | 1350 | −2902 | 752 | −812 | −2640 | −400 | −1391 | 2204 | −793 | 865 | 697 | −905 | −1060 | 393 | −2212 | −2794 | −2123 | 200 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −115 | −8606 | −3756 | −894 | −1115 | −701 | −1378 | * | * | | | | | | | | | | | | |
| 200(E) | −1224 | −2674 | −1052 | 1892 | −3010 | −2175 | −811 | −2747 | 1260 | −2681 | −1766 | 736 | 426 | −355 | 1729 | −1102 | 795 | −2306 | −2834 | −2176 | 201 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −279 | −8497 | −2532 | −894 | −1115 | −415 | −2000 | * | * | | | | | | | | | | | | |
| 201(I) | −1660 | −2384 | 1157 | −1375 | −2958 | −2441 | −1854 | 2571 | −1864 | −2787 | −2075 | −1563 | 2045 | −1604 | −2319 | 1056 | −1780 | −2140 | −3245 | −2715 | 202 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8357 | −9399 | −894 | −1115 | −280 | −2501 | * | * | | | | | | | | | | | | |
| 202(I) | 196 | −1230 | 1001 | −2733 | −1199 | −45 | −1718 | 2445 | −2404 | −65 | 1177 | −2387 | −2913 | −2094 | −2330 | −1931 | 133 | 622 | −1697 | −1345 | 203 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 203(W) | −246 | 982 | 39 | 198 | −144 | −596 | 928 | −456 | 289 | −954 | 709 | 281 | −285 | 575 | 131 | −180 | −17 | −477 | 1369 | 255 | 204 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 204(D) | −1192 | −2666 | 1987 | −479 | −2987 | 905 | 1522 | −2738 | 930 | −2681 | −1756 | 453 | −2253 | 1000 | 618 | 271 | −1131 | −2288 | −2848 | −2165 | 205 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 205(D) | 433 | −4013 | 3168 | −1096 | −4558 | −2754 | −2037 | −4393 | 494 | −4319 | −3549 | −1451 | 2098 | −1679 | −2685 | −2287 | −2573 | −3858 | −4503 | −3661 | 206 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 206(W) | −161 | −1534 | 335 | −1559 | −1543 | −2564 | −1329 | 1049 | 30 | 1134 | −717 | −1634 | 1219 | −1254 | −1672 | −251 | −1207 | −980 | 3174 | −1526 | 207 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −596 | −8606 | −1574 | −894 | −1115 | −701 | −1378 | * | * | | | | | | | | | | | | |
| 207(E) | −832 | −2017 | −804 | 1137 | 888 | −167 | −525 | −1912 | −156 | 672 | −1136 | −542 | −1944 | 1015 | 975 | 594 | −771 | −1582 | −2267 | −1657 | 208 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8018 | −9061 | −894 | −1115 | −169 | −3177 | * | * | | | | | | | | | | | | |
| 208(E) | 1587 | −2677 | 450 | 1606 | −2995 | −113 | −834 | −2745 | 1329 | −2692 | −1769 | −797 | −2264 | 736 | −931 | −1084 | −1146 | −505 | −2862 | −2177 | 209 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 209(M) | 902 | −1495 | −4062 | −3447 | −1420 | −3322 | −2227 | 824 | −3067 | 1877 | 1985 | −2965 | −3339 | −2688 | −2882 | −2422 | 401 | 1163 | −2053 | −1722 | 210 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 210(H) | 166 | 1605 | −1017 | 1752 | −2953 | −472 | 2332 | −2700 | −396 | −2651 | −1729 | 778 | −2244 | 1043 | −903 | 884 | −1116 | −2256 | −2824 | −2145 | 211 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 211(R) | −1176 | −2646 | 827 | 301 | −2967 | −2147 | −805 | −80 | 1073 | −2661 | −1735 | 563 | −2241 | 1045 | 2046 | −1056 | 1141 | −2268 | −2828 | −2147 | 212 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 212(A) | 1952 | −3041 | 678 | 1917 | −3353 | −2343 | −1113 | −3113 | −750 | −3050 | −2149 | −969 | −2516 | 694 | 1371 | −1391 | −1488 | −2661 | −3218 | −2511 | 213 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 213(I) | −3825 | −3264 | −6294 | −5832 | −1978 | −6067 | −5109 | 3360 | −5658 | 1823 | −758 | −5806 | −5367 | −4721 | −5322 | −5478 | −3736 | −1069 | −3777 | −3839 | 214 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 214(N) | 163 | −2644 | −1060 | 601 | −2943 | −2203 | −876 | −2672 | 1749 | 818 | −1747 | 2118 | −2306 | −428 | −951 | −94 | −1183 | −2255 | −2843 | −2180 | 215 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 215(M) | 930 | −2497 | −1084 | 530 | −2758 | −478 | 1513 | −2468 | −445 | −431 | 2199 | 1436 | −2265 | −400 | 831 | −1086 | 329 | −2086 | −2717 | −2072 | 216 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |

TABLE 4-continued

| | | | | | | | | | | | | | | | | | | | | | |
|---|---|---|---|---|---|---|---|---|---|---|---|---|---|---|---|---|---|---|---|---|---|
| 216(I) | −2915 | −2559 | −5312 | −4739 | 419 | −4739 | −3640 | 2978 | −4429 | 1485 | −658 | −4398 | −4492 | −3823 | −4183 | −3909 | 1278 | −945 | −3034 | −2864 | 217 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 217(P) | −2026 | −3159 | 379 | 213 | −3504 | −2622 | −1735 | −3127 | −1640 | −3292 | −2523 | −1378 | 3319 | −1389 | −2203 | −1939 | 401 | 1113 | −3628 | −2966 | 218 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 218(G) | −5249 | −4846 | −5805 | −6182 | −6521 | 3848 | −5650 | −7348 | −6455 | −6931 | −6666 | −5891 | −5413 | −6249 | −6011 | −5566 | −5614 | −6629 | −5452 | −6497 | 219 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 219(V) | −3032 | −2527 | −5721 | −5421 | −3204 | −5529 | −5639 | 1784 | −5391 | −1952 | −1897 | −5227 | −5294 | −5354 | −5564 | −4924 | −3030 | 3491 | −4985 | −4454 | 220 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 220(V) | −3030 | −2536 | −5710 | −5416 | −3180 | −5472 | −5582 | 1076 | −5374 | −1935 | −1886 | −5203 | −5268 | −5323 | −5532 | −4869 | −3033 | 3633 | −4937 | −4415 | 221 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 221(E) | −2882 | −4737 | 2030 | 2984 | −4984 | 228 | −2195 | −4903 | −2430 | −4775 | −4093 | −1445 | −3371 | −1861 | −3280 | −2557 | 969 | −4364 | −4971 | −3962 | 222 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 222(H) | −1683 | −2273 | −2111 | −1867 | −2720 | −2639 | 3757 | −2371 | −1792 | −2658 | −1938 | 1501 | −3000 | −1752 | −2087 | −1842 | 2262 | 788 | −3026 | −2524 | 223 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 223(G) | −5249 | −4846 | −5805 | −6182 | −6521 | 3848 | −5650 | −7348 | −6455 | −6931 | −6666 | −5891 | −5413 | −6249 | −6011 | −5566 | −5614 | −6629 | −5452 | −6497 | 224 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 224(L) | −4228 | −3609 | −6619 | −6031 | −1718 | −6422 | −5067 | 1928 | −5834 | 2739 | 2160 | −6148 | −5413 | −4568 | −5301 | −5805 | −4066 | −1850 | −3556 | −3790 | 225 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 225(F) | −5765 | −4802 | −5973 | −6324 | 4566 | −5247 | −3479 | −5215 | −6252 | −4532 | −4649 | −5413 | −5556 | −5531 | −5699 | −5820 | −5855 | −5401 | −2775 | −1729 | 226 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 226(I) | 1157 | −1932 | −4694 | −4157 | −2139 | −4088 | −3174 | 2444 | −3853 | 1087 | −1173 | −3737 | −4056 | −3545 | −3737 | −3239 | 274 | 1490 | −2964 | −2597 | 227 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 227(N) | −2483 | −4204 | 2225 | −949 | −4447 | 1738 | 1247 | −4291 | 368 | −4189 | −3400 | 2585 | −3142 | −1499 | −2517 | −2222 | −2498 | −3801 | −4368 | −3498 | 228 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 228(M) | −1382 | 1927 | −3453 | −2835 | −1221 | −2902 | −1767 | 605 | −2456 | −1083 | 4041 | 563 | −2955 | −2160 | 886 | −1979 | −1325 | 534 | −1727 | −1378 | 229 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −110 | −8606 | −3817 | −894 | −1115 | −701 | −1378 | * | * | | | | | | | | | | | | |
| 229(A) | 2906 | −2083 | −4487 | −4519 | −4043 | 938 | −3724 | −3504 | −4244 | −3982 | −3187 | −3127 | −3222 | −3819 | −4050 | −1810 | 662 | 1124 | −4390 | −4200 | 230 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −119 | −8502 | −3713 | −894 | −1115 | −1301 | −751 | * | * | | | | | | | | | | | | |
| 230(T) | 706 | −2744 | 1325 | 778 | −3067 | −2123 | −875 | −2825 | −511 | −2772 | −1862 | 917 | −2277 | −429 | −1037 | 1284 | 1668 | −2373 | −2946 | −2245 | 231 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8390 | −9432 | −894 | −1115 | −303 | −2401 | * | * | | | | | | | | | | | | |
| 231(D) | 167 | −2635 | 1868 | 326 | −2949 | −2152 | −812 | −2695 | 1328 | −2647 | −1726 | −790 | −2246 | −355 | 1297 | −1063 | 667 | 565 | −2821 | −2144 | 232 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 232(V) | 1394 | 1436 | −3993 | −3393 | −1546 | −3328 | −2258 | 780 | 34 | −283 | −724 | −2947 | −3357 | −2697 | −2889 | −2428 | −1644 | 2625 | −2136 | −1782 | 233 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |

TABLE 4-continued

| | | | | | | | | | | | | | | | | | | | | | |
|---|---|---|---|---|---|---|---|---|---|---|---|---|---|---|---|---|---|---|---|---|---|
| 233(I) | −64 | −1380 | −3936 | −3314 | 897 | −3170 | −2054 | 2138 | −2923 | 748 | −513 | −2814 | −3199 | −2543 | −2730 | −2264 | −1521 | 1564 | −1889 | 2035 | 234 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 234(I) | −3298 | −2830 | −5797 | −5296 | 2411 | −5417 | −4467 | 2599 | −5083 | 1361 | −849 | −5082 | −4994 | −4412 | −4856 | −4676 | −3229 | 1167 | −3586 | −3484 | 235 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 235(A) | 2357 | −1657 | −3565 | −3090 | −2055 | 1061 | −2318 | 320 | −2816 | −1937 | −1269 | −2605 | −3060 | −2533 | −2815 | 181 | 162 | 1115 | −2519 | −2176 | 236 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 236(G) | −1411 | −2759 | 621 | −646 | −3014 | 2511 | −1040 | −2740 | 599 | −2751 | 1397 | 824 | −2446 | −612 | −1184 | −1304 | −1359 | −2353 | −2972 | 957 | 237 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 237(T) | −165 | −2638 | −1015 | 1030 | −2958 | −2143 | 1459 | −2707 | 910 | −2654 | −1728 | −779 | 232 | 1044 | −889 | 939 | 1752 | −2260 | −2822 | −2141 | 238 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 238(D) | 479 | −2473 | 2115 | −550 | 1083 | −2181 | −848 | −2428 | 582 | −917 | −1581 | −847 | 430 | −414 | 489 | −1095 | 719 | −2058 | −2700 | −2062 | 239 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 239(G) | −2879 | −4746 | 721 | 1167 | −4951 | 2971 | −2158 | −4854 | 1286 | −4718 | −4028 | −1440 | −3363 | −1819 | −3088 | −2550 | −2935 | −4334 | −4900 | −3920 | 240 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −473 | −8606 | −1853 | −894 | −1115 | −701 | −1378 | * | * | | | | | | | | | | | | |
| 240(G) | −1227 | −1852 | −3756 | −3959 | −4398 | 2730 | −3546 | −4201 | −3968 | −4445 | −3506 | −2737 | −2897 | −3530 | −3833 | 2223 | 1011 | −2989 | −4607 | −4484 | 241 |
| — | −149 | −500 | 233 | 43 | −381 | 399 | 106 | −626 | 210 | −466 | −720 | 275 | 394 | 45 | 96 | 359 | 117 | −367 | −294 | −249 | |
| — | −3305 | −3226 | −336 | −186 | −3046 | −522 | −1719 | * | * | | | | | | | | | | | | |
| 241(V) | −1770 | −1399 | −4112 | −3687 | −1148 | −3723 | −3023 | 861 | −3415 | 1359 | −31 | −3414 | −3586 | −3084 | −3351 | −2991 | −1753 | 2970 | −2514 | −2209 | 243 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −16 | −7111 | −8154 | −894 | −1115 | −3231 | −162 | * | * | | | | | | | | | | | | |
| 242(T) | −557 | −1464 | −843 | −435 | −2244 | −1466 | −609 | −1894 | 1229 | −2001 | −1185 | −581 | −1777 | −240 | −466 | 926 | 2568 | −1473 | −2261 | −1748 | 244 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −16 | −7111 | −8154 | −894 | −1115 | −99 | −3908 | * | * | | | | | | | | | | | | |
| 243(V) | −408 | −2431 | −5505 | −5112 | −2823 | −5182 | −4753 | 815 | −4976 | 778 | −1612 | −4848 | −4983 | −4770 | −5004 | −4472 | −2871 | 3288 | −4262 | −3865 | 245 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 244(K) | −1565 | −2981 | −1249 | 1228 | −3334 | −2441 | −1073 | 161 | 2733 | −2970 | −2082 | 1556 | −2556 | 666 | −900 | −1437 | −1493 | −2624 | −3105 | −2480 | 246 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 245(E) | −1173 | −2544 | 125 | 1854 | −2824 | −2162 | −826 | −333 | 1224 | −2542 | 1322 | 360 | −2255 | −380 | −923 | −1073 | 1352 | 44 | −2752 | −2095 | 247 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 246(R) | −1290 | −1660 | −1984 | −32 | 727 | −2538 | −1272 | 1093 | 1325 | 948 | −835 | −1531 | −2610 | −1123 | 1480 | −1524 | 488 | −1115 | −2049 | −1618 | 248 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −208 | −8606 | −2925 | −894 | −1115 | −701 | −1378 | * | * | | | | | | | | | | | | |
| 247(E) | −1098 | −1699 | −1503 | 1952 | 268 | −2269 | 1109 | −1360 | 530 | −133 | −863 | −1141 | −24 | −732 | −1212 | −1227 | −1038 | 1039 | −2055 | 1060 | 249 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −191 | −8405 | −3045 | −894 | −1115 | −1676 | −541 | * | * | | | | | | | | | | | | |
| 248(K) | −1097 | −2546 | −884 | 806 | −2885 | −253 | −671 | −2620 | 2294 | −2551 | −1640 | 1584 | 527 | −216 | 815 | −973 | −1030 | −2180 | −2700 | −2045 | 250 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −1438 | −8221 | −672 | −894 | −1115 | −2153 | −367 | * | * | | | | | | | | | | | | |
| 249(P) | −253 | −917 | −1409 | −1421 | −2656 | −1084 | −1555 | −2458 | −1537 | −2662 | −1851 | −1108 | 2981 | −1371 | −1743 | 1948 | −614 | −1671 | −2835 | −2454 | 251 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −19 | −6802 | −7844 | −894 | −1115 | −3353 | −149 | * | * | | | | | | | | | | | | |

TABLE 4-continued

| | | | | | | | | | | | | | | | | | | | | | |
|---|---|---|---|---|---|---|---|---|---|---|---|---|---|---|---|---|---|---|---|---|---|
| 250(K) | −1150 | −1622 | −1430 | −946 | 2379 | −2053 | −469 | −1244 | 2591 | −1236 | −778 | −999 | −2179 | −474 | −282 | −1235 | −1092 | −1159 | −986 | −123 | 252 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −19 | −6802 | −7844 | −894 | −1115 | −3353 | −149 | * | * | | | | | | | | | | | | |
| 251(C) | −933 | 3622 | −1652 | −1088 | −2158 | −1769 | −787 | −1664 | 2742 | −1895 | −1231 | −1066 | −2061 | −487 | −80 | −1053 | −994 | −1392 | −2119 | −1779 | 253 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −490 | −6802 | −1841 | −894 | −1115 | −3353 | −149 | * | * | | | | | | | | | | | | |
| 252(H) | −1687 | −1933 | −1269 | −1292 | −876 | −1925 | 4894 | −2432 | −968 | −2285 | −1898 | −1353 | −2307 | −1191 | −1079 | −1732 | −1775 | −2223 | −1258 | −443 | 254 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −27 | −6339 | −7381 | −894 | −1115 | −83 | −4158 | * | * | | | | | | | | | | | | |
| 253(W) | −246 | 982 | 39 | 198 | −144 | −596 | 928 | −456 | 289 | −954 | 709 | 281 | −285 | 575 | 131 | −180 | −17 | −477 | 1369 | 255 | 255 |
| — | * | * | * | * | * | * | * | * | * | * | * | * | * | * | * | * | * | * | * | * | |
| — | * | * | * | * | * | * | * | * | 0 | | | | | | | | | | | | |

[1]Program name and version
[2]Name of the input sequence alignment file
[3]Length of the alignment: include indels
[4]Type of residues
[5]Map of the match states to the columns of the alignment
[6]Commands used to generate the file: this one means that hmmbuild (default parameters) was applied to the alignment file
[7]Commands used to generate the file: this one means that hmmcalibrate (default parameters) was pplied to the hmm profile
[8]Number of sequences in the alignment
[9]When the file was generated
[10]The trasition probability distribution for the null model (single G state).
[11]The symbol emission probability distribution for the null model (G tate); consists of K integers. The null probability used to convert these back to model probabilities is 1/K.
[12]The extreme value distribution parameters μ and lambda respectively, both floating point values. Lambda is positive and nonzero. These values are set when the model is calibrated with hmmcalibrate.

TABLE 5

HMMER2.0 [2.2 g][1]
NAME rpiB__exp__ver__seqs[2]
LENG 165[3]
ALPH Amino[4]
MAP yes[5]
COM /app/public/hmmer/current/bin/hmmbuild rpiB__exp__ver__seqs__hmm.txt rpiB__exp__ver__seqs.aln[6]
COM /app/public/hmmer/current/bin/hmmcalibrate rpiB__exp__ver__seqs__hmm.txt[7]
NSEQ 5[8]
DATE Fri Jan 15 15:09:54 2010[9]
XT −8455 −4 −1000 −1000 −8455 −4 −8455 −4
NULT −4 −8455[10]
NULE 595 −1558 85 338 −294 453 −1158 197 249 902 −1085 −142 −21 −313 45 531 201 384 −1998 −644[11]
EVD −148.871582 0.171732[12]

| HMM | A m->m | C m->i | D m->d | E i->m | F i->i | G d->m | H d->d | I b->m | K m->e | L | M | N | P | Q | R | S | T | V | W | Y | |
|---|---|---|---|---|---|---|---|---|---|---|---|---|---|---|---|---|---|---|---|---|---|
| | −419 | * | −1988 | | | | | | | | | | | | | | | | | | |
| 1(M) | −472 | −717 | −1869 | −1452 | −811 | −1641 | −1064 | −19 | −1120 | −236 | 3221 | −1271 | −1953 | −1041 | −1252 | −839 | 2183 | 1 | −1479 | −1107 | 2 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −21 | −6654 | −7696 | −894 | −1115 | −701 | −1378 | −419 | * | | | | | | | | | | | | |
| 2(M) | −2287 | −2928 | −2934 | −1749 | −3481 | −2960 | −972 | −2902 | 1739 | −2718 | 4133 | −1682 | −2923 | −571 | 1989 | −2235 | −2032 | −2713 | −2754 | −2576 | 3 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 3(K) | −2781 | −3365 | −3640 | −2094 | −4305 | −3231 | −1066 | −3573 | 2986 | −3184 | −2538 | −1924 | −3155 | −648 | 2884 | −2655 | −2421 | −3365 | −2984 | −2940 | 4 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 4(I) | −2263 | −1773 | −4916 | −4590 | −2357 | −4691 | −4606 | 3030 | −4519 | −1143 | −1083 | −4377 | −4471 | −4430 | −4645 | −4052 | −2257 | 2655 | −4021 | −3534 | 5 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 5(A) | 2619 | −1481 | −2444 | −2313 | −2177 | 1153 | −2030 | −2304 | −2293 | −2564 | −1847 | −1910 | −2487 | −2076 | −2443 | −1192 | −1254 | −1841 | −2615 | 2482 | 6 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 6(I) | −2774 | −2311 | −5139 | −4595 | 1840 | −4727 | −3407 | 2972 | −4331 | 1551 | 119 | −4360 | −4226 | −3490 | −3999 | −3964 | −2674 | −548 | −2467 | −2263 | 7 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 7(G) | 1350 | −1652 | −3252 | −3534 | −4099 | 3322 | −3254 | −3906 | −3698 | −4170 | −3287 | −2477 | −2669 | −3270 | −3561 | −1294 | −1510 | −2764 | −4228 | −4163 | 8 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 8(C) | 1570 | 3123 | −3455 | −3312 | −3254 | −1715 | −2747 | −2919 | −3065 | −3214 | −2387 | −2245 | −2443 | −2739 | −3031 | 2159 | 1698 | −2142 | −3556 | −3325 | 9 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 9(D) | −3832 | −4189 | 4132 | −2236 | −5073 | −3341 | −3194 | −5633 | −3716 | −5365 | −5035 | −2584 | −3886 | −3102 | −4252 | −3662 | −4000 | −5151 | −4434 | −4544 | 10 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 10(H) | −4406 | −3961 | −3921 | −4171 | −3231 | −3926 | 5401 | −5468 | −3992 | −5013 | −4849 | −4130 | −4378 | −4151 | −3893 | −4548 | −4592 | −5195 | −3383 | −2818 | 11 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 11(A) | 2232 | −1337 | −2891 | −2645 | −2759 | 1179 | −2300 | −2305 | −2493 | −2664 | −1899 | −2011 | 1727 | −2245 | −2597 | −1053 | −1133 | 1237 | −3096 | −2784 | 12 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |

TABLE 5-continued

| | | | | | | | | | | | | | | | | | | | | | |
|---|---|---|---|---|---|---|---|---|---|---|---|---|---|---|---|---|---|---|---|---|---|
| 12(G) | 2269 | −1609 | −3303 | −3564 | −4060 | 2898 | −3234 | −3854 | −3677 | −4122 | −3232 | −2458 | −2636 | −3249 | −3536 | −1251 | −1465 | −2716 | −4208 | −4132 | 13 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 13(F) | −4359 | −3340 | −4801 | −5125 | 3666 | −4673 | −926 | −3244 | −4690 | −2579 | −2662 | −3327 | −4543 | −3457 | −4080 | −3933 | −4223 | −3407 | −176 | 3618 | 14 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 14(E) | 965 | −2018 | −563 | 2095 | −2270 | −1792 | −601 | 929 | −298 | −2028 | −1213 | 1466 | −1964 | −210 | −785 | −835 | −853 | −1562 | −2346 | −1732 | 15 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 15(L) | −3127 | −2591 | −5490 | −4969 | −1050 | −5210 | −4048 | 1779 | −4718 | 2845 | 153 | −4922 | −4503 | −3743 | −4335 | −4557 | −3016 | −680 | −2794 | −2870 | 16 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 16(K) | −2564 | −3293 | −2444 | −1757 | −3636 | −3006 | 2839 | −3540 | 3410 | −3227 | −2573 | −1757 | −3072 | −792 | 63 | −2440 | −2332 | −3283 | −2943 | −2641 | 17 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 17(H) | −1148 | −2512 | −855 | 2058 | −2902 | −1994 | 2342 | −2591 | 128 | −2483 | −1616 | −631 | −2097 | 2016 | 1481 | −1018 | −1059 | −2181 | −2581 | −2010 | 18 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 18(E) | −1214 | −2568 | −920 | 1972 | −2983 | −2045 | −586 | −2657 | 1514 | −2533 | −1673 | 1657 | −2146 | −144 | 1763 | −1082 | −1120 | −2249 | −2617 | −2066 | 19 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 19(I) | −2331 | −1850 | −4929 | −4526 | −1878 | −4657 | −4155 | 3087 | −4395 | 1092 | −653 | −4313 | −4359 | −4061 | −4374 | −3964 | −2301 | 1795 | −3455 | −3176 | 20 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 20(I) | 861 | −1151 | −2952 | −2395 | −1325 | −2834 | −1796 | 2510 | 1055 | −897 | −419 | −2235 | −2881 | −1930 | −2158 | −1929 | −1221 | 1545 | −1966 | −1583 | 21 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 21(N) | 813 | −2381 | 1347 | 1507 | −2662 | −1747 | −535 | −2406 | −208 | 412 | −1497 | 1534 | −1926 | −103 | −741 | −801 | −890 | −1984 | −2583 | −1885 | 22 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 22(H) | −4309 | −3316 | −4750 | −5034 | 2322 | −4652 | 3920 | −3257 | −4598 | −2616 | −2676 | −3292 | −4519 | −3412 | −4025 | −3892 | −4169 | −3395 | −160 | 3563 | 23 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 23(L) | −2786 | −2345 | −5148 | −4683 | −1172 | −4726 | −3816 | −28 | −4406 | 2803 | 4 | −4494 | −4312 | −3662 | −4132 | −4048 | −2728 | 1578 | −2811 | −2770 | 24 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 24(K) | −1571 | −1746 | −2549 | −1867 | −1651 | −2808 | −1423 | −501 | 2816 | 816 | −659 | −1866 | −2843 | −1214 | −884 | −1932 | −1496 | 1278 | −2219 | −1867 | 25 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 25(E) | −1094 | −2562 | −460 | 2079 | −2899 | 820 | −601 | −2638 | 1360 | −2558 | −1677 | −487 | −2036 | 2006 | −576 | −944 | −1037 | −2199 | −2703 | −2035 | 26 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 26(R) | 981 | −2341 | −1267 | −620 | −2805 | −2102 | −629 | −2433 | 1534 | −2379 | −1549 | −826 | −2190 | −201 | 2293 | −1120 | 1445 | −2071 | −2505 | −2019 | 27 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 27(G) | −3681 | −3593 | −4389 | −4747 | −5281 | 3812 | −4419 | −5908 | −5071 | −5671 | −5288 | −4417 | −4223 | −4850 | −4766 | −3952 | −4069 | −5125 | −4424 | −5214 | 28 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 28(H) | −792 | −959 | 1170 | −1245 | −823 | −2121 | 2520 | 1243 | −1075 | −814 | −148 | −1260 | −2191 | −907 | −1300 | −1141 | −732 | 1120 | −1278 | 1776 | 29 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |

TABLE 5-continued

| | | | | | | | | | | | | | | | | | | | | | |
|---|---|---|---|---|---|---|---|---|---|---|---|---|---|---|---|---|---|---|---|---|---|
| 29(E) | −3777 | −4125 | −1925 | 3871 | −4984 | −3355 | −3125 | −5379 | −3371 | −5156 | −4796 | −2611 | −3875 | −3007 | −3762 | −3630 | −3916 | −4960 | −4357 | −4463 | 30 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 30(V) | −1398 | −1296 | −3505 | −3062 | 1915 | −2838 | −1891 | −110 | −2753 | −806 | −463 | −2576 | 1648 | −2415 | −2655 | −2024 | −1427 | 2666 | −1672 | −1059 | 31 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 31(I) | −1903 | −1575 | −3829 | 1002 | −1980 | −3856 | −3129 | 3048 | −3318 | −1074 | −865 | −3323 | −3801 | −3173 | −3427 | −3072 | −1882 | 1884 | −3087 | −2660 | 32 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 32(D) | −2621 | −3795 | 3681 | −1030 | −4598 | −2524 | −2159 | −4724 | −2532 | −4603 | −4039 | −1389 | 1844 | −1902 | −3313 | −2398 | −2792 | −4123 | −4387 | −3801 | 33 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 33(C) | −773 | 2902 | −2248 | −1657 | 1518 | −2191 | 2246 | −300 | 952 | −640 | 16 | −1516 | −2253 | −1171 | −1445 | −1236 | −714 | 1306 | −1177 | −767 | 34 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −955 | −7714 | −1061 | −894 | −1115 | −701 | −1378 | * | * | | | | | | | | | | | | |
| 34(Y) | −1203 | −1551 | −1601 | −1557 | −258 | 2328 | −891 | −1846 | −1574 | −1893 | −1401 | −1430 | −2354 | −1422 | −1739 | −1353 | −1362 | −1612 | −847 | 3352 | 35 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −730 | −6778 | −1366 | −894 | −1115 | −2238 | −344 | * | * | | | | | | | | | | | | |
| 35(C) | −663 | 5232 | −2426 | −2431 | −1699 | −1297 | −1762 | −1061 | −2104 | −1610 | −1264 | −1804 | −1878 | −2021 | −1984 | −989 | −985 | −841 | −1907 | −1755 | 36 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −32 | −6081 | −7123 | −894 | −1115 | −158 | −3266 | * | * | | | | | | | | | | | | |
| 36(G) | 1599 | −1639 | −3268 | −3545 | −4089 | 3241 | −3249 | −3891 | −3693 | −4156 | −3271 | −2471 | −2659 | −3265 | −3555 | −1280 | −1496 | −2750 | −4224 | −4155 | 37 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 37(T) | −1019 | −1350 | −2595 | −2259 | −1755 | −2104 | −1851 | −1170 | −1982 | 1053 | −902 | −1947 | 1595 | −1859 | −2088 | −1345 | 2793 | −1049 | −2315 | −1957 | 38 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 38(W) | −1523 | −2432 | −1718 | −981 | −1961 | −2421 | 2452 | −2353 | 1666 | −2305 | −1571 | −1119 | −2450 | −391 | 1874 | −1468 | −1390 | −2096 | 3160 | 1968 | 39 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 39(Y) | −801 | −1431 | −1812 | −1432 | −2222 | 1018 | −1440 | −1940 | −1356 | −2172 | −1405 | −1370 | −2236 | −1227 | −1679 | 1947 | 1518 | −1551 | −2514 | 2318 | 40 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 40(D) | 993 | −2671 | 1719 | 1380 | −2973 | −1806 | −685 | −2750 | −415 | −2688 | −1805 | 1577 | −2046 | −259 | −980 | 940 | −1098 | −2291 | −2865 | −2121 | 41 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 41(E) | 1369 | −2816 | −578 | 3247 | −3818 | −2111 | −1670 | −3542 | −1674 | −3640 | −2924 | −1089 | −2643 | −1355 | −2219 | −1656 | −1910 | −2993 | −3818 | −3150 | 42 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 42(S) | −1288 | −2617 | 1789 | −359 | −3169 | −1909 | −949 | −2942 | −644 | −2904 | −2059 | −665 | −2229 | −549 | 1402 | 2434 | −1313 | −2461 | −3069 | −2377 | 43 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 43(V) | −1245 | −1672 | 1692 | −1380 | −2213 | −2223 | −1686 | −699 | −1737 | −1812 | −1281 | −1489 | −2602 | −1501 | −2109 | −1506 | 1297 | 2691 | −2717 | −2237 | 44 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 44(D) | −3832 | −4189 | 4132 | −2236 | −5073 | −3341 | −3194 | −5633 | −3716 | −5365 | −5035 | −2584 | −3886 | −3102 | −4252 | −3662 | −4000 | −5151 | −4434 | −4544 | 45 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 45(Y) | −4444 | −3646 | −4593 | −4892 | −509 | −4268 | −1873 | −3993 | −4663 | −3407 | −3460 | −3884 | −4503 | −3998 | −4255 | −4336 | −4491 | −4072 | −1177 | 4829 | 46 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |

TABLE 5-continued

| | | | | | | | | | | | | | | | | | | | | | |
|---|---|---|---|---|---|---|---|---|---|---|---|---|---|---|---|---|---|---|---|---|---|
| 46(P) | −4077 | −3791 | −4518 | −4858 | −5206 | −3818 | −4460 | −5898 | −5053 | −5602 | −5343 | −4628 | 4289 | −4938 | −4749 | −4364 | −4429 | −5313 | −4385 | −5119 | 47 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 47(D) | 1266 | −3140 | 3058 | −355 | −3519 | −2003 | 2575 | −3420 | −1274 | −3394 | −2630 | −706 | −2453 | −912 | −1929 | −1507 | −1766 | −2938 | −3557 | −2729 | 48 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 48(F) | −4356 | −3339 | −4801 | −5124 | 3760 | −4672 | −927 | −3241 | −4689 | −2576 | −2659 | −3327 | −4542 | −3456 | −4079 | −3933 | −4221 | −3405 | −176 | 3484 | 49 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 49(C) | 2748 | 3507 | −3864 | −4003 | −3721 | 1287 | −3190 | −3417 | −3713 | −3737 | −2859 | −2448 | −2504 | −3263 | −3472 | −1075 | −1267 | −2408 | −3992 | −3869 | 50 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 50(W) | −116 | 672 | 45 | 325 | −317 | −673 | 804 | −480 | 420 | −880 | 565 | 301 | −446 | 634 | 168 | −75 | 58 | −423 | 1003 | 81 | 51 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 51(S) | −865 | −1103 | −1784 | −1210 | −1118 | −2152 | −924 | 1475 | 1128 | 625 | −272 | −1256 | −2231 | −842 | −1085 | 1689 | −810 | −433 | −1540 | −1136 | 52 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 52(K) | 1123 | −2712 | −1604 | −858 | −3236 | −2371 | −691 | −2811 | 2311 | −2638 | −1829 | −1024 | −2404 | 1824 | 1815 | −1432 | −1402 | −2458 | −2653 | −2252 | 53 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 53(V) | 1377 | −1553 | −3986 | −3894 | −2567 | −2622 | −3338 | −77 | −3677 | −1766 | −1504 | −3013 | −3181 | −3423 | −3600 | −1969 | −1667 | 3237 | −3528 | −3166 | 54 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 54(A) | 3105 | −1485 | −3693 | −3696 | −2904 | −2074 | −3074 | −1142 | −3456 | −2386 | −1967 | −2606 | −2765 | −3150 | −3339 | −1426 | −1440 | 1452 | −3559 | −3269 | 55 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 55(E) | −824 | −2036 | −605 | 1957 | −2266 | −1768 | −476 | −1940 | −86 | 258 | −1161 | −452 | −1892 | 1690 | −545 | −750 | 1349 | −1608 | −2277 | −1663 | 56 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 56(M) | 1690 | −1463 | −1381 | −838 | −1839 | −1862 | −861 | −1440 | −562 | −1654 | 2427 | −963 | −2080 | −577 | 1591 | 974 | −820 | −1184 | −2068 | −1599 | 57 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 57(V) | −1994 | −1601 | −4529 | −4123 | −2121 | −4107 | −3665 | 1934 | −3944 | −1135 | −958 | −3809 | −4035 | −3771 | −3974 | −3368 | 1529 | 2897 | −3369 | −2935 | 58 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 58(A) | 1714 | −1019 | −2134 | −1563 | −1061 | −2272 | −1130 | −270 | 1039 | 717 | −221 | −1520 | −2360 | −1150 | −1407 | −1324 | −868 | 1473 | −1543 | −1159 | 59 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 59(S) | 1392 | −1641 | −1697 | −1273 | −3013 | 1054 | −1423 | −2728 | −1098 | −2828 | −1952 | −1262 | −2199 | −1068 | 1609 | 1984 | −1021 | −2082 | −3055 | −2568 | 60 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 60(D) | −1533 | −3153 | 1888 | −194 | −3445 | 1862 | −995 | −3255 | 1471 | −3173 | −2345 | 1731 | −2295 | −601 | −1467 | −1314 | −1531 | −2779 | −3350 | −2542 | 61 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 61(E) | −2454 | −3598 | −734 | 3350 | −4338 | −2504 | −1993 | −4322 | −2069 | −4232 | −3599 | −1369 | 1974 | −1704 | −2642 | −2264 | −2578 | −3797 | −4115 | −3566 | 62 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 62(C) | 1242 | 3033 | −3522 | −3271 | −2183 | 1444 | −2376 | −1404 | −2957 | −2030 | −1366 | −2284 | −2493 | −2598 | −2827 | −1179 | −1123 | 2256 | −2651 | −2354 | 63 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |

TABLE 5-continued

| | | | | | | | | | | | | | | | | | | | | | |
|---|---|---|---|---|---|---|---|---|---|---|---|---|---|---|---|---|---|---|---|---|---|
| 63(D) | −2066 | −3898 | 3072 | 1659 | −4131 | −2061 | −1387 | −4037 | −1584 | −3919 | −3220 | −662 | −2576 | −1047 | −2405 | 1367 | −2129 | −3512 | −4113 | −3127 | 64 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 64(F) | −1017 | −1052 | −2417 | −1841 | 2592 | 743 | −1090 | −537 | −1386 | 992 | −179 | −1687 | −2451 | −1311 | 1219 | −1447 | −968 | −481 | −1233 | −685 | 65 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 65(G) | −3681 | −3593 | −4389 | −4747 | −5281 | 3812 | −4419 | −5908 | −5071 | −5671 | −5288 | −4417 | −4223 | −4850 | −4766 | −3952 | −4069 | −5125 | −4424 | −5214 | 66 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 66(I) | −2267 | −1785 | −4907 | −4580 | −2305 | −4659 | −4548 | 3441 | −4497 | −1089 | −1042 | −4359 | −4451 | −4385 | −4606 | −4018 | −2264 | 1962 | −3955 | −3488 | 67 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 67(V) | −2579 | −2147 | −4998 | −4555 | −1338 | −4582 | −3788 | 186 | −4301 | 2387 | −167 | −4328 | −4258 | −3700 | −4104 | −3890 | −2537 | 2418 | −2919 | −2797 | 68 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 68(I) | 1028 | −1653 | −4289 | −3763 | −1242 | −3743 | −2838 | 2403 | −3462 | 1925 | −162 | −3419 | −3636 | −3025 | −3318 | −2924 | −1918 | 123 | −2418 | −2191 | 69 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 69(C) | −1722 | 5327 | −4261 | −4539 | −4366 | 1681 | −3791 | −4282 | −4361 | −4535 | −3781 | −3241 | −3196 | −4008 | −4052 | −1988 | −2176 | −3300 | −4234 | −4436 | 70 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 70(G) | −3681 | −3593 | −4389 | −4747 | −5281 | 3812 | −4419 | −5908 | −5071 | −5671 | −5288 | −4417 | −4223 | −4850 | −4766 | −3952 | −4069 | −5125 | −4424 | −5214 | 71 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 71(T) | −867 | −1487 | −3134 | −3249 | −3763 | −1745 | −2940 | −3511 | −3192 | −3793 | −2921 | −2264 | −2510 | −2890 | −3152 | 2412 | 3012 | −2488 | −3991 | −3778 | 72 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 72(G) | −3681 | −3593 | −4389 | −4747 | −5281 | 3812 | −4419 | −5908 | −5071 | −5671 | −5288 | −4417 | −4223 | −4850 | −4766 | −3952 | −4069 | −5125 | −4424 | −5214 | 73 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 73(I) | −1456 | −1212 | −3647 | −3087 | −1191 | −3172 | −2148 | 1791 | −2778 | 1612 | −249 | 1689 | −3151 | −2463 | −2697 | −2294 | −1408 | 1572 | −1993 | −1654 | 74 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 74(G) | −3681 | −3593 | −4389 | −4747 | −5281 | 3812 | −4419 | −5908 | −5071 | −5671 | −5288 | −4417 | −4223 | −4850 | −4766 | −3952 | −4069 | −5125 | −4424 | −5214 | 75 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 75(M) | −1505 | −1439 | −2739 | 1280 | −1204 | −2988 | −1884 | 2281 | −2088 | −440 | 3464 | −2268 | −3005 | −1923 | −2202 | −2107 | −1456 | −33 | −2043 | −1709 | 76 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 76(S) | −1333 | −2135 | −1372 | −1436 | −3459 | −2013 | −1821 | −3425 | −1475 | −3465 | −2693 | −1479 | −2581 | 2219 | −1727 | 3042 | −1599 | −2724 | −3495 | −2963 | 77 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 77(I) | −2873 | −2478 | −4720 | −4678 | −2491 | −4148 | −4128 | 3883 | −4491 | −1465 | −1516 | −4385 | −4341 | −4341 | −4380 | −4023 | −2944 | −274 | −3641 | −3325 | 78 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 78(A) | 3577 | −2213 | −3823 | −4109 | −4242 | −2448 | −3656 | −3995 | −4111 | −4316 | −3680 | −3108 | −3185 | −3808 | −3906 | −1985 | −2175 | −3167 | −4199 | −4290 | 79 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 79(A) | 3577 | −2213 | −3823 | −4109 | −4242 | −2448 | −3656 | −3995 | −4111 | −4316 | −3680 | −3108 | −3185 | −3808 | −3906 | −1985 | −2175 | −3167 | −4199 | −4290 | 80 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |

TABLE 5-continued

| | | | | | | | | | | | | | | | | | | | | | |
|---|---|---|---|---|---|---|---|---|---|---|---|---|---|---|---|---|---|---|---|---|---|
| 80(N) | −3232 | −3514 | −2565 | −2905 | −4358 | −3267 | −3364 | −5192 | −3627 | −5059 | −4632 | 4348 | −3843 | −3410 | −3792 | −3319 | −3533 | −4568 | −4087 | −3976 | 81 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 81(K) | −2769 | −3360 | −3563 | −2082 | −4290 | −3219 | −1077 | −3575 | 3452 | −3190 | −2544 | −1922 | −3154 | −661 | 1962 | −2645 | −2419 | −3363 | −2992 | −2942 | 82 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 82(V) | −2562 | −2155 | −4248 | −4013 | 2138 | −3815 | −1138 | −1239 | −3626 | −1489 | −1249 | −2992 | −3772 | −2916 | −3308 | −2976 | −2495 | 2869 | −487 | 2531 | 83 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 83(P) | 1138 | −1825 | −2169 | −1812 | −3266 | −1977 | −1695 | −2922 | −1049 | −3027 | −2235 | −1654 | 3217 | −1386 | 1621 | −1263 | −1362 | −2321 | −3212 | −2864 | 84 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 84(G) | −3681 | −3593 | −4389 | −4747 | −5281 | 3812 | −4419 | −5908 | −5071 | −5671 | −5288 | −4417 | −4223 | −4850 | −4766 | −3952 | −4069 | −5125 | −4424 | −5214 | 85 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 85(I) | 1178 | −1604 | −4535 | −4139 | −2133 | −4064 | −3684 | 2994 | −3965 | −1141 | −968 | −3805 | −4021 | −3786 | −3992 | −3332 | −1991 | 1929 | −3389 | −2957 | 86 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 86(R) | −4070 | −3868 | −4406 | −3890 | −4820 | −3837 | −3026 | −5122 | −1946 | −4739 | −4314 | −3731 | −4155 | −2844 | 4177 | −4178 | −4041 | −4836 | −3949 | −4248 | 87 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 87(C) | 3127 | 3526 | −4003 | −4188 | −3706 | −1841 | −3306 | −3157 | −3846 | −3666 | −2895 | −2592 | −2621 | −3421 | −3568 | −1217 | −1400 | −2337 | −3995 | −3877 | 88 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 88(A) | 3118 | −1485 | −3690 | −3696 | −2915 | −2067 | −3074 | −1169 | −3456 | −2402 | −1981 | −2601 | −2760 | −3150 | −3338 | −1419 | −1438 | 1408 | −3566 | −3277 | 89 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 89(L) | −2621 | −2188 | −5029 | −4579 | −1297 | −4611 | −3789 | 140 | −4321 | 2497 | −125 | −4360 | −4267 | −3687 | −4107 | −3921 | −2576 | 2256 | −2890 | −2788 | 90 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 90(C) | 1598 | 5216 | −4037 | −4247 | −3738 | −1886 | −3358 | −3145 | −3899 | −3690 | −2948 | −2646 | −2666 | −3485 | −3609 | −1272 | −1455 | −2354 | −4021 | −3911 | 91 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 91(W) | −847 | −784 | −2568 | −1982 | −511 | −2297 | −1037 | −302 | −1685 | 769 | 14 | −1718 | −2357 | −1413 | −1689 | 774 | 1162 | −215 | 3352 | 2036 | 92 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 92(D) | −1013 | −2495 | 1532 | 1311 | 1377 | −1771 | −593 | −2538 | −288 | −2499 | −1615 | 1531 | −1973 | −164 | −834 | 1173 | −971 | −2102 | −2688 | −1972 | 93 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 93(H) | −817 | −1384 | −1507 | −1084 | −1784 | −1873 | 2564 | −1410 | −956 | −1673 | −941 | −1146 | 2214 | −877 | −1282 | 988 | −894 | 1344 | −2095 | −1624 | 94 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 94(Y) | −1842 | −3126 | 1667 | −511 | −1838 | −2196 | −1098 | −3110 | −1200 | −3017 | −2371 | −838 | −2565 | 2147 | −1749 | −1638 | −1843 | −2778 | −2296 | 3645 | 95 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 95(M) | −833 | −1274 | −2650 | −2318 | −2137 | −1862 | −1931 | −1658 | −2079 | −1974 | 3504 | −1882 | −2399 | −1915 | −2195 | 1148 | 2537 | −1344 | −2548 | −2193 | 96 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 96(A) | 3577 | −2213 | −3823 | −4109 | −4242 | −2448 | −3656 | −3995 | −4111 | −4316 | −3680 | −3108 | −3185 | −3808 | −3906 | −1985 | −2175 | −3167 | −4199 | −4290 | 97 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |

TABLE 5-continued

| | | | | | | | | | | | | | | | | | | | | | |
|---|---|---|---|---|---|---|---|---|---|---|---|---|---|---|---|---|---|---|---|---|---|
| 97(R) | 1999 | −2479 | −1633 | −1012 | −3127 | −2309 | −867 | −2719 | 83 | −2636 | −1854 | −1142 | −2449 | 1831 | 2446 | −1447 | −1431 | −2360 | −2716 | −2321 | 98 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 98(M) | −3154 | −2620 | −5525 | −4938 | −957 | −5202 | −3935 | 1746 | −4695 | 2559 | 2719 | −4894 | −4446 | −3636 | −4262 | −4494 | −3018 | −926 | −2688 | −2829 | 99 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 99(S) | 2331 | −1459 | −3358 | −3521 | −3885 | −1723 | −3093 | −3652 | −3467 | −3930 | −3025 | −2336 | −2506 | −3077 | −3353 | 2771 | −1296 | −2534 | −4111 | −3952 | 100 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 100(R) | −4070 | −3868 | −4406 | −3890 | −4820 | −3837 | −3026 | −5122 | −1946 | −4739 | −4314 | −3731 | −4155 | −2844 | 4177 | −4178 | −4041 | −4836 | −3949 | −4248 | 101 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 101(W) | −116 | 672 | 45 | 325 | −317 | −673 | 804 | −480 | 420 | −880 | 565 | 301 | −446 | 634 | 168 | −75 | 58 | −423 | 1003 | 81 | 102 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 102(E) | −836 | −2091 | −540 | 2043 | −2343 | −1754 | −487 | 1015 | −118 | −2081 | −1230 | −432 | −1892 | 1663 | −598 | 904 | −784 | −1672 | −2338 | −1704 | 103 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 103(H) | −4406 | −3961 | −3921 | −4171 | −3231 | −3926 | 5401 | −5468 | −3992 | −5013 | −4849 | −4130 | −4378 | −4151 | −3893 | −4548 | −4592 | −5195 | −3383 | −2818 | 104 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 104(N) | −3232 | −3514 | −2565 | −2905 | −4358 | −3267 | −3364 | −5192 | −3627 | −5059 | −4632 | 4348 | −3843 | −3410 | −3792 | −3319 | −3533 | −4568 | −4087 | −3976 | 105 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 105(D) | −2358 | −4145 | 3182 | −424 | −4431 | −2177 | −1648 | −4495 | −2025 | −4352 | −3768 | 2917 | −2760 | −1348 | −2952 | −2013 | −2474 | −3924 | −4442 | −3425 | 106 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 106(A) | 3194 | −1459 | −3484 | −3625 | −3734 | −1755 | −3095 | −3265 | −3460 | −3690 | −2869 | −2384 | −2530 | −3106 | −3321 | −1118 | 1557 | −2359 | −4008 | −3849 | 107 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 107(N) | −2080 | −3282 | −571 | −790 | −3700 | −2288 | −1530 | −3842 | −1203 | −3719 | −3049 | 3691 | −2763 | 2236 | −1546 | −1908 | −2165 | −3350 | −3610 | −2909 | 108 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 108(I) | −2342 | −1862 | −4934 | −4526 | −1839 | −4657 | −4129 | 3048 | −4390 | 1219 | −617 | −4313 | −4352 | −4035 | −4357 | −3961 | −2310 | 1756 | −3416 | −3152 | 109 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 109(L) | −2474 | −2000 | −5009 | −4549 | −1506 | −4685 | −3925 | 2021 | −4370 | 2279 | −300 | −4348 | −4307 | −3824 | −4225 | −3966 | −2422 | 1754 | −3091 | −2958 | 110 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 110(C) | 2049 | 3245 | −3519 | −3308 | −2421 | 1482 | −2476 | −1789 | −3007 | −2304 | −1604 | −2272 | −2469 | −2649 | −2890 | −1125 | −1135 | 1329 | −2854 | −2572 | 111 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 111(I) | −2258 | −1872 | −4687 | −4134 | 1767 | −4166 | −3117 | 1920 | −3850 | 1870 | −15 | −3821 | −3889 | −3252 | −3621 | −3354 | −2187 | 1613 | −2474 | −2317 | 112 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 112(G) | −2025 | −2501 | −3252 | −3562 | −4636 | 3423 | −3593 | −4733 | −3987 | −4806 | −4072 | −3048 | 1823 | −3657 | −3934 | −2250 | −2455 | −3689 | −4320 | −4566 | 113 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 113(E) | −1494 | −2693 | −395 | 2314 | −3675 | 2184 | −1408 | −3492 | −1389 | −3481 | −2679 | −859 | −2439 | −1060 | −1986 | 1095 | −1645 | −2877 | −3669 | −2925 | 114 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |

TABLE 5-continued

| | | | | | | | | | | | | | | | | | | | | | |
|---|---|---|---|---|---|---|---|---|---|---|---|---|---|---|---|---|---|---|---|---|---|
| 114(R) | −4070 | −3868 | −4406 | −3890 | −4820 | −3837 | −3026 | −5122 | −1946 | −4739 | −4314 | −3731 | −4155 | −2844 | 4177 | −4178 | −4041 | −4836 | −3949 | −4248 | 115 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 115(M) | −1427 | −1193 | −3701 | −3112 | −983 | −3093 | −2034 | 180 | −2770 | 1017 | 2778 | −2712 | −3065 | −2386 | −2624 | −2210 | 1347 | 2148 | −1810 | −1513 | 116 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 116(H) | −1008 | −888 | −2923 | −2346 | −929 | −2548 | 2597 | 1535 | −2026 | −676 | −116 | −2056 | −2607 | −1772 | −2006 | −1637 | 1320 | 2074 | −1492 | −1124 | 117 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 117(G) | −1110 | −1709 | −3106 | −3357 | −4046 | 3242 | −3166 | −3842 | −3502 | −4106 | −3252 | −2451 | −2702 | −3156 | −3425 | −1349 | 1883 | −2772 | −4162 | −4067 | 118 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 118(V) | 929 | −1443 | −4036 | −3547 | −1453 | −3385 | −2674 | 364 | −3251 | 1653 | −427 | −3137 | −3432 | −2922 | −3158 | −2578 | −1681 | 2482 | −2440 | −2125 | 119 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 119(E) | 1257 | −3590 | 1744 | 2835 | −3875 | −2022 | −1272 | −3730 | −1355 | −3645 | −2894 | −639 | −2490 | −916 | −2095 | −1605 | −1921 | −3229 | −3840 | −2931 | 120 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 120(L) | −1618 | −1542 | −2809 | 1300 | −1194 | −3091 | −2015 | −38 | −2244 | 2157 | −192 | −2386 | −3103 | −2043 | −2351 | −2230 | −1572 | 1529 | −2118 | −1807 | 121 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 121(A) | 2991 | −1555 | −3668 | −3533 | −2323 | −2475 | −2954 | 1759 | −3277 | −1606 | −1355 | −2778 | −3028 | −3047 | −3226 | −1812 | −1600 | −325 | −3174 | −2823 | 122 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 122(F) | −1286 | −1561 | −2176 | −1442 | 1607 | −2460 | −947 | −1068 | 1345 | 1590 | −603 | −1448 | −2487 | −784 | 1605 | −1533 | −1185 | −1008 | −1748 | −1316 | 123 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 123(W) | 1015 | −1816 | 1148 | 1268 | −1999 | −1728 | −432 | −1665 | −102 | −1774 | 2024 | −436 | −1835 | −38 | −580 | −680 | −661 | −1365 | 2839 | −1494 | 124 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 124(I) | −2873 | −2478 | −4720 | −4678 | −2491 | −4148 | −4128 | 3883 | −4491 | −1465 | −1516 | −4385 | −4341 | −4341 | −4380 | −4023 | −2944 | −274 | −3641 | −3325 | 125 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 125(V) | −2255 | −1772 | −4901 | −4575 | −2348 | −4657 | −4567 | 2056 | −4497 | −1141 | −1081 | −4354 | −4453 | −4405 | −4618 | −4017 | −2252 | 3294 | −3996 | −3509 | 126 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 126(D) | −2267 | −2933 | 3576 | −1195 | −3049 | −2596 | −2082 | 1629 | −2341 | −2627 | −2373 | −1509 | −3085 | −1871 | −2936 | −2291 | −2378 | −1639 | −3578 | −2919 | 127 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 127(T) | 2302 | −1457 | −3444 | −3557 | −3687 | −1757 | −3050 | −3212 | −3391 | −3635 | −2820 | −2365 | −2526 | −3052 | −3274 | −1117 | 3078 | −2331 | −3963 | −3792 | 128 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 128(W) | −4265 | −3318 | −4806 | −5090 | 3775 | −4602 | −1029 | −3119 | −4653 | −2459 | −2540 | −3390 | −4514 | −3496 | −4074 | −3946 | −4152 | −3319 | 4590 | 900 | 129 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 129(L) | −2756 | −2316 | −5126 | −4663 | −1192 | −4704 | −3809 | 2 | −4390 | 2758 | −16 | −4468 | −4303 | −3665 | −4126 | −4024 | −2700 | 1709 | −2823 | −2772 | 130 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 130(Q) | −734 | −2114 | −590 | −69 | −2474 | 628 | −384 | −2203 | 1300 | −2173 | −1269 | −365 | −1805 | 1784 | −417 | 893 | 1322 | −1774 | −2356 | −1702 | 131 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |

TABLE 5-continued

| | | | | | | | | | | | | | | | | | | | | | |
|---|---|---|---|---|---|---|---|---|---|---|---|---|---|---|---|---|---|---|---|---|---|
| 131(T) | 2138 | −1458 | −3440 | −3556 | −3688 | −1758 | −3051 | −3210 | −3392 | −3636 | −2822 | −2366 | −2528 | −3053 | −3274 | −1119 | 3193 | −2331 | −3964 | −3794 | 132 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 132(P) | −1757 | −3237 | −258 | 1435 | −3607 | −2077 | −1164 | −3400 | −916 | −3319 | −2549 | −731 | 3132 | 1857 | −1396 | −1544 | −1767 | −2952 | −3466 | −2728 | 133 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 133(W) | −4382 | −3341 | −4820 | −5151 | 3666 | −4691 | −907 | −3282 | −4707 | −2619 | −2695 | −3319 | −4550 | −3452 | −4084 | −3936 | −4237 | −3432 | 3961 | 2712 | 134 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 134(S) | −1405 | −3017 | 1625 | 1413 | −3291 | −1894 | −892 | −3094 | −722 | −3018 | −2168 | −505 | −2213 | 1798 | −1331 | 2056 | −1390 | −2623 | −3196 | −2403 | 135 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 135(G) | −2298 | −2923 | −2103 | −2123 | −4319 | 3238 | −2236 | −4181 | 1859 | −4078 | −3400 | −2169 | −3219 | −1952 | −1577 | −2354 | −2488 | −3582 | −3805 | −3682 | 136 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 136(G) | 1377 | −2300 | −719 | 1534 | −3577 | 2593 | −1598 | −3339 | −1577 | −3413 | −2605 | −1073 | −2447 | −1275 | −2099 | −1324 | −1539 | −2684 | −3628 | −2995 | 137 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −955 | −7714 | −1061 | −894 | −1115 | −701 | −1378 | * | * | | | | | | | | | | | | |
| 137(Q) | −1004 | −2435 | 277 | 2184 | −2728 | −1440 | −405 | −2509 | −53 | −2439 | −1658 | −87 | −1766 | 2784 | −483 | −813 | −984 | −2099 | −2581 | −1891 | 138 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −20 | −6778 | −7821 | −894 | −1115 | −205 | −2915 | * | * | | | | | | | | | | | | |
| 138(R) | −4070 | −3868 | −4406 | −3890 | −4820 | −3837 | −3026 | −5122 | −1946 | −4739 | −4314 | −3731 | −4155 | −2844 | 4177 | −4178 | −4041 | −4836 | −3949 | −4248 | 139 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 139(H) | −4406 | −3961 | −3921 | −4171 | −3231 | −3926 | 5401 | −5468 | −3992 | −5013 | −4849 | −4130 | −4378 | −4151 | −3893 | −4548 | −4592 | −5195 | −3383 | −2818 | 140 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 140(Q) | 1807 | −2632 | −381 | 1381 | −3040 | −1903 | −848 | −2779 | −523 | −2755 | −1915 | −597 | −2182 | 2784 | −1005 | −1124 | −1254 | −2346 | −2947 | −2259 | 141 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 141(R) | −1893 | −2803 | −2103 | −1310 | −3474 | −2617 | −907 | −2983 | 247 | −2805 | −2065 | −1373 | −2680 | 1875 | 3184 | −1815 | 1244 | −2674 | −2793 | −2506 | 142 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 142(R) | −4070 | −3868 | −4406 | −3890 | −4820 | −3837 | −3026 | −5122 | −1946 | −4739 | −4314 | −3731 | −4155 | −2844 | 4177 | −4178 | −4041 | −4836 | −3949 | −4248 | 143 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 143(I) | −2264 | −1775 | −4915 | −4588 | −2348 | −4686 | −4596 | 3178 | −4516 | −1133 | −1075 | −4374 | −4468 | −4422 | −4639 | −4047 | −2259 | 2464 | −4009 | −3526 | 144 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 144(E) | −1362 | −2952 | 1820 | 2207 | −3237 | 905 | −855 | −3031 | −644 | −2955 | −2100 | −503 | −2190 | −446 | 1395 | −1165 | −1342 | −2565 | −3129 | −2354 | 145 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 145(K) | 908 | −1736 | −1815 | −1248 | −2070 | −2279 | −1093 | 1542 | 2712 | −1686 | −1079 | −1330 | −2446 | −804 | −667 | −1390 | −1204 | −917 | −2305 | −1891 | 146 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 146(I) | −2723 | −2229 | −5174 | −4732 | −1356 | −4887 | −4035 | 3364 | −4508 | 1438 | −167 | −4582 | −4423 | −3856 | −4303 | −4226 | −2664 | 18 | −3022 | −2924 | 147 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 147(R) | 1056 | −2064 | 1249 | −109 | −2476 | 670 | −454 | −2205 | −68 | −2198 | −1301 | −400 | −1828 | −15 | 1385 | −649 | 1095 | −1771 | −2401 | −1745 | 148 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |

TABLE 5-continued

| | | | | | | | | | | | | | | | | | | | | | |
|---|---|---|---|---|---|---|---|---|---|---|---|---|---|---|---|---|---|---|---|---|---|
| 148(E) | 2045 | −2691 | −641 | 2925 | −3737 | −2085 | −1663 | −3447 | −1644 | −3560 | −2829 | −1109 | −2614 | −1347 | −2170 | −1596 | −1833 | −2895 | −3749 | −3104 | 149 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7714 | −8756 | −894 | −1115 | −701 | −1378 | * | * | | | | | | | | | | | | |
| 149(I) | −1835 | −1485 | −4226 | −3745 | −1377 | −3738 | −2668 | 2965 | −3461 | −847 | −625 | −3338 | −3665 | −3150 | −3370 | −2919 | −1800 | 1729 | −2313 | 2304 | 150 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −268 | −7714 | −2600 | −894 | −1115 | −701 | −1378 | * | * | | | | | | | | | | | | |
| 150(E) | −3293 | −3786 | −1473 | 3826 | −4560 | −2970 | −2663 | −4846 | −2841 | −4681 | −4279 | −2142 | −3486 | −2508 | −3255 | −3136 | −3421 | −4441 | −4028 | −4008 | 151 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −12 | −7457 | −8500 | −894 | −1115 | −1422 | −674 | * | * | | | | | | | | | | | | |
| 151(R) | 1141 | −2442 | −1246 | −549 | −2918 | −2090 | −473 | −2524 | 1742 | −2382 | −1557 | −744 | −2136 | 1966 | 2040 | −1122 | −1108 | −2160 | −2431 | −1985 | 152 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −12 | −7457 | −8500 | −894 | −1115 | −383 | −2099 | * | * | | | | | | | | | | | | |
| 152(W) | −116 | 672 | 45 | 325 | −317 | −673 | 804 | −480 | 420 | −880 | 565 | 301 | −446 | 634 | 168 | −75 | 58 | −423 | 1003 | 81 | 153 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −268 | −7714 | −2600 | −894 | −1115 | −701 | −1378 | * | * | | | | | | | | | | | | |
| 153(R) | −892 | −2132 | −875 | −271 | −2550 | −1817 | −388 | −2214 | 1600 | −2162 | −1306 | −513 | −1909 | 48 | 1621 | 1177 | 1556 | −1830 | −2302 | −1759 | 154 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −12 | −7457 | −8500 | −894 | −1115 | −1422 | −674 | * | * | | | | | | | | | | | | |
| 154(H) | −2093 | −2537 | −2330 | −1682 | −355 | −2870 | 4028 | −2443 | −365 | −2250 | −1763 | −1614 | −2893 | −919 | 1830 | −2037 | −1948 | −2306 | −903 | 2497 | 155 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −12 | −7457 | −8500 | −894 | −1115 | −1422 | −674 | * | * | | | | | | | | | | | | |
| 155(N) | 1159 | −2195 | −259 | 1687 | −2630 | −1609 | −505 | −2379 | −193 | −2358 | −1475 | 1694 | −1837 | −80 | −721 | 1098 | −811 | −1925 | −2555 | −1863 | 156 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −315 | −7457 | −2393 | −894 | −1115 | −1422 | −674 | * | * | | | | | | | | | | | | |
| 156(K) | 1690 | −1521 | −865 | −530 | −2502 | 1533 | −757 | −2176 | 1750 | −2258 | −1424 | −660 | −1836 | −385 | −644 | −643 | −725 | −1677 | −2484 | −1967 | 157 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −399 | −7158 | −2093 | −894 | −1115 | −1887 | −455 | * | * | | | | | | | | | | | | |
| 157(N) | −790 | −1650 | −328 | −436 | −2633 | −1372 | −1008 | −2562 | −866 | −2649 | −1902 | 2721 | 2673 | −726 | −1253 | −817 | −995 | −2001 | −2694 | −2132 | 158 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −20 | −6778 | −7821 | −894 | −1115 | −2238 | −344 | * | * | | | | | | | | | | | | |
| 158(P) | −1088 | −1976 | −873 | −547 | −2653 | −1746 | −572 | −2325 | 2405 | −2286 | −1551 | −699 | 2531 | −199 | 98 | −1053 | −1080 | −1961 | −2327 | −1945 | 159 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −20 | −6778 | −7821 | −894 | −1115 | −2238 | −344 | * | * | | | | | | | | | | | | |
| 159(V) | −426 | −819 | −2080 | −1971 | −1792 | 2096 | −1692 | −548 | −1871 | −1495 | −974 | −1512 | −1984 | −1695 | −1954 | −748 | −707 | 2424 | −2283 | −1922 | 160 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −20 | −6778 | −7821 | −894 | −1115 | −2238 | −344 | * | * | | | | | | | | | | | | |
| 160(P) | −582 | −884 | −2096 | −1889 | −1505 | −1633 | −1594 | −145 | −1691 | −1065 | −663 | −1563 | 2575 | −1584 | −1800 | −950 | −795 | 2279 | −2100 | −1706 | 161 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −20 | −6778 | −7821 | −894 | −1115 | −2238 | −344 | * | * | | | | | | | | | | | | |
| 161(K) | −1017 | −1896 | −750 | −549 | −2759 | 2163 | −702 | −2465 | 2406 | −2443 | −1689 | −704 | −1983 | −342 | −168 | −1002 | −1075 | −2029 | −2466 | −2077 | 162 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −636 | −6778 | −1526 | −894 | −1115 | −2238 | −344 | * | * | | | | | | | | | | | | |
| 162(A) | 2922 | −540 | −1434 | −1448 | −1894 | −835 | −1345 | −1218 | −1400 | −1722 | −1180 | −1009 | −1484 | −1278 | −1495 | −255 | −368 | −799 | −2185 | −1887 | 163 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −30 | −6173 | −7215 | −894 | −1115 | −2556 | −269 | * | * | | | | | | | | | | | | |
| 163(P) | −1156 | −1409 | −1589 | −1713 | −2421 | −1496 | −1697 | −2442 | −1763 | −2529 | −2100 | −1603 | 3866 | −1742 | −1822 | −1358 | −1449 | −2044 | −2236 | −2262 | 164 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −30 | −6173 | −7215 | −894 | −1115 | −2556 | −269 | * | * | | | | | | | | | | | | |
| 164(A) | 2922 | −540 | −1434 | −1448 | −1894 | −835 | −1345 | −1218 | −1400 | −1722 | −1180 | −1009 | −1484 | −1278 | −1495 | −255 | −368 | −799 | −2185 | −1887 | 165 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −30 | −6173 | −7215 | −894 | −1115 | −162 | −3233 | * | * | | | | | | | | | | | | |

TABLE 5-continued

| | | | | | | | | | | | | | | | | | | | | | |
|---|---|---|---|---|---|---|---|---|---|---|---|---|---|---|---|---|---|---|---|---|---|
| 165(W) | −116 | 672 | 45 | 325 | −317 | −673 | 804 | −480 | 420 | −880 | 565 | 301 | −446 | 634 | 168 | −75 | 58 | −423 | 1003 | 81 | 166 |
| — | * | * | * | * | * | * | * | * | * | * | * | * | * | * | * | * | * | * | * | * | |
| — | * | * | * | * | * | * | * | * | 0 | | | | | | | | | | | | |

[1]Program name and version
[2]Name of the input sequence alignment file
[3]Length of the alignment: include indels
[4]Type of residues
[5]Map of the match states to the columns of the alignment
[6]Commands used to generate the file: this one means that hmmbuild (default parameters) was applied to the alignment file
[7]Commands used to generate the file: this one means that hmmcalibrate (default parameters) was pplied to the hmm profile
[8]Number of sequences in the alignment
[9]When the file was generated
[10]The trasition probability distribution for the null model (single G state).
[11]The symbol emission probability distribution for the null model (G tate); consists of K integers. The null probability used to convert these back to model probabilities is 1/K.
[12]The extreme value distribution parameters μ and lambda respectively, both floating point values. Lambda is positive and nonzero. These values are set when the model is calibrated with hmmcalibrate.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US08679822B2). An electronic copy of the "Sequence Listing" will also be available from the USPTO upon request and payment of the fee set forth in 37 CFR 1.19(b)(3).

What is claimed is:

1. A recombinant bacterial host cell comprising:

a) a xylose metabolic pathway comprising at least one gene encoding a polypeptide having xylose isomerase activity;

b) at least one gene encoding a polypeptide having ribose-5-phosphate isomerase activity selected from the group consisting of ribose-5-phosphate isomerase A and ribose-5-phosphate isomerase B; and c) at least one genetic modification which increases ribose-5-phosphate isomerase activity in the host cell as compared with ribose-5-phosphate isomerase activity in the host cell lacking said genetic modification;

wherein the bacterial host cell utilizes xylose to produce ethanol; and wherein the bacterial host cell is selected from the group consisting of *Zymomonas* and *Zymobacter*.

2. The recombinant host cell of claim 1 wherein the at least one genetic modification of step (c) is over-expression of an endogenous gene encoding a polypeptide having ribose-5-phosphate isomerase activity.

3. The recombinant host cell of claim 1 wherein the at least one genetic modification of step (c) is expression of at least one non-endogenous gene encoding a polypeptide having ribose-5-phosphate isomerase activity.

4. The recombinant microorganism of claim 1 wherein the polypeptide having ribose-5-phosphate isomerase activity has the EC classification EC 5.3.1.6.

5. The recombinant host cell of claim 1 wherein the ribose-5-phosphate isomerase A polypeptide:

i) gives an E-value score of 0.1 or less when queried using a Profile Hidden Markov Model prepared using SEQ ID NOs:, 86, 96, and 97; the query being carried out using the hmmsearch algorithm wherein the Z parameter is set to 1 billion, and ii) has aspartic acid and glutamic acid at positions corresponding to 107 and 129, respectively, in the *Saccharomyces cerevisiae* RPI-A protein of SEQ ID NO:97.

6. The recombinant host cell of claim 1 wherein the ribose-5-phosphate isomerase A has an amino acid sequence having at least 90% identity to an amino acid sequence selected from the group consisting of SEQ ID NOs:86, 96 and 97 based on the Clustal W method of alignment using the default parameters of GAP PENALTY=10, GAP LENGTH PENALTY=0.1, and Gonnet 250 series of protein weight matrix.

7. The recombinant host cell of claim 6 wherein the ribose-5-phosphate isomerase A has an amino acid sequence having at least 90% identity to an amino acid sequence selected from the group consisting of SEQ ID NOs: 86, 96, and 97 based on the Clustal W method of alignment using the default parameters of GAP PENALTY=10, GAP LENGTH PENALTY=0.1, and Gonnet 250 series of protein weight matrix.

8. The recombinant host cell of claim 1 wherein said microorganism further comprises at least one genetic modification which increases xylose isomerase activity as compared to xylose isomerase activity in the microorganism lacking said genetic modification.

9. The recombinant host cell of claim 1 wherein the gene encoding a polypeptide having xylose isomerase activity is over-expressed.

10. The recombinant microorganism of claim 1 wherein the gene encoding a polypeptide having xylose isomerase activity is expressed in multicopy.

11. A process for producing ethanol comprising:

a) providing a recombinant bacterial host cell of claim 1; and b) culturing the bacterial host cell of (a) in a medium comprising xylose whereby xylose is converted to ethanol.

12. The process of claim 11 wherein the medium comprises either a mixture of sugars including xylose or xylose as a sole sugar.

* * * * *